United States Patent
Zhang et al.

(10) Patent No.: US 12,398,119 B2
(45) Date of Patent: *Aug. 26, 2025

(54) PIPERAZINE AZASPIRO DERIVATIVES

(71) Applicant: PFIZER INC., New York, NY (US)

(72) Inventors: Lei Zhang, Auburndale, MA (US); Erik Alphie LaChapelle, Uncasville, CT (US); Christopher Ryan Butler, Canton, MA (US); Natasha Mariam Kablaoui, Newton, MA (US); Michael Aaron Brodney, Newton, MA (US); Laura Ann McAllister, Arlington, MA (US); Qingyi Yang, Lexington, MA (US); Christopher John Helal, Mystic, CT (US); Damien Webb, Bottminggen (CH)

(73) Assignee: PFIZER INC., New York, NY (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/969,479

(22) Filed: Oct. 19, 2022

(65) Prior Publication Data

US 2023/0192654 A1 Jun. 22, 2023

Related U.S. Application Data

(63) Continuation of application No. 17/040,479, filed as application No. PCT/US2019/023916 on Mar. 25, 2019, now Pat. No. 11,524,954.

(60) Provisional application No. 62/647,106, filed on Mar. 23, 2018.

(51) Int. Cl.
| | |
|---|---|
| C07D 401/14 | (2006.01) |
| C07D 401/12 | (2006.01) |
| C07D 413/14 | (2006.01) |
| C07D 417/14 | (2006.01) |
| C07D 471/04 | (2006.01) |
| C07D 491/107 | (2006.01) |

(52) U.S. Cl.
CPC ......... *C07D 401/14* (2013.01); *C07D 401/12* (2013.01); *C07D 413/14* (2013.01); *C07D 417/14* (2013.01); *C07D 471/04* (2013.01); *C07D 491/107* (2013.01)

(58) Field of Classification Search
CPC .. C07D 401/14; C07D 401/12; C07D 413/14; C07D 417/14; C07D 471/04

USPC .......................................................... 514/210
See application file for complete search history.

(56) References Cited

FOREIGN PATENT DOCUMENTS

| | | |
|---|---|---|
| WO | WO2005030188 | 4/2005 |
| WO | 2005117883 | 12/2005 |
| WO | WO2015118342 | 8/2015 |
| WO | WO2016147011 | 9/2016 |
| WO | WO2017021728 | 2/2017 |
| WO | WO2017021729 | 2/2017 |
| WO | WO2017021730 | 2/2017 |
| WO | 2018/229511 A1 | 12/2018 |

OTHER PUBLICATIONS

Ghosh "Drug discovery for autism spectrum disorder: challenges and opportunities" Nature Reviews Drug Discovery (2013), 12(10), 777-790.
Hoffer "Repositioning drugs for traumatic brain injury—N-acetyl cysteine and Phenserine" Journal of Biomedical Science (2017) 24: 71.

*Primary Examiner* — Ana Z Muresan
(74) *Attorney, Agent, or Firm* — Haley Guiliano LLP

(57) ABSTRACT

The present invention provides, in part, compounds of Formula I: or an N-oxide thereof, or a pharmaceutically acceptable salt of the compound or the N-oxide, wherein: $X^1$, $X^2$, $R^1$, $R^2$, m and n are as described herein; processes for the preparation of; intermediates used in the preparation of; and compositions containing such compounds, N-oxides, or salts, and their uses for treating M4-mediated (or M4-associated) disorders including, e.g., Alzheimer's Disease, Parkinson's Disease, schizophrenia (e.g., its cognitive and negative symptoms), pain, addiction, and a sleep disorder.

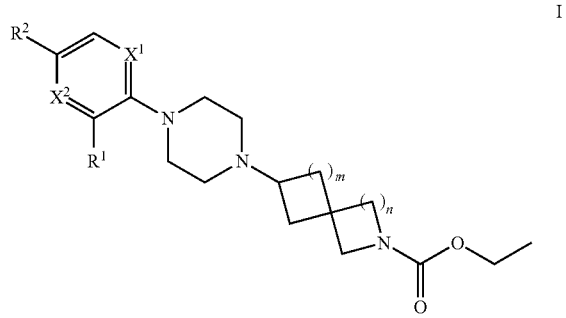

3 Claims, No Drawings

PIPERAZINE AZASPIRO DERIVATIVES

CROSS-REFERENCE TO RELATED APPLICATIONS

This application is a continuation of U.S. patent application Ser. No. 17/040,479, filed Sep. 22, 2020, now U.S. Pat. No. 11,524,954 issued Dec. 13, 2022, which is a United States National Phase Application filed under 35 U.S.C. § 371 from International Patent Application No. PCT/US2019/023916, filed Mar. 25, 2019, which claims the benefit of priority to U.S. Provisional Patent Application Ser. No. 62/647,106, filed Mar. 23, 2018, the disclosures of which are incorporated herein by reference in their entireties.

FIELD OF THE INVENTION

The present invention generally relates to novel piperazine azaspiro derivatives, salts thereof, pharmaceutical compositions thereof, which are agonists of the muscarinic M4 receptor, and are useful in the treatment of M4-mediated diseases and disorders such as Schizophrenia, Alzheimer's Disease, Dementia with Lewy Bodies, Parkinson's Disease and related memory and executive dysfunction, agitation, and psychosis associated therewith.

BACKGROUND OF THE INVENTION

Patients with Schizophrenia, Alzheimer's Disease, Parkinson's Disease, Huntington's Disease, depression and various other neurological/neurodegenerative diseases frequently suffer from behavioral and cognitive impairments resulting in debilitating disruption to their daily lives. Over the years many pharmacological treatments have been discovered that provide some improvement in behavior and cognitive function. However, the improvement is modest at best, and as is often the case, the underlying dose-limiting adverse effects associated with these treatments, including extrapyramidal and metabolic side-effects, lead to partial responsiveness, and non-compliance.

In an effort to discover new and improved pharmacological treatments, researchers began to look at the muscarinic acetylcholine receptor (mAChR) as a viable mechanism. There are five mAChRs subtypes (M1-M5) that have been identified and are part of the G protein-coupled receptor (GPCR) superfamily. These subtypes are distributed widely throughout the periphery and the central nervous system (CNS), with the M1 and M4 subtypes being predominantly expressed in the CNS.

Researchers have since focused on identifying subtype selective M4 muscarinic acetylcholine receptor activators. For example, positive allosteric modulators (PAMs) of the M4 muscarinic acetylcholine receptor have been studied. In addition to M4 PAMs, researches have also focused on identifying agonists of the M4 receptor. In fact, the M4 agonist HTL0016878 being developed for the treatment of major symptoms of Alzheimer's Disease entered into a Phase I clinical study. However, new or improved activators, including agonists of the muscarinic M4 receptors are needed for providing new and improved therapies to treat M4-mediated diseases and disorders such as Parkinson's Disease, Schizophrenia, Alzheimer's Disease and others described herein.

SUMMARY OF THE INVENTION

The present invention provides, in part, a compound of Formula I:

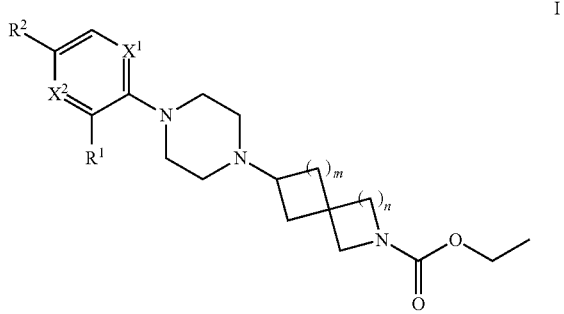

or an N-oxide thereof, or a pharmaceutically acceptable salt of the compound or the N-oxide, wherein:

$X^1$ and $X^2$ are each independently CH or nitrogen, provided that $X^1$ and $X^2$ cannot both be CH, $R^1$ is selected from the group consisting of halogen, cyano, hydroxy, —$SF_5$, nitro, —$N(R^6)(R^7)$, ($C_1$-$C_6$) alkyl, ($C_2$-$C_6$)alkenyl, ($C_2$-$C_6$)alkynyl, ($C_1$-$C_6$)alkylthio, ($C_1$-$C_6$)alkoxy, ($C_3$-$C_6$)cycloalkyl, —O-(4- to 6-membered)heterocycloalkyl, ($C_6$-$C_{10}$)aryl, (5- to 10-membered)heteroaryl and (4- to 8-membered)heterocycloalkyl, wherein said ($C_1$-$C_6$)alkyl, ($C_2$-$C_6$)alkenyl, ($C_2$-$C_6$)alkynyl, ($C_1$-$C_6$)alkylthio, ($C_1$-$C_6$)alkoxy, ($C_3$-$C_6$)cycloalkyl, —O-(4- to 6-membered)heterocycloalkyl, ($C_6$-$C_{10}$)aryl, (5- to 10-membered)heteroaryl and (4- to 8-membered)heterocycloalkyl are optionally substituted with 1 to 3 substituents selected from the group consisting of halogen, cyano, hydroxy, —$N(R^6)(R^7)$, ($C_1$-$C_6$)alkyl, ($C_1$-$C_6$)alkoxy, ($C_3$-$C_6$)cycloalkyl, and (5- to 6-membered)heteroaryl, wherein said ($C_1$-$C_6$)alkyl, ($C_1$-$C_6$)alkoxy, and (5- to 6-membered)heteroaryl are optionally substituted with 1 to 3 substituents selected from the group consisting of halogen, cyano, hydroxy, ($C_1$-$C_6$)alkyl and ($C_1$-$C_6$)alkoxy;

$R^2$ is selected from the group consisting of hydrogen, halogen, cyano, hydroxy, —$SF_5$, nitro, —$N(R^6)(R^7)$, ($C_1$-$C_6$)alkyl, and ($C_1$-$C_6$)alkoxy, wherein said ($C_1$-$C_6$) alkyl and ($C_1$-$C_6$)alkoxy are optionally substituted with 1 to 3 halogen;

$R^6$ and $R^7$ are each independently selected from hydrogen, ($C_1$-$C_6$)alkyl or $C(O)CH_3$;

m is 1 or 2; and n is 1 or 2.

The compounds of Formulas I, $I^A$, $I^B$, $I^C$ and I' are useful for treating an M4-mediated (or M4-associated) disease or disorder in a patient, wherein the method involves administering to a patient a therapeutically effective amount of a compound of Formulas I, $I^A$, $I^B$, $I^C$ and I', or an N-oxide thereof, or a pharmaceutically acceptable salt of the compound or the N-oxide.

The present invention is also directed to the use of the compounds described herein, or an N-oxide thereof, or a pharmaceutically acceptable salt of the compound or the N-oxide, for the treatment of M4-mediated (or M4-associated) disease or disorder wherein the disease or disorder is Alzheimer's disease, schizophrenia or psychosis, pain, addiction, a sleep disorder, a cognitive disorder (e.g. mild cognitive impairment), Parkinson's disease, Parkinson's disease-levodopa-induced dyskinesia, Huntington's disease, dyskinesia, dry mouth, pulmonary hypertension, chronic obstructive pulmonary disease (COPD), asthma, urinary incontinence, glaucoma, Trisomy 21 (Down syndrome), cerebral amyloid angiopathy, dementia, hereditary cerebral hemorrhage with amyloidosis of the Dutch type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis.

The present invention is also directed to pharmaceutical formulations containing a therapeutically effective amount of a compound of Formulas I, $I^A$, $I^B$, $I^C$ and I', or an N-oxide thereof, or a pharmaceutically acceptable salt of the compound or the N-oxide, and a pharmaceutically acceptable excipient.

It is to be understood that both the foregoing general description and the following detailed description are exemplary and explanatory only and are not restrictive of the invention, as claimed.

DETAILED DESCRIPTION OF THE INVENTION

The headings within this document are being utilized only to expedite its review by the reader. They should not be construed as limiting the invention or claims in any manner.

Definitions and Exemplifications The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

As used herein, the term "agonist of the muscarinic M4 receptor" means the compounds of the present invention induce an effect on the M4 receptor absent the presence of a native ligand (e.g. acetylcholine) As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl ring.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl.

For another example, the term "a 5-to 10-membered heteroaryl group" is specifically intended to include any 5-, 6-, 7-, 8-, 9- or 10-membered heteroaryl group.

The term "$(C_1-C_6)$alkyl", as used herein, refers to a saturated, branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl. The $(C_1-C_6)$alkyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl. For example, a $(C_1-C_6)$alkyl moiety can be substituted with one or more halogen atoms to form a "halo$(C_1-C_6)$alkyl". Representative examples of a halo$(C_1-C_6)$alkyl include, but are not limited to, fluoromethyl, 2-fluoroethyl, difluoromethyl, trifluoromethyl, and pentafluoroethyl. Other representative examples of a substituted $(C_1-C_6)$alkyl include, but are not limited to cyanobutyl and ethoxyethyl.

The term "$(C_2-C_6)$alkenyl" refers to an aliphatic hydrocarbon having from 2 to 6 carbon atoms and having at least one carbon-carbon double bond, including straight chain or branched chain groups having at least one carbon-carbon double bond. Representative examples include, but are not limited to, ethenyl, 1-propenyl, 2-propenyl (allyl), isopropenyl, 2-methyl-1-propenyl, 1-butenyl, 2-butenyl, and the like. When the compounds of the invention contain a $(C_2-C_6)$alkenyl group, the compound may exist as the pure E (entgegen) form, the pure Z (zusammen) form, or any mixture thereof. The $(C_2-C_6)$alkenyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl.

The term "$(C_2-C_6)$alkynyl" refers to an aliphatic hydrocarbon having two to six carbon atoms and at least one carbon-carbon triple bond, including straight chains and branched chains having at least one carbon-carbon triple bond. Representative examples include, but are not limited to, ethynyl, propynyl, butynyl, pentynyl, and hexynyl. The $(C_2-C_6)$alkynyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl.

The term "$(C_1-C_6)$alkoxy" as used herein, refers to a $(C_1-C_6)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy. The $(C_1-C_6)$alkoxy can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl. For example, a $(C_1-C_6)$alkoxy can be substituted with one or more halogen atoms to form a "halo$(C_1-C_6)$alkoxy". Representative examples of a halo$(C_1-C_6)$alkoxy include, but are not limited to, fluoromethoxy, difluoromethoxy, 2-fluoroethoxy, trifluoromethoxy, and pentafluoroethoxy.

The term "$(C_1-C_6)$alkythio", as used herein, refers to a $(C_1-C_6)$alkyl group, as defined above, attached to the parent molecular moiety through a sulfur atom. Representative examples of a $(C_1-C_6)$alkylthio include, but are not limited to, methylthio, ethylthio, propylthio, and the like. The $(C_1-C_6)$alkythio can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl.

As used herein, the term "$(C_3-C_6)$cycloalkyl" refers to a carbocyclic substituent obtained by removing hydrogen from a saturated carbocyclic molecule having from 3 to 6 carbon atoms. A "cycloalkyl' may be a monocyclic ring, examples of which include cyclopropyl, cyclobutyl, cyclopentyl, and cyclohexyl. The $(C_3-C_6)$cycloalkyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl.

A "heterocycloalkyl," as used herein, refers to a cycloalkyl as defined above, wherein at least one of the ring carbon atoms is replaced with a heteroatom selected from nitrogen, oxygen or sulfur. The term "(4- to 6-membered)heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of 4 to 8 ring atoms, at least one of which is a heteroatom. A "(6-membered)heterocycloalkyl" means the heterocycloalkyl substituent contains a total of 6 ring atoms, at least one of which is a heteroatom. A "(5-membered)heterocycloalkyl" means the heterocycloalkyl substituent contains a total of 5 ring atoms at least one of which is a heteroatom. The heterocycloalkyl substituent may be attached via a nitrogen atom having the appropriate valence, or via any ring carbon atom. The heterocycloalkyl moiety may be optionally substituted with one or more substituents at a nitrogen atom having the appropriate valence, or at any available carbon atom.

Examples of heterocycloalkyl rings include, but are not limited to, azetidinyl, dihydrofuranyl, dihydrothiophenyl, tetrahydrothiophenyl, tetrahydrofuranyl, tetrahydro-triazinyl, tetrahydropyrazolyl, tetrahydrooxazinyl, tetrahydropyrimidinyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydro-oxazolyl, morpholinyl, oxetanyl, tetrahydrodiazinyl, oxazinyl, oxathiazinyl. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, 2-oxo-piperidinyl (e.g., 2-oxo-piperidin-1-yl), and the like. The heterocycloalkyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl.

A "$(C_6-C_{10})$aryl" refers to an all-carbon monocyclic or fused-ring polycyclic aromatic group having a conjugated pi-electron system containing from 6 to 10 carbon atoms, such as phenyl or naphthyl.

As used herein, the term "heteroaryl" refers to an aromatic carbocyclic system containing one, two, three or four heteroatoms selected independently from oxygen, nitrogen and sulfur and having one, two or three rings wherein such rings may be fused, wherein fused is defined above. A "(5- to 10-membered) heteroaryl" ring refers to a heteroaryl ring having from 5 to 10 ring atoms in which at least one of the ring atoms is nitrogen, with the remaining ring atoms being independently selected from the group consisting of carbon, oxygen, sulfur, and nitrogen. A "(5- to 6-membered) heteroaryl" ring refers to a heteroaryl ring having from 5 to 6 ring atoms in which at least one of the ring atoms is nitrogen, with the remaining ring atoms being independently selected from the group consisting of carbon, oxygen, sulfur, and nitrogen. Examples of heteroaryls include, but are not limited to, pyrazolyl, pyrimidinyl, pyridazinyl, thiazolyl, pyrazinyl, oxazolyl, thiadiazolyl, pyridinyl, imidazopyridinyl, triazolopyridinyl, and oxadiazolyl.

It is to be understood that the heteroaryl may be optionally fused to a cycloalkyl group, or to a heterocycloalkyl group, as defined herein.

The heteroaryl substituent may be attached via a nitrogen atom having the appropriate valence, or via any carbon atom. The heteroaryl moiety may be optionally substituted with one or more substituents at a nitrogen atom having the appropriate valence, or at any available carbon atom. The (5- to 10-membered)heteroaryl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl. The substituent can be attached to the heteroaryl moiety at any available carbon atom or to a heteroatom when the heteroatom is nitrogen having the appropriate valence.

"halo" or "halogen", as used herein, refers to a chlorine, fluorine, bromine, or iodine atom.

"hydroxy" or "hydroxyl", as used herein, means an —OH group.

"cyano", as used herein, means a —CN group, which also may be depicted:

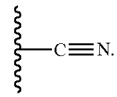

"nitro", as used herein, means an —$NO_2$ group.

"Optionally substituted", as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., —$CH_3$) is optionally substituted, then up to 3 hydrogen atoms on the carbon atom can be replaced with substituent groups.

"Patient" refers to warm-blooded animals such as, for example, pigs, cows, chickens, horses, guinea pigs, mice, rats, gerbils, cats, rabbits, dogs, monkeys, chimpanzees, and humans.

"Pharmaceutically acceptable" indicates that the substance or composition must be compatible, chemically and/or toxicologically, with the other ingredients comprising a formulation, and/or the mammal being treated therewith.

The term "therapeutically effective amount" as used herein refers to that amount of the compound (including an N-oxide thereof or a pharmaceutically acceptable salt of the compound or the N-oxide) being administered which will relieve to some extent one or more of the symptoms of the disorder being treated. In reference to the treatment of an M4-mediated disorder (e.g., Alzheimer's Disease or schizophrenia), a therapeutically effective amount refers to that amount which has the effect of relieving to some extent (or, for example, eliminating) one or more symptoms associated with the M4-mediated disorder (e.g., positive, negative, or cognitive symptom of schizophrenia; or psychotic symptom of Alzheimer's Disease).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a substituted or optionally substituted moiety is described without indicating the atom via which such moiety is bonded to a substituent, then the substituent may be bonded via any appropriate atom in such moiety. For example in an optionally substituted (5- to 10-membered) heteroaryl, a substituent on the heteroaryl can be bonded to any carbon atom on the heteroaryl part or on the heteroatom of the heteroaryl, valency permitting. Combinations of substituents and/or variables are permissible only if such combinations result in stable compounds.

This specification uses the terms "substituent," "radical," and "group" interchangeably.

If substituents are described as being "independently selected" from a group, each instance of a substituent is selected independent of any other. Each substituent therefore may be identical to or different from the other substituent(s).

As used herein the term "Formula I", "Formula I'", "Formula I$^A$", "Formula I$^B$", and "Formula I$^C$", may be hereinafter referred to as a "compound(s) of the invention." Such terms are also defined to include all forms of the compounds of the invention including, but not limited to, hydrates, solvates, isomers (including for example rotational stereoisomers), crystalline and non-crystalline forms, isomorphs, polymorphs, metabolites, prodrugs thereof. For example, the compounds of the invention, or pharmaceutically acceptable salts thereof, may exist in unsolvated and solvated forms with pharmaceutically acceptable solvents such as water, ethanol and the like. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. In general, the solvated forms are considered equivalent to the unsolvated forms for the purposes of the present invention.

The compounds of the invention may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975). Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention may exist as geometric isomers, wherein the compounds have asymmetric carbon atoms, and thus may exist as two or more stereoisomeric forms. The present invention includes all the individual stereoisomers and geometric isomers of the compounds of the invention and mixtures thereof. Individual enantiomers can be obtained by chiral separation or using the relevant enantiomer in the synthesis. The carbon-carbon bonds of the compounds of the invention may be depicted herein using a solid line (———), a solid wedge (———), or a dotted wedge (·······). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry may be marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, atropisomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

In some embodiments, the compounds of the present invention may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the present invention may also exist as an N-oxide thereof, or a pharmaceutically acceptable salt of the compound or N-oxide.

As it is known to the person skilled in the art, amine compounds (i.e., those comprising one or more nitrogen atoms), for example tertiary amines, can form N-oxides (also known as amine oxides or amine N-oxides). An N-oxide has the formula of $(R^{100}R^{200}R^{300})N^+$—$O^-$ wherein the parent amine $(R^{100}R^{200}R^{300})N$ can be for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100}R^{200}R^{300})N$ together forms 1-alkylpiperidine, 1-alkylpyrrolidine, 1-benzylpyrrolidine, or pyridine]. For instance, an imine nitrogen, especially heterocyclic or heteroaromatic imine nitrogen, or pyridine-type nitrogen

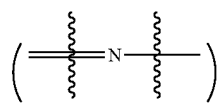

atom [such as a nitrogen atom in pyridine, pyridazine, or pyrazine], can be N-oxidized to form the N-oxide comprising the group

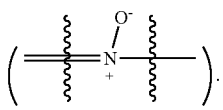

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

As noted above, the compounds of the invention (or N-oxides thereof) may exist in the form of pharmaceutically acceptable salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the present invention with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as, but not limited to, hydrochloric, hydrobromic, hydrofluoric, boric, fluoroboric, phosphoric, meta-phosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylamino-sulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanol-amine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of the invention are known to one of skill in the art.

Compounds of the invention may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

The invention also relates to prodrugs of the compounds of the present invention. Thus certain derivatives of compounds of the invention which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of the invention may themselves act as prodrugs of other compounds of the invention.

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

Also included within the scope of the invention are metabolites of compounds of the invention, that is, compounds formed in vivo upon administration of the drug.

The present invention also includes all pharmaceutically acceptable isotopically labeled compounds, which are identical to those recited herein, wherein one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of the present invention, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron-emitting isotopes, such as $^{11}$C, $^{15}$F, $^{18}$F, $^{15}$O and $^{13}$N, can be useful in positron emission tomography (PET) studies for examining substrate receptor occupancy. Isotopically labeled compounds of the present invention can generally be prepared by conventional techniques known to those skilled in the art or by processes analogous to those described in the accompanying Schemes and/or in the Examples and Preparations using an appropriate isotopically labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$. Compounds of the invention, which include compounds exemplified in Examples 1-51 described below, include isotopically labeled versions of these compounds, such as, but not limited to, the deuterated and tritiated isotopes and all other isotopes discussed above.

In certain embodiments, the present invention is directed to novel, selective, radiolabelled M4 agonists which are useful for imaging and quantifying distribution of M4 compounds in tissues (e.g., brain), using positron-emission tomography (PET).

Compounds

The compounds of Formula I, as described above, contain a piperazin-1-yl-2-azaspiro carboxylate core wherein the piperazine is attached to a 6-membered heteroaryl (pyridine or pyrazine) that is substituted with $R^1$ and with $R^2$; and the azaspiro moiety is selected from a 2-azaspiro[3.4]octane, a 6-azaspiro[3.4]octane, or a 2-azaspiro[3.3]heptane.

In one embodiment, in Formula I as described above, $X^1$ is nitrogen and $X^2$ is CH.

In another embodiment, $X^1$ is nitrogen and $X^2$ is nitrogen.

In yet another embodiment, $X^1$ is CH and $X^2$ is nitrogen.

It is to be understood that any of the above-mentioned subgenuses (embodiments) of $X^1$ and $X^2$ can be combined together with any of the subgenuses for $R^1$, $R^2$, m and n as described above and hereinafter.

In another embodiment, in Formula I as described above, $R^1$ is selected from the group consisting of halogen, cyano, $(C_1-C_6)$alkyl, $(C_1-C_6)$alkoxy, and $(C_3-C_6)$cycloalkyl, wherein said $(C_1-C_6)$alkyl, $(C_1-C_6)$alkoxy, and $(C_3-C_6)$cycloalkyl are optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and (5- to 6-membered)heteroaryl are each optionally substituted with 1 to 3 substituents selected from the group consisting of halogen, cyano, hydroxy, $(C_1-C_6)$alkyl, and $(C_1-C_6)$alkoxy.

In certain embodiments $R^1$ is a $(C_1-C_6)$alkoxy. When $R^1$ is a $(C_1-C_6)$alkoxy, the alkoxy includes, but is not limited to, methoxy, trifluoroethoxy, difluoromethoxy, and trifluoromethoxy.

In certain embodiments $R^1$ is a $(C_3-C_6)$cycloalkyl. When $R^1$ is a $(C_3-C_6)$cycloalkyl, the cycloalkyl includes, but is not limited to cyclopropyl.

In another embodiment, in Formula I as described above, $R^1$ is a (5- to 10-membered)heteroaryl selected from the group consisting of pyrazolyl, pyrimidinyl, pyridazinyl, thiazolyl, pyrazinyl, oxazolyl, thiadiazolyl, pyridinyl, imidazopyridinyl, triazolopyridinyl, and oxadiazolyl, wherein said (5- to 10-membered)heteroaryl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, —$(CH_2)_2$—O—$CH_2CH_3$, and (5- to 6-membered)heteroaryl, wherein said $(C_1-C_6)$alkyl, $(C_1-C_6)$alkoxy, and said (5- to 6-membered)heteroaryl are optionally substituted with 1 to 3 substituents selected from the group consisting of halogen, cyano, hydroxy, $(C_1-C_6)$alkyl, and $(C_1-C_6)$alkoxy.

In another embodiment, in Formula I as described above, $R^1$ is a (5- to 6-membered)heteroaryl.

When $R^1$ is a substituted (5- to 10-membered)heteroaryl or a substituted (5- to 6-membered)heteroaryl, the substituent(s) is a $(C_1-C_6)$alkyl or a $(C_1-C_6)$alkoxy, wherein the alkyl substitutent includes, but Is not limited to methyl, ethyl, cyanobutyl, and ethoxyethyl, and the alkoxy substitutent includes, but is not limited to methoxy, ethoxy, trifluoroethoxy, difluoroethoxy, and fluoromethoxy.

In another embodiment, in Formula I as described above, $R^1$ is a (4- to 8-membered)heterocycloalkyl selected from the group consisting of oxetanyl, morpholino, 2-oxa-6-azaspiro[3.3]hept-6-yl, tetrahydrofuranyl, tetrahydropyranyl, azetidinyl, pyrrolidinyl, and piperidinyl, wherein said heterocycloalkyl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and said (5- to 6-membered) heteroaryl are optionally substituted with 1 to 3 substituents selected from the group consisting of halogen, cyano, hydroxy, $(C_1-C_6)$alkyl, and $(C_1-C_6)$alkoxy.

When $R^1$ is a substituted (4- to 8-membered)heterocycloalkyl, the substituent(s) is a $(C_1-C_6)$alkyl, a $(C_1-C_6)$alkoxy or a (5- to 6-membered)heteroaryl, wherein the alkyl substitutent includes, but Is not limited to methyl, ethyl, cyanobutyl, and ethoxyethyl, the alkoxy substitutent(s) includes, but is not limited to methoxy, ethoxy, trifluoroethoxy, difluoroethoxy, and fluoromethoxy, and the (5- to 6-membered)heteroaryl substituent is a pyrazolyl, which is optionally substituted with a methyl substituent.

It is to be understood that any of the above-mentioned subgenuses (embodiments) of $R^1$ can be combined together with any of the subgenuses for $X^1$, $X^2$, $R^2$, m and n as described above and hereinafter.

In another embodiment, in Formula I as described above, $R^2$ is hydrogen.

In another embodiment, $R^2$ is fluoro.

It is to be understood that any of the above-mentioned subgenuses (embodiments) of $R^2$ can be combined together with any of the subgenuses for $X^1$, $X^2$, $R^1$, m and n as described above and hereinafter.

In another embodiment, in Formula I as described above, m is 2 and n is 1.

In another embodiment, m is 1 and n is 2.

In another embodiment, m is 1 and n is 1.

It is to be understood that any of the above-mentioned subgenuses (embodiments) of m and n can be combined together with any of the subgenuses for $X^1$, $X^2$, $R^1$, and $R^2$ as described above and hereinafter.

In certain other embodiments, the present invention is a compound of Formula $I^4$:

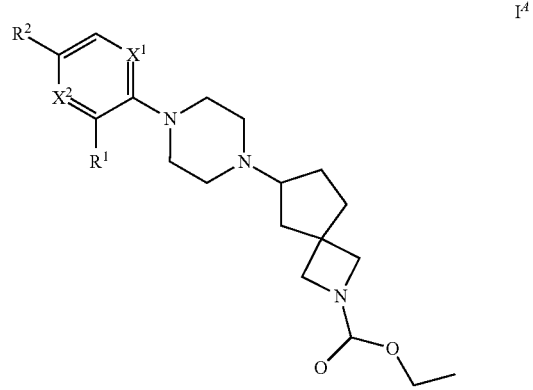

$I^4$ or an N-oxide thereof, or a pharmaceutically acceptable salt of the compound or the N-oxide, wherein:

$X^1$ and $X^2$ are each independently CH or nitrogen, provided that $X^1$ and $X^2$ cannot both be CH, $R^1$ is selected from the group consisting of halogen, cyano, $(C_1-C_6)$alkyl, $(C_1-C_6)$alkoxy, $(C_3-C_6)$cycloalkyl, —O-(4- to 6-membered)heterocycloalkyl, $(C_6-C_{10})$aryl, (5- to 10-membered)heteroaryl and (4- to 8-membered)heterocycloalkyl, wherein said $(C_1-C_6)$alkyl, $(C_1-C_6)$alkoxy, $(C_3-C_6)$cycloalkyl, —O-(4- to 6-membered)heterocycloalkyl, $(C_6-C_{10})$aryl, (5- to 10-membered)heteroaryl and (4- to 8-membered)heterocycloalkyl are optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and (5- to 6-membered)heteroaryl are optionally substituted with 1 to 3 substituents selected from the group consisting of halogen, cyano, hydroxy, $(C_1-C_6)$alkyl and $(C_1-C_6)$alkoxy; and $R^2$ is selected from the group consisting of hydrogen, halogen, $(C_1-C_6)$alkyl, and $(C_1-C_6)$alkoxy, wherein said $(C_1-C_6)$alkyl and $(C_1-C_6)$alkoxy are optionally substituted with 1 to 3 halogen.

In one embodiment, in Formula $I^A$ as described above, $X^1$ is nitrogen and $X^2$ is CH.

In another embodiment, $X^1$ is nitrogen and $X^2$ is nitrogen.

In yet another embodiment, $X^1$ is CH and $X^2$ is nitrogen.

It is to be understood that any of the above-mentioned subgenuses (embodiments) of $X^1$ and $X^2$ can be combined together with any of the subgenuses for $R^1$, $R^2$, m and n as described above and hereinafter.

In another embodiment, in Formula $I^A$ as described above, $R^1$ is selected from the group consisting of halogen, cyano, $(C_1-C_6)$alkyl, $(C_1-C_6)$alkoxy, and $(C_3-C_6)$cycloalkyl, wherein said $(C_1-C_6)$alkyl, $(C_1-C_6)$alkoxy, and $(C_3-C_6)$cycloalkyl are optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and (5- to 6-membered)heteroaryl are each optionally substituted with 1 to 3 substituents selected from the group consisting of halogen, cyano, hydroxy, $(C_1-C_6)$alkyl, and $(C_1-C_6)$alkoxy.

In certain embodiments, $R^1$ is a $(C_1-C_6)$alkoxy. When $R^7$ is a $(C_1-C_6)$alkoxy, the alkoxy includes, but is not limited to, methoxy, trifluoroethoxy, difluoromethoxy, and trifluoromethoxy.

In certain embodiments, $R^1$ is a $(C_3-C_6)$cycloalkyl. When $R^1$ is a $(C_3-C_6)$cycloalkyl, the cycloalkyl includes, but is not limited to cyclopropyl.

In another embodiment, in Formula $I^A$ as described above, $R^1$ is a (5- to 10-membered)heteroaryl selected from the group consisting of pyrazolyl, pyrimidinyl, pyridazinyl, thiazolyl, pyrazinyl, oxazolyl, thiadiazolyl, pyridinyl, imidazopyridinyl, triazolopyridinyl, and oxadiazolyl, wherein said (5- to 10-membered)heteroaryl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, —$(CH_2)_2$—O—$CH_2CH_3$, and (5- to 6-membered)heteroaryl, wherein said $(C_1-C_6)$alkyl, $(C_1-C_6)$alkoxy, and said (5- to 6-membered)heteroaryl are optionally substituted with 1 to 3 substituents selected from the group consisting of halogen, cyano, hydroxy, $(C_1-C_6)$alkyl, and $(C_1-C_6)$alkoxy.

In another embodiment, in Formula $I^A$ as described above, $R^1$ is a (5- to 6-membered)heteroaryl optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5-to 6-membered)heteroaryl, wherein said $(C_1-C_6)$alkyl, $(C_1-C_6)$alkoxy, and said (5- to 6-membered)heteroaryl are optionally substituted with 1 to 3 substituents selected from the group consisting of halogen, cyano, hydroxy, $(C_1-C_6)$alkyl, and $(C_1-C_6)$alkoxy.

When $R^1$ is a substituted (5- to 10-membered)heteroaryl or a substituted (5- to 6-membered)heteroaryl, the substituent(s) is a $(C_1-C_6)$alkyl or a $(C_1-C_6)$alkoxy, wherein the alkyl substitutent includes, but Is not limited to methyl, ethyl, cyanobutyl, and ethoxyethyl, and the alkoxy substitutent includes, but is not limited to methoxy, ethoxy, trifluoroethoxy, difluoromethoxy, and fluoromethoxy.

In another embodiment, in Formula $I^A$ as described above, $R^1$ is a (4- to 8-membered)heterocycloalkyl selected from the group consisting of oxetanyl, morpholino, 2-oxa-6-azaspiro[3.3]hept-6-yl, tetrahydrofuranyl, tetrahydropyranyl, azetidinyl, pyrrolidinyl, and piperidinyl, wherein said heterocycloalkyl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and said (5- to 6-membered) heteroaryl are optionally substituted with 1 to 3 substituents selected from the group consisting of halogen, cyano, hydroxy, $(C_1-C_6)$alkyl, and $(C_1-C_6)$alkoxy.

When $R^1$ is a substituted (4- to 8-membered)heterocycloalkyl, the substituent(s) is a $(C_1-C_6)$alkyl, a $(C_1-C_6)$alkoxy or a (5- to 6-membered)heteroaryl, wherein the alkyl substitutent includes, but Is not limited to methyl, ethyl, cyanobutyl, and ethoxyethyl, the alkoxy substitutent(s) includes, but is not limited to methoxy, ethoxy, trifluoroethoxy, difluoroethoxy, and fluoromethoxy, and the (5- to 6-membered)heteroaryl substituent is a pyrazolyl, which is optionally substituted with a methyl substituent.

It is to be understood that any of the above-mentioned subgenuses (embodiments) of $R^1$ can be combined together with any of the subgenuses for $X^1$, $X^2$, and $R^2$ as described above and hereinafter.

In another embodiment, in Formula $I^A$ as described above, $R^2$ is hydrogen.

In another embodiment, $R^2$ is fluoro.

It is to be understood that any of the above-mentioned subgenuses (embodiments) of $R^2$ can be combined together with any of the subgenuses for $X^1$, $X^2$, and $R^1$ as described above and hereinafter.

In certain other embodiments, the present invention is a compound of Formula B

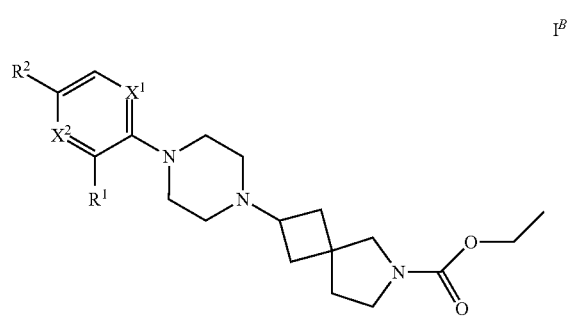

$I^B$ or an N-oxide thereof, or a pharmaceutically acceptable salt of the compound or the N-oxide, wherein:

$X^1$ and $X^2$ are each independently CH or nitrogen, provided that $X^1$ and $X^2$ cannot both be CH, $R^1$ is selected from the group consisting of halogen, cyano, $(C_1-C_6)$alkyl, $(C_1-C_6)$alkoxy, $(C_3-C_6)$cycloalkyl, —O-(4- to 6-membered)heterocycloalkyl, $(C_6-C_{10})$aryl, (5- to 10-membered)heteroaryl and (4- to 8-membered)heterocycloalkyl, wherein said $(C_1-C_6)$alkyl, $(C_1-C_6)$alkoxy, $(C_3-C_6)$cycloalkyl, —O-(4- to 6-membered)heterocycloalkyl, $(C_6-C_{10})$aryl, (5- to 10-membered)heteroaryl and (4- to 8-membered)heterocycloalkyl are optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and (5- to 6-membered)heteroaryl are optionally substituted with 1 to 3 substituents selected from the group consisting of halogen, cyano, hydroxy, ($C_1$-$C_6$)alkyl and ($C_1$-$C_6$)alkoxy;

$R^2$ is selected from the group consisting of hydrogen, halogen, ($C_1$-$C_6$)alkyl, and ($C_1$-$C_6$)alkoxy, wherein said ($C_1$-$C_6$)alkyl and ($C_1$-$C_6$)alkoxy are optionally substituted with 1 to 3 halogen.

In one embodiment, in Formula $I^B$ as described above, $X^1$ is nitrogen and $X^2$ is CH.

In another embodiment, $X^1$ is nitrogen and $X^2$ is nitrogen.

In yet another embodiment, $X^1$ is CH and $X^2$ is nitrogen.

It is to be understood that any of the above-mentioned subgenuses (embodiments) of $X^1$ and $X^2$ can be combined together with any of the subgenuses for $R^1$, $R^2$, m and n as described above and hereinafter.

In another embodiment, in Formula $I^B$ as described above, $R^1$ is selected from the group consisting of halogen, cyano, ($C_1$-$C_6$)alkyl, ($C_1$-$C_6$)alkoxy, and ($C_3$-$C_6$)cycloalkyl, wherein said ($C_1$-$C_6$)alkyl, ($C_1$-$C_6$)alkoxy, and ($C_3$-$C_6$)cycloalkyl are optionally substituted with 1 to 3 substituents selected from the group consisting of halogen, cyano, hydroxy, ($C_1$-$C_6$)alkyl, ($C_1$-$C_6$)alkoxy, ($C_3$-$C_6$)cycloalkyl, and (5- to 6-membered)heteroaryl, wherein said ($C_1$-$C_6$)alkyl, ($C_1$-$C_6$)alkoxy, and (5- to 6-membered)heteroaryl are each optionally substituted with 1 to 3 substituents selected from the group consisting of halogen, cyano, hydroxy, ($C_1$-$C_6$)alkyl, and ($C_1$-$C_6$)alkoxy.

In certain embodiments, $R^1$ is a ($C_1$-$C_6$)alkoxy. When $R^1$ is a ($C_1$-$C_6$)alkoxy, the alkoxy includes, but is not limited to, methoxy, trifluoroethoxy, difluoromethoxy, and trifluoromethoxy.

In certain embodiments, $R^1$ is a ($C_3$-$C_6$)cycloalkyl. When $R^1$ is a ($C_3$-$C_6$)cycloalkyl, the cycloalkyl includes, but is not limited to cyclopropyl.

In another embodiment, in Formula $I^B$ as described above, $R^1$ is a (5- to 10-membered)heteroaryl selected from the group consisting of pyrazolyl, pyrimidinyl, pyridazinyl, thiazolyl, pyrazinyl, oxazolyl, thiadiazolyl, pyridinyl, imidazopyridinyl, triazolopyridinyl, and oxadiazolyl, wherein said (5- to 10-membered)heteroaryl is optionally substituted with 1 to 3 substituents selected from the group consisting of halogen, cyano, hydroxy, ($C_1$-$C_6$)alkyl, ($C_1$-$C_6$)alkoxy, ($C_3$-$C_6$)cycloalkyl, and (5- to 6-membered)heteroaryl, wherein said ($C_1$-$C_6$)alkyl, ($C_1$-$C_6$)alkoxy, and said (5- to 6-membered)heteroaryl are optionally substituted with 1 to 3 substituents selected from the group consisting of halogen, cyano, hydroxy, ($C_1$-$C_6$)alkyl, and ($C_1$-$C_6$)alkoxy.

In another embodiment, in Formula $I^B$ as described above, $R^1$ is a (5- to 6-membered)heteroaryl optionally substituted with 1 to 3 substituents selected from the group consisting of halogen, cyano, hydroxy, ($C_1$-$C_6$)alkyl, ($C_1$-$C_6$)alkoxy, ($C_3$-$C_6$)cycloalkyl, and (5-to 6-membered)heteroaryl, wherein said ($C_1$-$C_6$)alkyl, ($C_1$-$C_6$)alkoxy, and said (5- to 6-membered)heteroaryl are optionally substituted with 1 to 3 substituents selected from the group consisting of halogen, cyano, hydroxy, ($C_1$-$C_6$)alkyl, and ($C_1$-$C_6$)alkoxy.

When $R^1$ is a substituted (5- to 10-membered)heteroaryl or a substituted (5- to 6-membered)heteroaryl, the substituent(s) is a ($C_1$-$C_6$)alkyl or a ($C_1$-$C_6$)alkoxy, wherein the alkyl substitutent includes, but Is not limited to methyl, ethyl, cyanobutyl, and ethoxyethyl, and the alkoxy substitutent includes, but is not limited to methoxy, ethoxy, trifluoroethoxy, difluoroethoxy, and fluoromethoxy.

In another embodiment, in Formula $I^B$ as described above, $R^1$ is a (4- to 8-membered)heterocycloalkyl selected from the group consisting of oxetanyl, morpholino, 2-oxa-6-azaspiro[3.3]hept-6-yl, tetrahydrofuranyl, tetrahydropyranyl, azetidinyl, pyrrolidinyl, and piperidinyl, wherein said heterocycloalkyl is optionally substituted with 1 to 3 substituents selected from the group consisting of halogen, cyano, hydroxy, ($C_1$-$C_6$)alkyl, ($C_1$-$C_6$)alkoxy, ($C_3$-$C_6$)cycloalkyl, and (5- to 6-membered)heteroaryl, wherein said ($C_1$-$C_6$)alkyl, and said (5-to 6-membered)heteroaryl are optionally substituted with 1 to 3 substituents selected from the group consisting of halogen, cyano, hydroxy, ($C_1$-$C_6$)alkyl, ($C_1$-$C_6$)alkoxy, and ($C_1$-$C_6$)alkoxy.

When $R^1$ is a substituted (4- to 8-membered)heterocycloalkyl, the substituent(s) is a ($C_1$-$C_6$)alkyl, a ($C_1$-$C_6$)alkoxy or a (5- to 6-membered)heteroaryl, wherein the alkyl substitutent includes, but Is not limited to methyl, ethyl, cyanobutyl, and ethoxyethyl, the alkoxy substitutent(s) includes, but is not limited to methoxy, ethoxy, trifluoroethoxy, difluoroethoxy, and fluoromethoxy, and the (5- to 6-membered)heteroaryl substituent is a pyrazolyl, which is optionally substituted with a methyl substituent.

It is to be understood that any of the above-mentioned subgenuses (embodiments) of $R^1$ can be combined together with any of the subgenuses for $X^1$, $X^2$, and $R^2$ as described above and hereinafter.

In another embodiment, in Formula $I^B$ as described above, $R^2$ is hydrogen.

In another embodiment, $R^2$ is fluoro.

It is to be understood that any of the above-mentioned subgenuses (embodiments) of $R^2$ can be combined together with any of the subgenuses for $X^1$, $X^2$, and $R^1$ as described above and hereinafter.

In certain other embodiments, the present invention is a compound of Formula $I^C$:

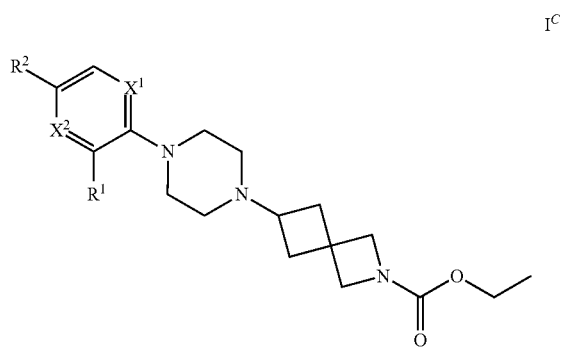

$I^C$ or an N-oxide thereof, or a pharmaceutically acceptable salt of the compound or the N-oxide, wherein:

$X^1$ and $X^2$ are each independently CH or nitrogen, provided that $X^1$ and $X^2$ cannot both be CH, $R^1$ is selected from the group consisting of halogen, cyano, ($C_1$-$C_6$)alkyl, ($C_1$-$C_6$)alkoxy, ($C_3$-$C_6$)cycloalkyl, —O-(4- to 6-membered)heterocycloalkyl, ($C_6$-$C_{10}$)aryl, (5- to 10-membered)heteroaryl and (4- to 8-membered)heterocycloalkyl, wherein said ($C_1$-$C_6$)alkyl, ($C_1$-$C_6$)alkoxy, ($C_3$-$C_6$)cycloalkyl, —O-(4- to 6-membered)heterocycloalkyl, ($C_6$-$C_{10}$)aryl, (5- to 10-membered)heteroaryl and (4- to 8-membered)heterocycloalkyl are optionally substituted with 1 to 3 substituents selected from the group consisting of halogen, cyano, hydroxy, —($C_1$-$C_6$)alkyl, ($C_1$-$C_6$)alkoxy, ($C_3$-$C_6$)cycloalkyl, and (5- to 6-membered)heteroaryl, wherein said ($C_1$-$C_6$)alkyl, ($C_1$-$C_6$)alkoxy, and (5- to 6-membered)heteroaryl are optionally substituted with 1 to 3 substituents selected from the group consisting of halogen, cyano, hydroxy, $(C_1-C_6)$alkyl and $(C_1-C_6)$alkoxy; and $R^2$ is selected from the group consisting of hydrogen, halogen, $(C_1-C_6)$alkyl, and $(C_1-C_6)$alkoxy, wherein said $(C_1-C_6)$alkyl and $(C_1-C_6)$alkoxy are optionally substituted with 1 to 3 halogen.

In one embodiment, in Formula $I^C$ as described above, $X^1$ is nitrogen and $X^2$ is CH.

In another embodiment, $X^1$ is nitrogen and $X^2$ is nitrogen.

In yet another embodiment, $X^1$ is CH and $X^2$ is nitrogen.

It is to be understood that any of the above-mentioned subgenuses (embodiments) of $X^1$ and $X^2$ can be combined together with any of the subgenuses for $R^1$, and $R^2$ as described above and hereinafter.

In another embodiment, in Formula $I^C$ as described above, $R^1$ is selected from the group consisting of halogen, cyano, $(C_1-C_6)$alkyl, $(C_1-C_6)$alkoxy, and $(C_3-C_6)$cycloalkyl, wherein said $(C_1-C_6)$alkyl, $(C_1-C_6)$alkoxy, and $(C_3-C_6)$cycloalkyl are optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and (5- to 6-membered)heteroaryl are each optionally substituted with 1 to 3 substituents selected from the group consisting of halogen, cyano, hydroxy, $(C_1-C_6)$alkyl, and $(C_1-C_6)$alkoxy.

In certain embodiments, $R^1$ is a $(C_1-C_6)$alkoxy. When $R^1$ is a $(C_1-C_6)$alkoxy, the alkoxy includes, but is not limited to, methoxy, trifluoroethoxy, difluoromethoxy, and trifluoromethoxy.

In certain embodiments, $R^1$ is a $(C_3-C_6)$cycloalkyl. When $R^1$ is a $(C_3-C_6)$cycloalkyl, the cycloalkyl includes, but is not limited to cyclopropyl.

In another embodiment, in Formula $I^C$ as described above, $R^1$ is a (5- to 10-membered)heteroaryl selected from the group consisting of pyrazolyl, pyrimidinyl, pyridazinyl, thiazolyl, pyrazinyl, oxazolyl, thiadiazolyl, pyridinyl, imidazopyridinyl, triazolopyridinyl, and oxadiazolyl, wherein said (5- to 10-membered)heteroaryl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, —$(CH_2)_2$—O—$CH_2CH_3$, and (5- to 6-membered)heteroaryl, wherein said $(C_1-C_6)$alkyl, $(C_1-C_6)$alkoxy, and said (5- to 6-membered)heteroaryl are optionally substituted with 1 to 3 substituents selected from the group consisting of halogen, cyano, hydroxy, $(C_1-C_6)$alkyl, and $(C_1-C_6)$alkoxy.

In another embodiment, in Formula $I^C$ as described above, $R^1$ is a (5- to 6-membered)heteroaryl optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5-to 6-membered)heteroaryl, wherein said $(C_1-C_6)$alkyl, $(C_1-C_6)$alkoxy, and said (5- to 6-membered)heteroaryl are optionally substituted with 1 to 3 substituents selected from the group consisting of halogen, cyano, hydroxy, $(C_1-C_6)$alkyl, and $(C_1-C_6)$alkoxy.

When $R^1$ is a substituted (5- to 10-membered)heteroaryl or a substituted (5- to 6-membered)heteroaryl, the substituent(s) is a $(C_1-C_6)$alkyl or a $(C_1-C_6)$alkoxy, wherein the alkyl substitutent includes, but Is not limited to methyl, ethyl, cyanobutyl, and ethoxyethyl, and the alkoxy substitutent includes, but is not limited to methoxy, ethoxy, trifluoroethoxy, difluoroethoxy, and fluoromethoxy.

In another embodiment, in Formula $I^C$ as described above, $R^1$ is a (4- to 8-membered)heterocycloalkyl selected from the group consisting of oxetanyl, morpholino, 2-oxa-6-azaspiro[3.3]hept-6-yl, tetrahydrofuranyl, tetrahydropyranyl, azetidinyl, pyrrolidinyl, and piperidinyl, wherein said heterocycloalkyl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and said (5- to 6-membered) heteroaryl are optionally substituted with 1 to 3 substituents selected from the group consisting of halogen, cyano, hydroxy, $(C_1-C_6)$alkyl, and $(C_1-C_6)$alkoxy.

When $R^1$ is a substituted (4- to 8-membered)heterocycloalkyl, the substituent(s) is a $(C_1-C_6)$alkyl, a $(C_1-C_6)$alkoxy or a (5- to 6-membered)heteroaryl, wherein the alkyl substitutent includes, but Is not limited to methyl, ethyl, cyanobutyl, and ethoxyethyl, the alkoxy substitutent(s) includes, but is not limited to methoxy, ethoxy, trifluoroethoxy, difluoroethoxy, and fluoromethoxy, and the (5- to 6-membered)heteroaryl substituent is a pyrazolyl, which is optionally substituted with a methyl substituent.

It is to be understood that any of the above-mentioned subgenuses (embodiments) of $R^1$ can be combined together with any of the subgenuses for $X^1$, $X^2$, and $R^2$ as described above and hereinafter.

In another embodiment, in Formula $I^C$ as described above, $R^2$ is hydrogen.

In another embodiment, $R^2$ is fluoro.

It is to be understood that any of the above-mentioned subgenuses (embodiments) of $R^2$ can be combined together with any of the subgenuses for $X^1$, $X^2$, and $R^1$ as described above and hereinafter.

In certain other embodiments, the present invention is a compound of Formula I':

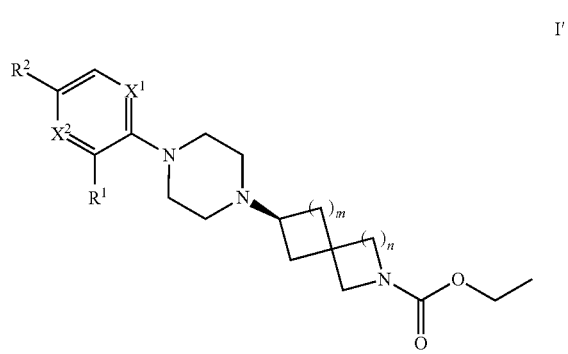

I' or an N-oxide thereof, or a pharmaceutically acceptable salt of the compound or the N-oxide, wherein:

$X^1$ and $X^2$ are each independently CH or nitrogen, provided that $X^1$ and $X^2$ cannot both be CH, $R^1$ is selected from the group consisting of halogen, cyano, $(C_1-C_6)$alkyl, $(C_1-C_6)$alkoxy, $(C_3-C_6)$cycloalkyl, —O-(4- to 6-membered)heterocycloalkyl, $(C_6-C_{10})$aryl, (5- to 10-membered)heteroaryl and (4- to 8-membered)heterocycloalkyl, wherein said $(C_1-C_6)$alkyl, $(C_1-C_6)$alkoxy, $(C_3-C_6)$cycloalkyl, —O-(4- to 6-membered)heterocycloalkyl, $(C_6-C_{10})$aryl, (5- to 10-membered)heteroaryl and (4- to 8-membered)heterocycloalkyl are optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and (5- to 6-membered)heteroaryl are optionally substituted with 1 to 3 substituents selected from the group consisting of halogen, cyano, hydroxy, $(C_1-C_6)$alkyl and $(C_1-C_6)$alkoxy;

$R^2$ is selected from the group consisting of hydrogen, halogen, $(C_1-C_6)$alkyl, and $(C_1-C_6)$alkoxy, wherein said $(C_1-C_6)$alkyl and $(C_1-C_6)$alkoxy are optionally substituted with 1 to 3 halogen;

m is 1 or 2; and n is 1 or 2.

In one embodiment, in Formula I' as described above, $X^1$ is nitrogen and $X^2$ is CH.

In another embodiment, $X^1$ is nitrogen and $X^2$ is nitrogen.

In yet another embodiment, $X^1$ is CH and $X^2$ is nitrogen.

It is to be understood that any of the above-mentioned subgenuses (embodiments) of $X^1$ and $X^2$ can be combined together with any of the subgenuses for $R^1$, $R^2$, m and n as described above and hereinafter.

In another embodiment, in Formula I' as described above, $R^1$ is selected from the group consisting of halogen, cyano, $(C_1-C_6)$alkyl, $(C_1-C_6)$alkoxy, and $(C_3-C_6)$cycloalkyl, wherein said $(C_1-C_6)$alkyl, $(C_1-C_6)$alkoxy, and $(C_3-C_6)$cycloalkyl are optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl, $(C_1-C_6)$alkoxy, and (5- to 6-membered)heteroaryl are each optionally substituted with 1 to 3 substituents selected from the group consisting of halogen, cyano, hydroxy, $(C_1-C_6)$alkyl, and $(C_1-C_6)$alkoxy.

In certain embodiments, $R^1$ is a $(C_1-C_6)$alkoxy. When $R^1$ is a $(C_1-C_6)$alkoxy, the alkoxy includes, but is not limited to, methoxy, trifluoroethoxy, difluoromethoxy, and trifluoromethoxy.

In certain embodiments, $R^1$ is a $(C_3-C_6)$cycloalkyl. When $R^1$ is a $(C_3-C_6)$cycloalkyl, the cycloalkyl includes, but is not limited to cyclopropyl.

In another embodiment, in Formula I' as described above, $R^1$ is a (5- to 10-membered)heteroaryl selected from the group consisting of pyrazolyl, pyrimidinyl, pyridazinyl, thiazolyl, pyrazinyl, oxazolyl, thiadiazolyl, pyridinyl, imidazopyridinyl, triazolopyridinyl, and oxadiazolyl, wherein said (5- to 10-membered)heteroaryl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, —$(CH_2)_2$—O—$CH_2CH_3$, and (5- to 6-membered)heteroaryl, wherein said $(C_1-C_6)$alkyl, $(C_1-C_6)$alkoxy, and said (5- to 6-membered)heteroaryl are optionally substituted with 1 to 3 substituents selected from the group consisting of halogen, cyano, hydroxy, $(C_1-C_6)$alkyl, and $(C_1-C_6)$alkoxy.

In another embodiment, in Formula I' as described above, $R^1$ is a (5- to 6-membered)heteroaryl optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5-to 6-membered)heteroaryl, wherein said $(C_1-C_6)$alkyl, $(C_1-C_6)$alkoxy, and said (5- to 6-membered)heteroaryl are optionally substituted with 1 to 3 substituents selected from the group consisting of halogen, cyano, hydroxy, $(C_1-C_6)$alkyl, and $(C_1-C_6)$alkoxy.

When $R^1$ is a substituted (5- to 10-membered)heteroaryl or a substituted (5- to 6-membered)heteroaryl, the substituent is a $(C_1-C_6)$alkyl or a $(C_1-C_6)$alkoxy, wherein the alkyl substitutent includes, but Is not limited to methyl, ethyl, cyanobutyl, and ethoxyethyl, and the alkoxy substitutent(s) includes, but is not limited to methoxy, ethoxy, trifluoroethoxy, difluoroethoxy, and fluoromethoxy.

In another embodiment, in Formula I' as described above, $R^1$ is a (4- to 8-membered)heterocycloalkyl selected from the group consisting of oxetanyl, morpholino, 2-oxa-6-azaspiro[3.3]hept-6-yl, tetrahydrofuranyl, tetrahydropyranyl, azetidinyl, pyrrolidinyl, and piperidinyl, wherein said heterocycloalkyl is optionally substituted with 1 to 3 substituents selected from the group consisting of halogen, cyano, hydroxy, $(C_1-C_6)$alkyl, $(C_1-C_6)$alkoxy, $(C_3-C_6)$cycloalkyl, and (5- to 6-membered)heteroaryl, wherein said $(C_1-C_6)$alkyl and said (5-to 6-membered)heteroaryl are optionally substituted with 1 to 3 substituents selected from the group consisting of halogen, cyano, hydroxy, $(C_1-C_6)$alkyl, and $(C_1-C_6)$alkoxy.

When $R^1$ is a substituted (4- to 8-membered)heterocycloalkyl, the substituent(s) is a $(C_1-C_6)$alkyl, a $(C_1-C_6)$alkoxy or a (5- to 6-membered)heteroaryl, wherein the alkyl substitutent includes, but Is not limited to methyl, ethyl, cyanobutyl, and ethoxyethyl, the alkoxy substitutent(s) includes, but is not limited to methoxy, ethoxy, trifluoroethoxy, difluoroethoxy, and fluoromethoxy, and the (5- to 6-membered)heteroaryl substituent is a pyrazolyl, which is optionally substituted with a methyl substituent.

It is to be understood that any of the above-mentioned subgenuses (embodiments) of $R^1$ can be combined together with any of the subgenuses for $X^1$, $X^2$, $R^2$, m and n as described above and hereinafter.

In another embodiment, in Formula I' as described above, $R^2$ is hydrogen.

In another embodiment, $R^2$ is fluoro.

It is to be understood that any of the above-mentioned subgenuses (embodiments) of $R^2$ can be combined together with any of the subgenuses for $X^1$, $X^2$, $R^1$, m and n as described above and hereinafter.

In another embodiment, in Formula I' as described above, m is 2 and n is 1.

In another embodiment, m is 1 and n is 2.

In another embodiment, m is 1 and n is 1.

It is to be understood that any of the above-mentioned subgenuses (embodiments) of m and n can be combined together with any of the subgenuses for $X^1$, $X^2$, $R^1$, and $R^2$ as described above and hereinafter.

In certain other embodiments, the present invention is directed to the use of the compounds, or N-oxide, or pharmaceutically acceptable salt of any one the compounds of the present invention in the treatment of an M4-mediated (or M4-associated) disease or disorder.

In certain other embodiments, the present invention is directed to a method for treating an M4-mediated (or M4-associated) disease or disorder in a patient, said method comprising administering to the patient a therapeutically effective amount of a compound, or N-oxide, or pharmaceutically acceptable salt of any one the compounds of the present invention.

In certain embodiments, the compounds of the present invention are M4 receptor agonists, wherein the compound has a binding affinity for and induces an effect on the M4 receptor absent the presence of a native ligand (e.g. acetylcholine).

In certain other embodiments, the present invention is directed to the use mentioned above wherein the M4-mediated (or M4-associated) disease or disorder is a disease or disorder selected from the group consisting of Alzheimer's Disease, schizophrenia, pain, addiction, a sleep disorder, a cognitive disorder (e.g. mild cognitive impairment, age-related mild cognitive impairment, and amnestic mild cognitive impairment), Parkinson's Disease, Parkinson's Disease Levodopa-Induced Dyskinesia (PD-LID), Huntington's Disease, dyskinesia, dry mouth, pulmonary hypertension, chronic obstructive pulmonary disease (COPD), asthma, urinary incontinence, glaucoma, Trisomy 21 (Down Syndrome), cerebral amyloid angiopathy, dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis.

In certain embodiments, the M4-mediated (or M4-associated) disease or disorder is a disease or disorder selected from the group consisting of Alzheimer's Disease, Parkinson's Disease, Huntington's Disease, schizophrenia, pain, addiction, and a sleep disorder.

The present invention also provides compositions (e.g., pharmaceutical compositions) comprising a novel compound of the present invention. Accordingly, in one embodiment, the invention provides a pharmaceutical composition comprising (a therapeutically effective amount of) a novel compound of the present invention and optionally comprising a pharmaceutically acceptable carrier. In one further embodiment, the invention provides a pharmaceutical composition comprising (a therapeutically effective amount of) a compound of the invention, optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

Pharmacology

The muscarinic acetylcholine receptor M4 (also known as muscarinic 4 or CHRM4) is a protein in humans that is encoded for the CHRM4 gene. M4 receptors are predominantly expressed in the brain. Key regions of the brain where M4 receptor expression occurs are the striatum, cortex, and hippocampus with the highest expression occurring in the striatum (approx. 46%) where M4 is the major muscarinic subtype. M4 is sporadically expressed in the periphery (e.g., testis, skin and colon).

M4 receptors are coupled to $G_{q/i}$ proteins and function as inhibitory autoreceptors in the striatum and midbrain (Zhang et al. 2002; Tzavara et al. 2004), and as postsynaptic modulatory receptors in the striatum, neocortex and hippocampus (Levy et al. 1991; Zhang et al. 1997). M4 receptors are also found presynaptically on glutamatergic synapses from cortex to striatum (Pancani, T., et al., "Allosteric activation of M4 improve behavioral and physiological alterations in early symptomatic YAC128 mice", Proceedings of the National Academy of the Sciences of the United States of America, 2015 Nov. 10; 112(45):14078-83), and on hippocampal glutamate neurons (where presynaptic M4 modulates glutamate release. The highest expression of M4 receptors is found in the striatum, M4 receptors also possess a regulatory effect on dopaminergic neurotransmission, and are coexpressed with D1 dopamine receptors in a subset of striatal medium spiny neurons which contain GABA as a major neurotransmitter (Bernard et al. 1992; Di Chiara et al. 1994; Ince et al. 1997).

It has been hypothesized that administration of a selective M4 agonist would provide antipsychotic activity for the treatment of schizophrenia (Felder et al. "Elucidating the Role of Muscarinic Receptors in Psychosis", Life Sci. 68:2605-2613, 2001). This belief was further supported by studies that demonstrated M4 receptors modulate the dynamics of dopaminergic and cholinergic neurotransmission and that a state of dopamine hyperfunctions results with a loss of M4 function (Tzavara et al., "M4 Muscarinic Receptors Regulate the Dynamics of Cholinergic and Dopaminergic Neurotransmission: relevance to the pathophysiology and treatment of related CNS pathologies" FASEB J. 18:1410-1412, 2004).

The compounds of the present invention may also be useful for treating/alleviating the neuropsychiatric symptoms (i.e., behavioral symptoms) associated with Alzheimer's Disease and Schizophrenia (Foster, Daniel J. et. al., "Activation of M1 and M4 muscarinic receptors as potential treatments for Alzheimer's disease and schizophrenia", Neuropsychiatric Disease and Treatment, Volume 2014:10, pp. 183-191). These behavioral symptoms include, but are not limited to, agitation, anxiety, irritability, combativeness, disorientation, illusion, delusion, apathy, depression, disinhibition, aberrant motor and obsessive-compulsive behaviors, as well as sleep disorders (Dillon, Carol, et. al. "Behavioral symptoms related to cognitive impairment", Neuropsychiatric Disease and Treatment 2013:9 1443-1455). By treating/alleviating the above-mentioned behavioral symptoms, it is believed that the compounds of the present invention will also enhance cognition.

In view of the above, the compounds of the present invention may be useful for the treatment of schizophrenia and Alzheimer's Disease. The compounds of the present invention may also be useful for the treatment of Parkinson's Disease, Huntington's Disease, addiction, depression and epilepsy.

It is believed the M4 selective activators of the present invention may also have a wide range of other therapeutic applications for the treatment of conditions or diseases of the central nervous system which include neurologic, neurodegenerative and/or psychiatric disorders. Neurologic, neurodegenerative and/or psychiatric disorders include but are not limited to, (1) mood [affective] disorders; (2) neurotic, stress-related and somatoform disorders including anxiety disorders; (3) disorders comprising the symptom of cognitive deficiency in a mammal, including a human; (4) disorders comprising attention deficits, executive function deficits (working memory deficits), dysfunction of impulse control, extrapyramidal symptoms, disorders that are based on a malfunction of basal ganglia, hippocampus and prefrontal cortex; (5) behavioral and emotional disorders with onset usually occurring in childhood and adolescence; (6) disorders of psychological development; (7) systemic atrophies primarily affecting the central nervous system; (8) extrapyramidal and movement disorders; (9) behavioral syndromes associated with physiological disturbances and physical factors; (10) disorders of adult personality and behavior; (11) schizophrenia and other psychotic disorders; (12) mental and behavioral disorders due to psychoactive substance use; (13) sexual dysfunction comprising excessive sexual drive; (14) mental retardation; (15) factitious disorders, e.g., acute hallucinatory mania; (16) episodic and paroxysmal disorders, epilepsy; (17) narcolepsy; (18) dementia, and (19) amyotrophic lateral sclerosis.

Examples of mood [affective] disorders that can be treated according to the present invention include, but are not limited to, bipolar disorder I, hypomania (manic and mixed form), bipolar disorder II; depressive disorders such as single depressive episode or recurrent major depressive disorder, chronic depression, psychotic depression, minor depressive disorder, depressive disorder with postpartum onset, depressive disorders with psychotic symptoms; persistent mood [affective] disorders such as cyclothymia, dysthymia, euthymia; premenstrual syndrome (PMS) and premenstrual dysphoric disorder.

Examples of neurotic, stress-related and somatoform disorders that can be treated according to the present invention include, but are not limited to, anxiety disorders, social anxiety disorder, general anxiety disorder, panic disorder with or without agoraphobia, specific phobia, social phobia, chronic anxiety disorders; obsessive compulsive disorder; reaction to severe stress and adjustment disorders, such as post-traumatic stress disorder (PTSD), acute stress disorder; other neurotic disorders such as depersonalization-derealization syndrome.

The phrase "cognitive deficiency" as used herein and "disorders comprising the symptom of cognitive deficiency" refers to a subnormal functioning or a suboptimal functioning in one or more cognitive aspects such as memory, intellect, learning and logic ability, or attention and executive function (working memory) in a particular individual comparative to other individuals within the same general age population.

Examples of "disorders comprising the symptom of cognitive deficiency" that can be treated according to the present invention include, but are not limited to, cognitive deficits primarily but not exclusively related to amnesia, psychosis (schizophrenia), Parkinson's disease, Alzheimer's Disease, multi-infarct dementia, senile dementia, Lewis body dementia, stroke, frontotemporal dementia, progressive supranuclear palsy, Huntington's disease, HIV disease (HIV-associated dementia), cerebral trauma and drug abuse; mild cognitive disorder ADHD, Asperger's syndrome, and age-associated memory impairment; cognitive decline or delerium post-operative or in association with intensive care therapy.

Examples of disorders usually first diagnosed in infancy, childhood and adolescence that can be treated according to the present invention include, but are not limited to, hyperkinetic disorders including disturbance of activity and attention, attention deficit/hyperactivity disorder (ADHD), hyperkinetic conduct disorder; attention deficit disorder (ADD); conduct disorders, including but not limited to depressive conduct disorder; tic disorders including transient tic disorder, chronic motor or vocal tic disorder, combined vocal and multiple motor tic disorder (Gilles de la Tourette's syndrome), substance-induced tic disorders; autistic disorders; Batten disease, excessive masturbation, nail-biting, nose-picking and thumb-sucking.

Examples of disorders of psychological development that can be treated according to the present invention include, but are not limited to pervasive developmental disorders, including but not limited to Asperger's syndrome and Rett syndrome, autistic disorders, childhood autism and overactive disorder associated with mental retardation and stereotyped movements, specific developmental disorder of motor function, specific developmental disorders of scholastic skills.

Examples of systemic atrophies primarily affecting the central nervous system that can be treated according to the present invention include, but are not limited to, multiple sclerosis systemic atrophies primarily affecting the basal ganglia including Huntington's disease, and amyotrophic lateral sclerosis.

Examples of extrapyramidal and movement disorders with malfunction and/or degeneration of basal ganglia that can be treated according to the present invention include, but are not limited to, Huntington's disease; Parkinson's disease; second Parkinsonism such as postencephalitic Parkinsonism; Parkinsonism comprised in other disorders; Niemann-Pick disease, Lewy body disease; degenerative diseases of the basal ganglia; other extrapyramidal and movement disorders including tremor, essential tremor and drug-induced tremor, myoclonus, chorea and drug-induced chorea, drug-induced tics and tics of organic origin, drug-induced acute dystonia, drug-induced tardive dyskinesia, muscular spasms and disorders associated with muscular spasticity or weakness including tremors; mental deficiency (including spasticity, Down syndrome and fragile X syndrome), L-dopa-induced dyskinesia; restless leg syndrome and Stiff-man syndrome.

Further examples of movement disorders with malfunction and/or degeneration of basal ganglia that can be treated according to the present invention include, but are not limited to, dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), or mandibular dystonia and spasmodic dysphonia (cramp of the vocal cord); neuroleptic-induced movement disorders including but not limited to neuroleptic malignant syndrome (NMS), neuroleptic-induced Parkinsonism, neuroleptic-induced early onset or acute dyskinesia, neuroleptic-induced acute dystonia, neuroleptic-induced acute akathisia, neuroleptic-induced tardive dyskinesia, and neuroleptic-induced tremor.

Examples of behavioral syndromes associated with physiological disturbances and physical factors according to the present invention include, but are not limited to, nonorganic sleep disorders, including but not limited to nonorganic hypersomnia, nonorganic disorder of the sleep-wake schedule (circadian rhythm sleep disorder), insomnia, parasomnia and sleep deprivation; mental and behavioral disorders associated with the puerperium including postnatal and postpartum depression; eating disorders, including but not limited to anorexia nervosa, bulimia nervosa, binge eating disorder, hyperphagia, obesity, compulsive eating disorders and pagophagia.

Examples of disorders of adult personality and behavior that can be treated according to the present invention include, but are not limited to, personality disorders, including but not limited to emotionally unstable, borderline, obsessive-compulsive, anankastic, dependent and passive-aggressive personality disorder; habit and impulse disorders (impulse-control disorder) including intermittent explosive disorder, pathological gambling, pathological fire-setting (pyromania), pathological stealing (kleptomania), trichotillomania; Munchausen syndrome.

Examples of schizophrenia and other psychotic disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis such as social withdrawal in schizophrenia.

Examples of mental and behavioral disorders due to psychoactive substance use that can be treated according to the present invention include, but are not limited to, mental and behavioral disorders due to use of alcohol, opioids, cannabinoids, sedatives or hypnotics, cocaine; mental and behavioral disorders due to the use of other stimulants including caffeine, mental and behavioral disorders due to drug dependence and abuse (e.g., narcotic dependence, alcoholism, amphetamine and methamphetamine dependence, opioid dependence, cocaine addiction, nicotine dependence, and drug withdrawal syndrome, and relapse prevention), use of hallucinogens, tobacco (nicotine), volatile solvents and mental and behavioral disorders due to multiple drug use and use of other psychoactive substances including the following subtype symptoms: harmful use, dependence syndrome, withdrawal state, and withdrawal state with delirium.

Examples of dementia that can be treated according to the present invention include, but are not limited to, vascular dementia, dementia due to Creutzfeld-Jacob disease, HIV, head trauma, Parkinson's, Huntington's, Pick's disease, dementia of the Alzheimer's type.

In certain embodiments, the present invention is directed to the use of the compounds of the present invention for the treatment of schizophrenia by administration of a therapeutically effective amount of a compound of the present invention to a patient in need thereof.

In certain other embodiments, the invention is further directed to the use of the compounds of the present invention for the treatment of cognitive impairment associated with schizophrenia by administration of a therapeutically effective amount of a compound of the present invention to a patient in need thereof.

Schizophrenia or psychosis for which the compounds, N-oxide thereof, and pharmaceutically acceptable salts of the foregoing of the invention may be useful includes one or more of the following conditions: schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthesia, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's Disease and post-traumatic stress syndrome), including both the positive and the negative symptoms of schizophrenia and other psychoses; cognitive disorders including dementia (associated with Alzheimer's Disease, ischemia, multi-infarct dementia, trauma, vascular problems or stroke, HIV disease, Parkinson's disease, Huntington's disease, Pick's disease, Creutzfeldt-Jakob disease, perinatal hypoxia, other general medical conditions or substance abuse); delirium, amnestic disorders, or age related cognitive decline.

In addition to the central nervous system disorders mentioned above, the compounds of the present invention may be used to treat other M4-mediated (or M4-associated) disorders such as, but not limited to, addiction (e.g. substance addiction such as addiction to opioids, cocaine, or alcohol), pain (e.g. acute pain, inflammatory pain, and neuropathic pain), and a sleep disorder (such as those related to REM sleep regulation, for example, those related to REM sleep onset). Additional M4-mediated (or M4-associated) disorders or conditions that may be treated by the compounds of the invention include, dry mouth, a cognitive disorder (e.g. mild cognitive impairment), dyskinesia, pulmonary hypertension, chronic obstructive pulmonary disease (COPD), asthma, urinary incontinence, glaucoma, Trisomy 21 (Down Syndrome), cerebral amyloid angiopathy, dementia (e.g. degenerative dementia), Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, and atherosclerosis. See e.g. U.S. Pat. No. 8,664,234.

Potential sleep disorders for which the compounds, N-oxide thereof, and pharmaceutically acceptable salts of the foregoing of the invention may be useful include: enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds, N-oxide thereof, and pharmaceutically acceptable salts of the foregoing of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, tenosynovitis and gout), headache, migraine and cluster headache, headache, primary hyperalgesia, secondary hyperalgesia, primary allodynia, secondary allodynia, or other pain caused by central sensitization.

The compounds, N-oxides thereof, and pharmaceutically acceptable salts of the foregoing of the invention may be used to decrease tolerance and/or dependence to opioid treatment of pain, and for treatment of withdrawal syndrome of e.g., alcohol, opioids, and cocaine.

Formulations

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be formulated such that administration topically to the skin or mucosa (i.e., dermally or transdermally) leads to systemic absorption of the compound. In another embodiment, the compounds of the invention can also be formulated such that administration intranasally or by inhalation leads to systemic absorption of the compound. In another embodiment, the compounds of the invention may be formulated such that administration rectally or vaginally leads to systemic absorption of the compound.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically (e.g., intranasal or ophthalmic).

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents, and include depot formulations.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of an M4 activator compound of the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-ß (or fragments thereof), such as $Aß_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-ß (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or-inhibiting agents (including those that reduce amyloid production, accumulation and fibrillization) such as dimebon, davunetide, eprodisate, leuprolide, SK—PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W [3,5-bis(4-nitrophenoxy)benzoic acid], NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topiramate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxapine, risperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrolidin-1-ylmethyl)phenyl]-cyclobutanecarboxamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURINETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecyl-2H-pyrrol-2-ylidene)methyl]-1H,1'H-2,2'-bipyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (1-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, riluzole, N-hydroxy-1,2,4,9-tetrahydro-3H-carbazol-3-imine, desmoteplase, anatibant, astaxanthin, neuropeptide NAP (e.g., AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-ß-hydroxyepiandrosterone; Newron Pharmaceuticals), HF-0420 (also known as oligotropin), pyridoxal 5'-phosphate (also known as MC-1), microplasmin, S-18986, piclozotan, NPO31112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitors such as 2-({4-[1-methyl-4-(pyridin-4-yl)-1H-pyrazol-3-yl]phenoxy}methyl)quinolin-3(4H)-one and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, Ac-rER ($N^2$-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[(2S)-3-ethyl-1-hydroxypentan-2-yl]benzenesulfonamide;

(xxxiii) serotonin (5-hydroxytryptamine) 1A (5-$HT_{1A}$) receptor antagonists, such as spiperone, levo-pindolol, BMY 7378, NAD-299, S—(-)—UH-301, NAN 190, lecozotan;

(xxxiv) serotonin (5-hydroxytryptamine) 2C (5-$HT_{2C}$) receptor agonists, such as vabicaserin and zicronapine;

(xxxv) serotonin (5-hydroxytryptamine) 4 (5-$HT_4$) receptor agonists, such as PRX-03140 (Epix);

(xxxvi) serotonin (5-hydroxytryptamine) 6 (5-$HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydro-furan-3-yl}propane-2-sulfonamide, and the like.

(xli) Janus kinase inhibitors (JAK) such as, but not limited to, tofacitinib, ruxolitinib, baricitinib, CYT387, GLPG0634, lestaurtinib, pacritinib, and TG101348.

(xlii) Interleukin-1 receptor-associated kinase 4 inhibitors (IRAK4) such as, but not limited to, PF-06650833.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

As noted above, the compounds of the present invention may be used in combination with one or more additional anti-schizophrenia agents which are described herein. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention (or an N-oxide thereof or a pharmaceutically acceptable salt of the foregoing).

The invention also provides a pharmaceutical composition for the treatment of schizophrenia in a mammal, including a human, which comprises an amount of a compound of the present invention (including an N-oxide thereof or a salt of the compound or the N-oxide), as defined above (including hydrates, solvates and polymorphs of said compound or pharmaceutically acceptable salts thereof), in combination with one or more (for example one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

The invention also provides a pharmaceutical composition for treating an M4-mediated (or M4-associated) disease or disorder in a mammal, including a human, which comprises an amount of a compound of the present invention (including an N-oxide thereof or a salt of the compound or the N-oxide), as defined above (including hydrates, solvates and polymorphs of said compound N-oxide or a pharmaceutically acceptable salt of the foregoing), in combination with one or more (for example one to three) other agents for treating the M4-mediated (or M4-associated) disease or disorder, wherein the amount of the active agents and the combination when taken as a whole are therapeutically effective for treating the M4-mediated (or M4-associated) disease or disorder.

It will be understood that the compounds of the present invention depicted above (Formula I, Formula Ia and Formula Ib) are not limited to a particular stereoisomer (e.g. enantiomer or atropisomer) shown, but also include all stereoisomers and mixtures thereof.

General Schemes

The compounds of Formula I, $I^A$ B $I^C$, and I' may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XIII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, $I^A$, $I^B$, $I^C$, and I' or their pharmaceutically acceptable salts, can be prepared according to the reaction Schemes discussed herein below. Unless otherwise indicated, the substituents in the Schemes are defined as above. For example, in Formula $I^A$ m is 2 and n is 1. In Formula $I^B$ m is 1 and n is 2. In Formula $I^C$ m and n are both 1. Isolation and purification of the products is accomplished by standard procedures, which are known to a chemist of ordinary skill.

It will be understood by one skilled in the art that the various symbols, superscripts, and subscripts used in the schemes, methods, and examples are used for convenience of representation and/or to reflect the order in which they are introduced in the schemes, and are not intended to necessarily correspond to the symbols, superscripts, or subscripts in the appended claims. Additionally, one skilled in the art will recognize that in many cases, these compounds will be mixtures and enantiomers that may be separated at various

Scheme 1

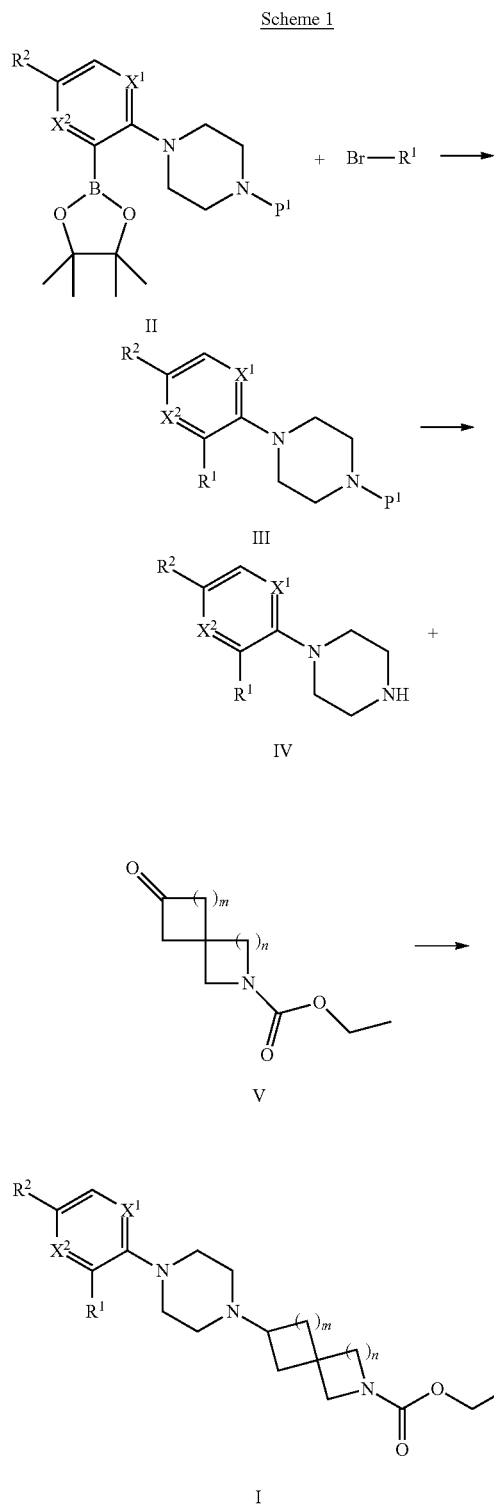

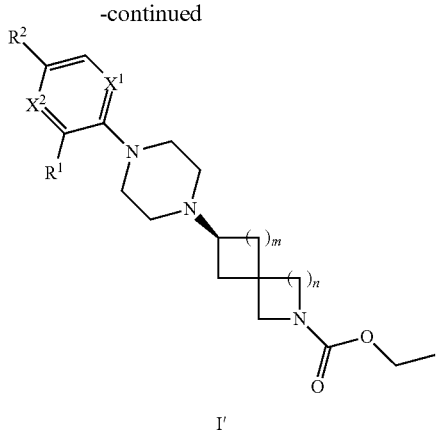

Scheme 1 refers to one synthetic sequence for the preparation of compounds of Formula I. Referring to scheme 1, compound II can be coupled to a heteroaryl bromide, wherein the $X^1$, $X^2$, and $R^2$ substituents of Formula II should be represented by the same moieties as desired in the final product or protected variation thereof, and $R^1$ refers to an aryl or 5- or 6-membered heteroaryl, to produce compound III via a palladium-catalyzed Suzuki coupling reaction using a standard selection of palladium source, ligand, and base, in a standard solvent, for example but not limited to acetonitrile, toluene, or ethanol. Examples of the Pd/ligand/base combination include but are not limited to tetrakis(triphenylphosphine)palladium(0) plus sodium carbonate and tris(dibenzylideneacetone)dipalladium(0) plus dicyclohexylphosphino-2',4',6'-triisopropylbiphenyl plus potassium carbonate. Removal of protecting group $P^1$ results in compound IV. Protecting group $P^1$ in this case refers to groups well known to those skilled in the art for amine protection. For example, $P^1$ may be a tert-butoxycarbonyl (BOC), which can be cleaved via acidic conditions in an appropriate solvent, including but not limited to treatment with a solution of HCl in 1,4-dioxane. Alternatively $P^1$ may be one of many other protecting groups suitable for amines, including carboxybenzyl (Cbz) or benzoyl (Bz) groups and can be cleaved under standard conditions known to one skilled in the art. Compounds IV and V, wherein m an n are independently represented by an integer selected from 1 or 2, can be coupled to produce racemic compounds of Formula I using a standard reductive amination procedure using, for example but not limited to, a combination of sodium cyanoborohydride and titanium(IV) ethoxide in a suitable solvent. Chiral separation through, for example, a chiral chromatographic method such as HPLC or supercritical fluid chromatography, can produce compounds of Formula I'.

Scheme 2 a)

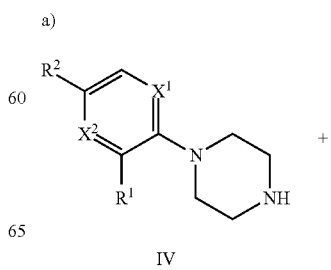

43
-continued
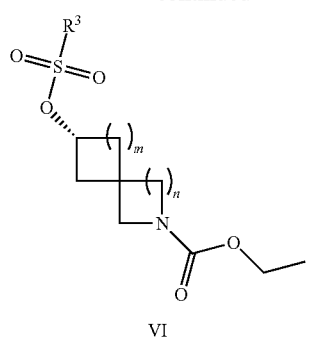
VI
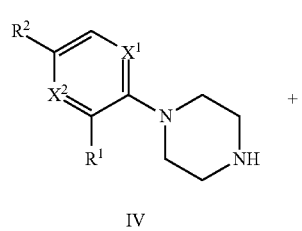
I'
b)
R² ⟨X¹⟩
X² ⟨⟩
R¹ N NH
IV
+
44
-continued
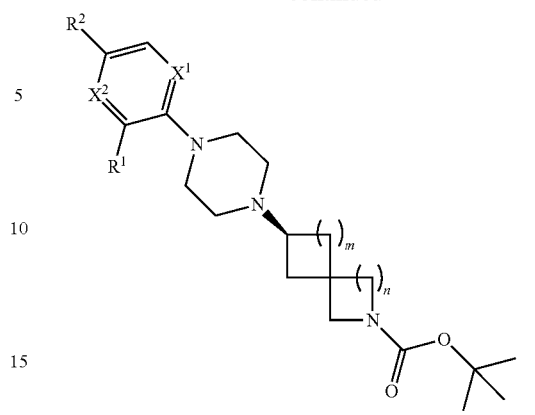
c)
R² ⟨X¹⟩
X² ⟨⟩
R¹ N NH
IV
+

-continued

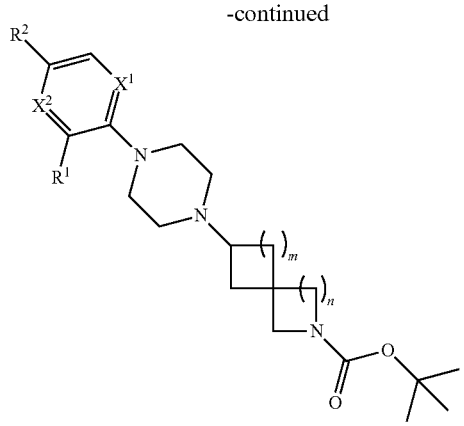

X

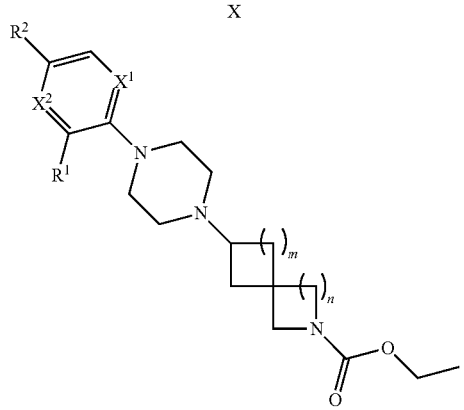

I

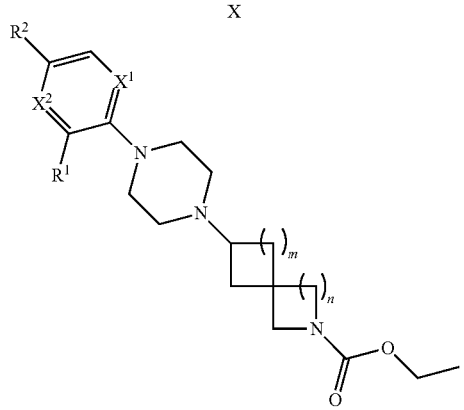

I'

Scheme 2 refers to alternative synthetic routes for the preparation of compounds of Formula I and I'. Referring to Scheme 2a, compound IV, wherein the $X^1$, $X^2$, $R^1$ and $R^2$ substituents of Formula IV should be represented by the same moieties as desired in the final product or protected variation thereof, can displace the sulfonate of enantiomerically pure compound VI, where $R^3$ is an aryl or alkyl substituent, for example methyl or 4-methylphenyl, and m and n are independently represented by an integer selected from 1 or 2, in the presence of a base such as potassium carbonate in an appropriate solvent, including but not limited to acetonitrile. Referring to Scheme 2b, compound IV, wherein $X^1$, $X^2$, $R^1$ and $R^2$ should be represented by the same moieties as desired in the final product or protected variation thereof, can similarly displace the alkyl sulfonate on chiral compound VII, where $R^3$ is an aryl or alkyl substituent, and m and n are independently represented by an integer selected from 1 or 2, to produce compound VIII. Removal of the BOC group, which can be cleaved via acidic conditions in an appropriate solvent, including but not limited to trifluoroacetic acid in dichloromethane, followed by treatment with ethyl chloroformate in dichloromethane or other appropriate solvents, produces compounds of Formula I'. Alternately, as shown in scheme 2c, compound IV, wherein the $X^1$, $X^2$, $R^1$ and $R^2$ substituents of Formula IV should be represented by the same moieties as desired in the final product or protected variation thereof, can be coupled to compound IX, wherein m and n are independently represented by an integer selected from 1 or 2, to produce compounds of the general Formula X using a standard reductive amination procedure using, for example but not limited to, a combination of sodium cyanoborohydride and titanium(IV) ethoxide in a suitable solvent. Removal of the BOC group, which can be cleaved via acidic conditions in an appropriate solvent, including but not limited to trifluoroacetic acid in dichloromethane, followed by treatment with ethyl chloroformate in dichloromethane or other appropriate solvent, produces racemic compounds of general Formula I. Compounds of Formula I' can be isolated after chiral separation, for example by chiral supercritical fluid chromatography or HPLC.

Scheme 3

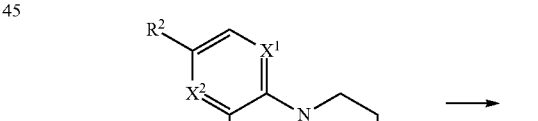

II

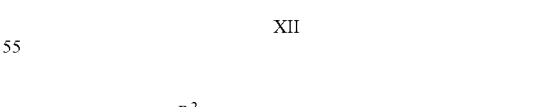

XII

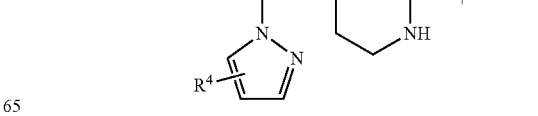

XIII

-continued

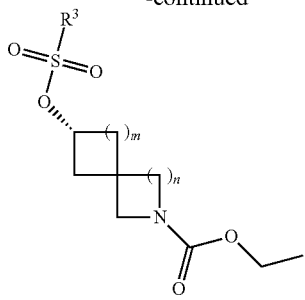

VI

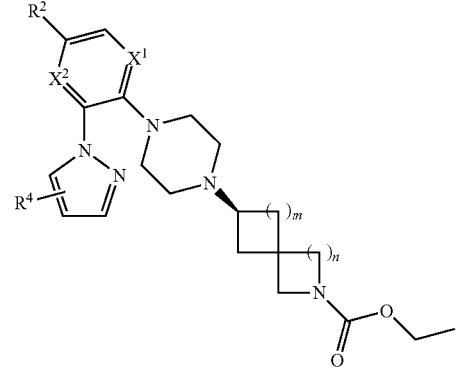

Ia

Scheme 3 refers to the preparation of compounds of Formula Ia. Compound II, wherein the $X^1$, $X^2$, and $R^2$ substituents of Formula II should be represented by the same moieties as desired in the final product or protected variation thereof, and XI, where $R_4$ is a small alkyl or alkyoxy, can be coupled to form compound XII via an Ullman coupling using, for example, a copper catalyst such as copper(I) iodide, a ligand such as (1R,2R)—N,N'-dimethylcyclohexane-1,2-diamine, and a base such as potassium phosphate in a suitable solvent such as NMP. Removal of protecting group $P^1$ results in compound XIII. $P^1$ in this case refers to groups well known to those skilled in the art for amine protection. For example, $P^1$ may be a tert-butoxycarbonyl (BOC), which can be cleaved via acidic conditions in an appropriate solvent, including but not limited to treatment with a solution of HCl in 1,4-dioxane. Synthesis of compounds of Formula Ia can be carried out through the reaction of chiral sulfonate compound VI, where $R^3$ is an aryl or alkyl substituent and m and n are independently represented by an integer selected from 1 or 2, with compound XIII in the presence of a base such as potassium carbonate in an appropriate solvent, including but not limited to acetonitrile.

Scheme 4

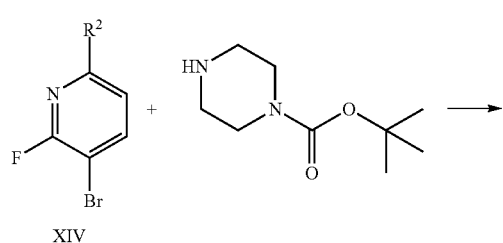

XIV

-continued

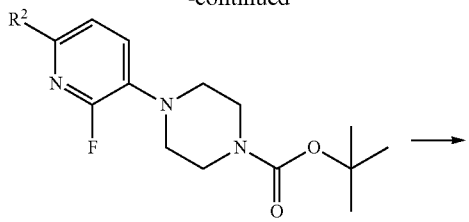

XV

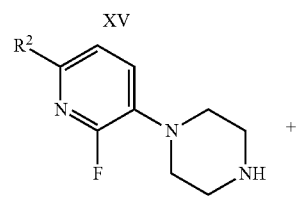

XVI

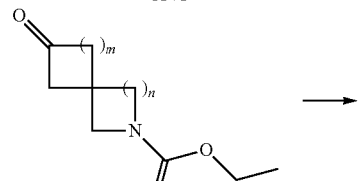

V

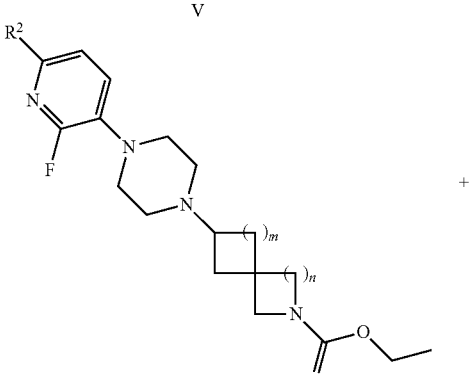

XVII $R^5$—OH

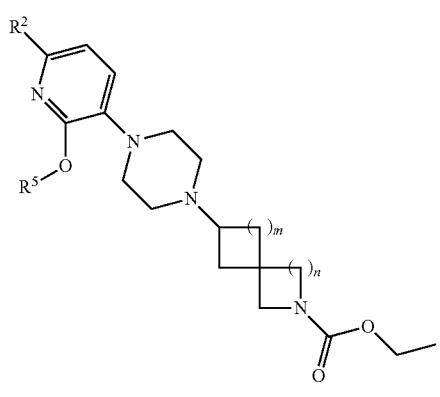

Ib

Scheme 4 refers to the preparation of compounds of Formula Ib. A cross-coupling reaction between compound XIV, wherein the $R^2$ substituent should be represented by the same moieties as desired in the final product or protected variation thereof, and tert-butyl piperazine-1-carboxylate to produce compound XV can be carried out using a palladium source, such as tris(dibenzylideneacetone)dipalladium(0), a ligand such as RuPhos ([2',6'-bis(propan-2-yloxy)biphenyl-2-yl](dicyclohexyl)phosphane), and a suitable base such as sodium tert-butoxide in 1,4-dioxane or other suitable solvent. Removal of the BOO group using acidic conditions, such as but not limited to HCl in 1,4-dioxane, results in the formation of compound XVI. Compounds XVI and V, wherein m and n are independently represented by an integer selected from 1 or 2, can be coupled to produce compound XVII using a standard reductive amination procedure using, for example but not limited to, a combination of sodium cyanoborohydride and titanium(IV) ethoxide in a suitable solvent. Nucleophilic displacement of the fluorine of compound XVII with an alcohol, where $R^5$ is as described above, using a suitable base such as sodium hydride in a suitable solvent such as DMF, affords compounds of Formula Ib.

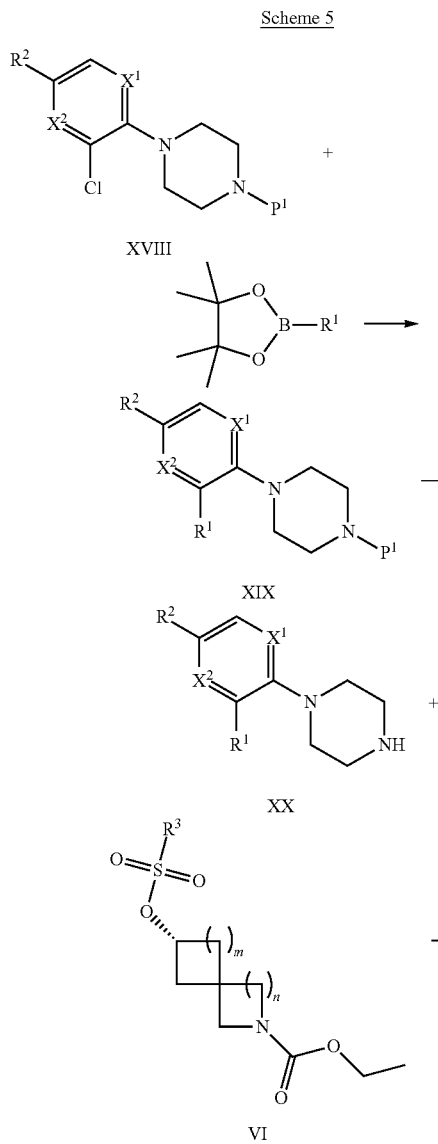

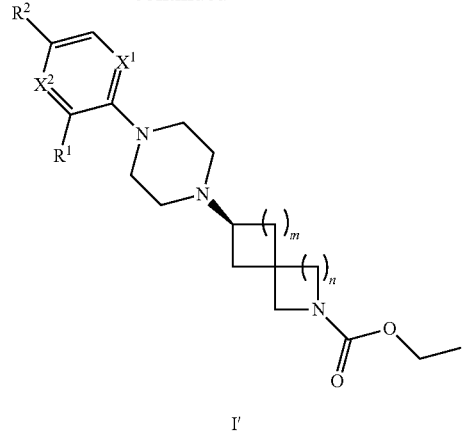

Scheme 5 refers to the synthesis of compounds of Formula I'. Compound XVIII, wherein the $X^1$, $X^2$, and $R^2$ substituents should be represented by the same moieties as desired in the final product or protected variation thereof, can be coupled with aryl or heteroaryl boronic acids, to produce compounds of the Formula XIX via a Suzuki coupling reaction using a standard selection of palladium source, ligand, and base, in a standard solvent, for example but not limited to acetonitrile, toluene, or ethanol. Examples of the Pd/ligand/base combination include but are not limited to [1,1'-bis(diphenylphosphino)ferrocene]dichloropalladium(II) and sodium carbonate. Removal of protecting group $P^1$ results in compound XX. $P^1$ may be a tert-butoxycarbonyl (BOC), which can be cleaved via acidic conditions in an appropriate solvent, including but not limited to treatment with a solution of HCl in 1,4-dioxane. Synthesis of compounds of Formula I' can be carried out through the displacement of the sulfonate of compound VI, where $R^3$ is an aryl or alkyl substituent and m and n are independently represented by an integer selected from 1 or 2, with compound XX in the presence of a suitable base such as potassium carbonate in an appropriate solvent, including but not limited to acetonitrile.

Scheme 6

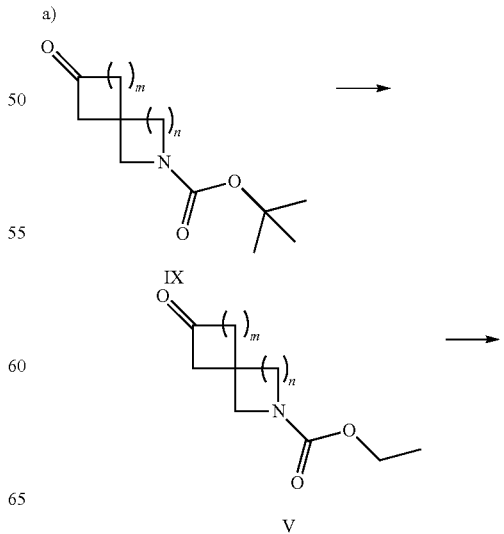

-continued

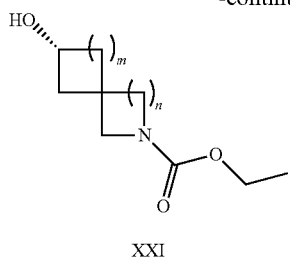

XXI

+ R³SO₂X →

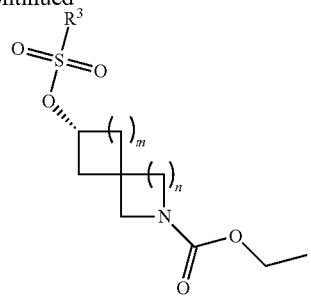

VI

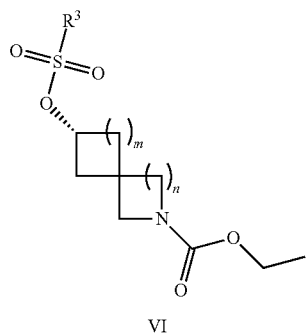

IX

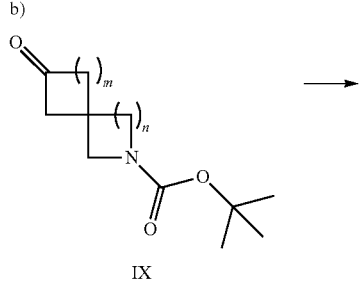

XXII

+ R³SO₂X →

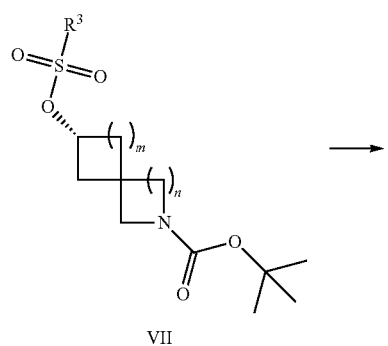

VII

Scheme 6 refers to the preparation of the general Formulas VI and VII. Referring to scheme 6a, the BOC protecting group on compound IX, wherein m and n are independently represented by an integer selected from 1 or 2, can be removed using acidic media, for example but not limited to HCl in methanol. The crude material can be combined with ethyl chloroformate and a base, such as triethylamine, in a solvent such as dichloromethane to form the ethyl carbamates of Formula V. Reduction of the ketone to enantiomerically pure alcohol XXI can be achieved using an enzymatic reagent, such as Codex® ketoreductase KRED-P3-G09 and NADP+ (nicotinamide adenine dinucleotide phosphate) in an appropriate buffer. Alternatively, a racemic reduction can also be carried out with a reductant such as sodium borohydride, for example, and chiral separation can be carried out at a later step. Combination of XXI with an activated alkyl or aryl sulfonyl chloride or anhydride in an appropriate solvent, in the presence of a base such as triethylamine, provides compounds of Formula VI. Referring to scheme 6b, ketone reduction of compound IX to enantiomerically pure alcohol XXII can be achieved using an enzymatic reagent, such as Codex® ketoreductase KRED-P3-G09 and NADP+(nicotinamide adenine dinucleotide phosphate) in an appropriate buffer. Addition of an alkyl or aryl sulfonyl chloride or anhydride with an appropriate base, such as triethylamine and 4-(dimethylamino)pyridine (DMAP) in a suitable solvent such as dichloromethane results in the formation of compounds of Formula VII. Removal of the BOC group can be carried out under appropriate acidic conditions, for example but not limited to trifluoroacetic acid in dichloromethane, then treatment of the resulting crude material with ethyl chloroformate under basic conditions, for example triethylamine in dichloromethane, results in the formation of compounds of Formula VI.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, with mixed solvent systems, such as but limited to aqueous plus acetonitrile, either or both of which may contain additives such as trifluoroacetic acid, formic acid, concentrated ammonium hydroxide, or with supercritical fluid chromatography, carried out using a combination of carbon dioxide and an organic solvent such as methanol or acetonitrile, optionally containing an additive such as diethylamine or ammonium hydroxide. on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well known to those of ordinary skill in the art.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "mL" means milliliter, "mmol" means millimoles, "μmol" means micromoles, "eq." means equivalent, "° C." means degrees Celsius, "MHz" means megahertz, "HPLC" means high-performance liquid chromatography.

EXPERIMENTAL PROCEDURES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4 Å molecular sieves, until the following QC standards for water were attained: a)<100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride, or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_{fs}$ or retention times. All starting materials in these Preparations and Examples are either commercially available or can be prepared by methods known in the art or as described herein.

The compounds and intermediates described below were named using the naming convention provided with ACD/ChemSketch 2012, File Version C10H41, Build 69045 (Advanced Chemistry Development, Inc., Toronto, Ontario, Canada). The naming convention provided with ACD/ChemSketch 2012 is well known by those skilled in the art and it is believed that the naming convention provided with ACD/ChemSketch 2012 generally comports with the IUPAC (International Union for Pure and Applied Chemistry) recommendations on Nomenclature of Organic Chemistry and the CAS Index rules.

Preparation P1

Ethyl 6-oxo-2-azaspiro[3.4]octane-2-carboxylate (P1)

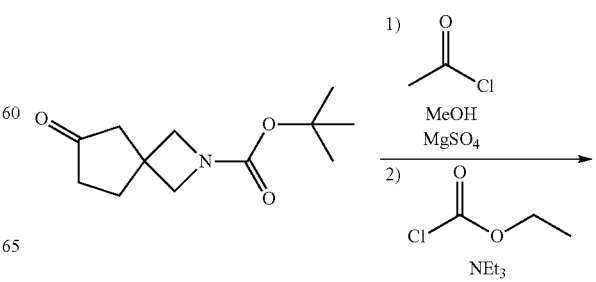

-continued

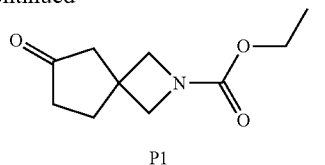

P1

Acetyl chloride (88 mL, 1.24 mol) was added to methanol (500 mL) at 0° C., and the resulting solution was stirred in a sealed vessel for 1 hour. To this solution of hydrogen chloride in methanol was added tert-butyl 6-oxo-2-azaspiro[3.4]octane-2-carboxylate (20.0 g, 88.8 mmol) and magnesium sulfate (20 g). The reaction mixture was stirred at 55° C. for 2 hours, whereupon it was cooled to room temperature and concentrated in vacuo. The residue (18.4 g) was mixed with dichloromethane (700 mL) and cooled to 0° C. under vigorous stirring. After drop-wise addition of ethyl chloroformate (30 mL, 310 mmol), the reaction mixture was treated drop-wise with triethylamine (60 mL, 430 mmol) and stirred at 0° C. for 1.5 hours. It was then allowed to warm to room temperature and stir overnight. Hydrochloric acid (1 M; 200 mL, 200 mmol) was added, and stirring was continued at room temperature for 10 minutes. The organic layer was washed with saturated aqueous sodium chloride solution (200 mL), dried over sodium sulfate, filtered, and concentrated under reduced pressure. Silica gel chromatography (Gradient: 0% to 100% ethyl acetate in heptane) afforded the product as an amber oil. Yield: 13.2 g, 66.9 mmol, 75%. $^1$H NMR (400 MHz, CDCl$_3$) δ 4.13 (q, J=7.2 Hz, 2H), 3.92 (AB quartet, $J_{AB}$=8.6 Hz, $\Delta_{vAB}$=9.1 Hz, 4H), 2.46 (s, 2H), 2.33-2.27 (m, 2H), 2.23-2.17 (m, 2H), 1.25 (t, J=7.2 Hz, 3H).

Preparation P2 tert-Butyl (6S)-6-[(methylsulfonyl)oxy]-2-azaspiro[3.4]octane-2-carboxylate (P2)

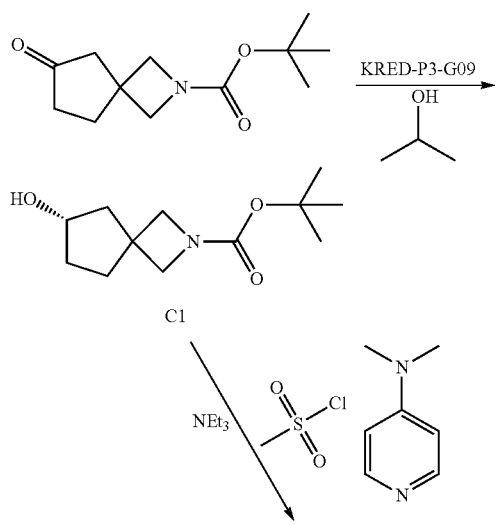

-continued

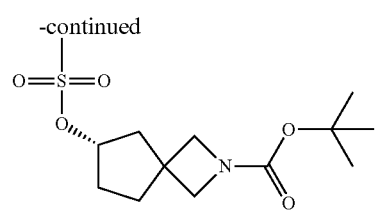

P2

Step 1. Synthesis of tert-butyl (6S)-6-hydroxy-2-azaspiro[3.4]octane-2-carboxylate (C1)

This experiment was carried out in 2 batches. A mixture of tert-butyl 6-oxo-2-azaspiro[3.4]octane-2-carboxylate (40.0 g, 178 mmol) in 2-propanol (64 mL, 840 mmol) was heated at 50° C. until a solution formed. A Mettler EasyMax reactor was charged with buffer [aqueous potassium phosphate, pH 7.5 (0.1 M, containing 2 mM magnesium chloride)](280 mL) at 30° C. and 600 rpm stirring. Codex® ketoreductase KRED-P3-G09 (800 mg) and NADP+(nicotinamide adenine dinucleotide phosphate) (80 mg) were added, and the resulting mixture was stirred for 10 minutes. The hot solution of substrate was slowly added, while the reaction temperature was maintained below 33° C. Additional 2-propanol (10 mL and 6 mL) was used to rinse the substrate flask. The reaction stirring rate was increased to 600 rpm, and a nitrogen sparge needle was applied at a flow of 100 cc/minute. Aliquots were taken periodically: approximately 80 μL of the reaction mixture was mixed with deuterochloroform (920 μL), and the sample was vortexed, centrifuged, and the organic layer was analyzed via $^1$H NMR. After 23 hours, additional Codex® ketoreductase KRED-P3-G09 (200 mg) and NADP+ (20 mg) were added as a solution in the pH 7.5 buffer (4 mL), followed by addition of 2-propanol (20 mL). After an additional 22 hours, the reaction mixture was diluted with ethyl acetate (400 mL) and stirred for 50 minutes, whereupon diatomaceous earth (25 g) was added, and the mixture was stirred for an additional 10 minutes. It was then filtered through diatomaceous earth (25 g), and the filter pad was rinsed with ethyl acetate (200 mL). This 200 mL filtrate was used to extract the aqueous layer from the initial filtration, and the combined organic layers were washed with saturated aqueous sodium chloride solution, dried over sodium sulfate, filtered, and concentrated in vacuo to afford a brown oil (39.6 g). The two batches were then combined in dichloromethane (600 mL), treated with silica gel (150 g) and concentrated in vacuo for chromatography. Silica gel chromatography (Gradient: 0% to 100% ethyl acetate in heptane; the product began to elute at approximately 50% ethyl acetate) afforded the product as a solid. Combined yield: 63.4 g, 279 mmol, 78%. $^1$H NMR (400 MHz, CDCl$_3$) δ 4.39-4.33 (m, 1H), 3.87 (AB quartet, $J_{AB}$=8.4 Hz, $\Delta_{vAB}$=41.1 Hz, 2H), 3.80-3.74 (m, 2H), 2.12-2.01 (m, 2H), 1.97-1.77 (m, 3H), 1.69-1.59 (m, 1H), 1.44 (s, 9H). Analysis provided an ee (enantiomeric excess) of >99% [Supercritical fluid chromatography. Column: Chiral Technologies Chiralpak AD-3, 100×3.0 mm, 3 μm; Mobile phase A: carbon dioxide; Mobile phase B: [methanol containing 0.2% (7 M ammonia in methanol)]; Gradient: 5% B for 1.0 minute, then 5% to 15% B over 7.0 minutes; Flow rate: 2.0 mL/minute; Back pressure: 1800 psi].

See below [Stereochemical correlation of tert-butyl (6S)-6-hydroxy-2-azaspiro[3.4]octane-2-carboxylate (C1) with ethyl (6S)-6-hydroxy-2-azaspiro[3.4]octane-2-carboxylate (C2)] for assignment of the indicated absolute stereochemistry of C1.

Step 2. Synthesis of tert-butyl (6S)-6-[(methylsulfonyl)oxy]-2-azaspiro[3.4]octane-2-carboxylate (P2)

Triethylamine (13.5 mL, 96.9 mmol) and 4-(dimethylamino)pyridine (295 mg, 2.41 mmol) were added to a solution of C1 (11.0 g, 48.4 mmol) in dichloromethane (400 mL). Methanesulfonyl chloride (8.40 mL, 108 mmol) was then added {Caution: exothermic} and the reaction mixture was allowed to stir overnight. After removal of solvent in vacuo, the residue was mixed with dichloromethane and filtered; the filtrate was concentrated under reduced pressure and purified via chromatography on silica gel (Gradient: 0% to 100% ethyl acetate in heptane) to provide the product as an oil. Yield: 14.6 g, 47.8 mmol, 99%. LCMS m/z 328.2 [M+Na]+ 1H NMR (400 MHz, CDCl3) δ 5.19-5.14 (m, 1H), 3.93 (d, half of AB quartet, J=8.2 Hz, 1H), 3.85-3.78 (m, 3H), 3.00 (s, 3H), 2.26 (br d, half of AB quartet, J=14.4 Hz, 1H), 2.16 (dd, component of ABX pattern, J=14.6, 6.0 Hz, 1H), 2.13-1.99 (m, 3H), 1.92-1.83 (m, 1H), 1.44 (s, 9H).

Preparation P3

Ethyl (6S)-6-[(methylsulfonyl)oxy]-2-azaspiro[3.4]octane-2-carboxylate (P3)

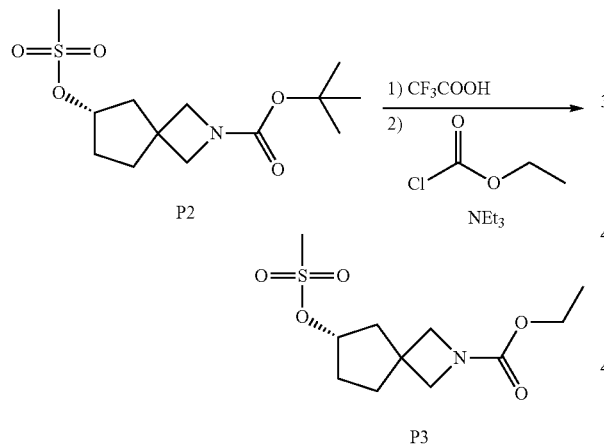

A mixture of P2 (14.6 g, 47.8 mmol) in dichloromethane (250 mL) and trifluoroacetic acid (55 mL, 710 mmol) was stirred at room temperature for 2 hours. The reaction mixture was concentrated in vacuo, and the residue was diluted with dichloromethane (250 mL) and sequentially treated with ethyl chloroformate (9.10 mL, 95.2 mmol) and triethylamine (26.7 mL, 192 mmol). After this reaction mixture had stirred at room temperature for 2 hours, it was concentrated under reduced pressure and purified using chromatography on silica gel (Gradient: 0% to 100% ethyl acetate in heptane). The product, which by 1H NMR analysis was not entirely pure, was obtained as a yellow oil. Yield: 13.1 g, 47.2 mmol, 99%. LCMS m/z 278.2 [M+H]+. 1H NMR (400 MHz, CDCl3), product peaks only: δ 5.20-5.15 (m, 1H), 4.12 (q, J=7.1 Hz, 2H), 4.00 (d, half of AB quartet, J=8.6 Hz, 1H), 3.91-3.85 (m, 3H), 3.00 (s, 3H), 2.29 (br d, half of AB quartet, J=14.8 Hz, 1H), 2.20-2.02 (m, 4H), 1.93-1.85 (m, 1H), 1.25 (t, J=7.0 Hz, 3H).

Preparation P4

Ethyl (6S)-6-{[(4-methylphenyl)sulfonyl]oxy}-2-azaspiro[3.4]octane-2-carboxylate (P4)

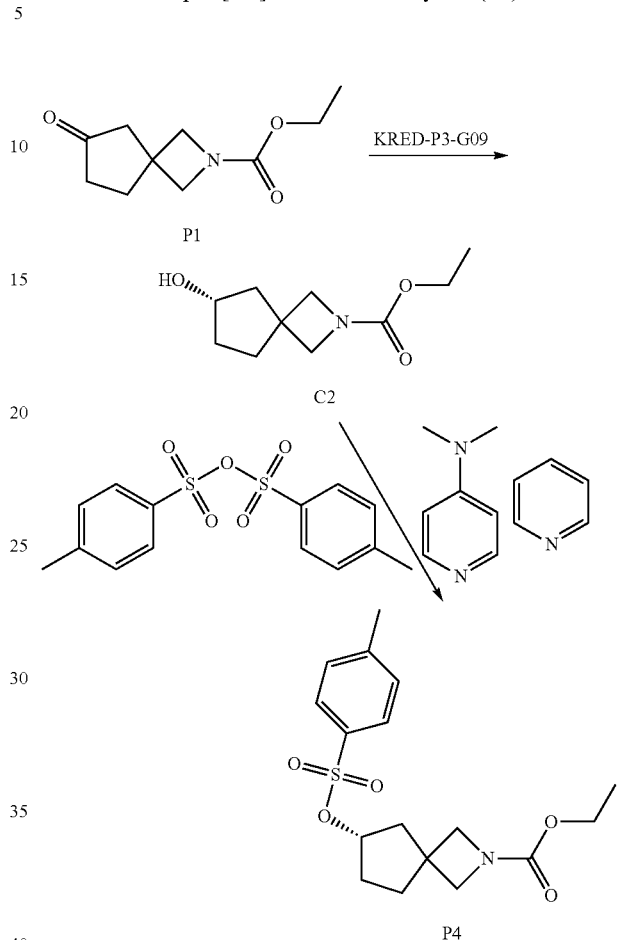

Step 1. Synthesis of ethyl (6S)-6-hydroxy-2-azaspiro[3.4]octane-2-carboxylate (C2)

A Mettler EasyMax reactor was charged with buffer [aqueous potassium phosphate, pH 7.0 (0.1 M, containing 2 mM magnesium chloride)] (8.0 mL) containing Codex® ketoreductase KRED-P3-G09 (60 mg) and NADP+(nicotinamide adenine dinucleotide phosphate) (6 mg). Additional buffer (2.5 mL) was used to rinse the glassware, and was added to the reaction mixture. A solution of P1 (1.5 g, 7.6 mmol) in 2-propanol (1.5 mL) was then added, along with a 2-propanol rinse (1.5 mL). The reaction mixture was stirred at 300 rpm and 30° C. with a 10 SCCM (standard cubic centimeters per minute) flow of nitrogen. Aliquots were taken periodically: approximately 50 μL of the reaction mixture was mixed with deuterochloroform (0.75 mL), and the sample was vortexed, centrifuged, and the organic layer was analyzed via 1H NMR. When the reaction had reached approximately 80% conversion, the nitrogen flow rate was increased to 25 SCCM, and the reaction was allowed to proceed overnight. Ethyl acetate (15 mL) was added, and the resulting mixture was vigorously stirred for 10 minutes, whereupon it was treated with diatomaceous earth (1.5 g) and filtered through a wetted pad of diatomaceous earth (1.5 g). After the filter pad had been washed with ethyl acetate (5 mL), the aqueous layer of the combined filtrates was mixed with ethyl acetate (15 mL), vigorously stirred for 5 minutes, and poured through the filter pad. Ethyl acetate (5 mL) was again used to wash the filter pad, and the aqueous layer from these filtrates was extracted in the same way. The combined organic layers from these manipulations were dried over sodium sulfate, filtered, and concentrated in vacuo. Chromatography on silica gel (Gradient: 20% to 80% ethyl acetate in heptane) afforded the product as a pale yellow oil. Analysis provided an ee (enantiomeric excess) of >99% {Supercritical fluid chromatography. Column: Chiral Technologies Chiralpak AD, 250×4.6 mm, 5 µm; Mobile phase: 85:15 carbon dioxide/[methanol containing 0.2% (7 M ammonia in methanol)]; Flow rate 3.0 mL/minute; Back pressure: 120 bar}. Yield: 1.20 g, 6.02 mmol, 79%. $^1$H NMR (400 MHz, CDCl$_3$) δ 4.41-4.33 (m, 1H), 4.10 (q, J=7.0 Hz, 2H), 3.93 (AB quartet, J$_{AB}$=8.4 Hz, Δ$_{vAB}$=42.3 Hz, 2H), 3.86-3.80 (m, 2H), 2.13-2.02 (m, 2H), 1.98-1.78 (m, 3H), 1.70-1.6 (m, 1H, assumed; partially obscured by water peak), 1.42 (d, J=3.1 Hz, 1H), 1.24 (t, J=7.0 Hz, 3H). The indicated absolute stereochemistry was assigned based on conversion of C2 to P4 and then to 6 (see Alternate Synthesis of Example 6 below).

Step 2. Synthesis of ethyl (6S)-6-{[(4-methylphenyl)sulfonyl]oxy}-2-azaspiro[3.4]octane-2-carboxylate (P4)

4-Methylbenzenesulfonic anhydride (6.29 g, 19.3 mmol) was added to a 0° C. mixture of C$_2$ (synthesized via bioreduction of P1, see previous step; 3.20 g, 16.1 mmol) in pyridine (80 mL). After addition of 4-(dimethylamino)pyridine (196 mg, 1.60 mmol), the reaction mixture was allowed to stir overnight, while the ice bath melted. LCMS analysis at this point indicated the presence of the product: LCMS m/z 354.3 [M+H]$^+$. After the reaction mixture had been concentrated in vacuo, it was diluted with aqueous sodium hydrogen sulfate solution (10%; 100 mL); the aqueous layer was then extracted sequentially with diethyl ether (150 mL) and with dichloromethane (150 mL). The combined organic layers were concentrated under reduced pressure and purified via chromatography on silica gel (Gradient: 0% to 100% ethyl acetate in heptane), affording the product as an oil. Yield: 4.54 g, 12.8 mmol, 80%. $^1$H NMR (400 MHz, CDCl$_3$) δ 7.78 (d, J=8.2 Hz, 2H), 7.35 (d, J=7.8 Hz, 2H), 5.01-4.92 (br m, 1H), 4.09 (q, J=7.2 Hz, 2H), 3.87 (AB quartet, J$_{AB}$=8.6 Hz, ΔΓ$_{AB}$=32.4 Hz, 2H), 3.82-3.76 (m, 2H), 2.46 (s, 3H), 2.12 (br d, half of AB quartet, J=14.8 Hz, 1H), 2.09-1.96 (m, 2H), 1.94-1.86 (m, 2H), 1.85-1.76 (m, 1H), 1.24 (t, J=7.2 Hz, 3H). The indicated absolute configuration of this material was established via its use below in Alternate Synthesis of Example 6. That sample of 6 was shown to be identical to the material used in the X-ray crystal structure determination described below.

Stereochemical correlation of tert-butyl (6S)-6-hydroxy-2-azaspiro[3.4]octane-2-carboxylate (C1) with ethyl (6S)-6-hydroxy-2-azaspiro[3.4]octane-2-carboxylate (C2)

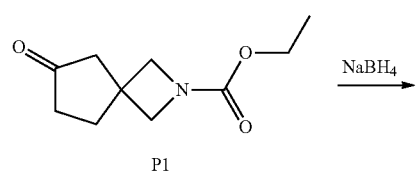

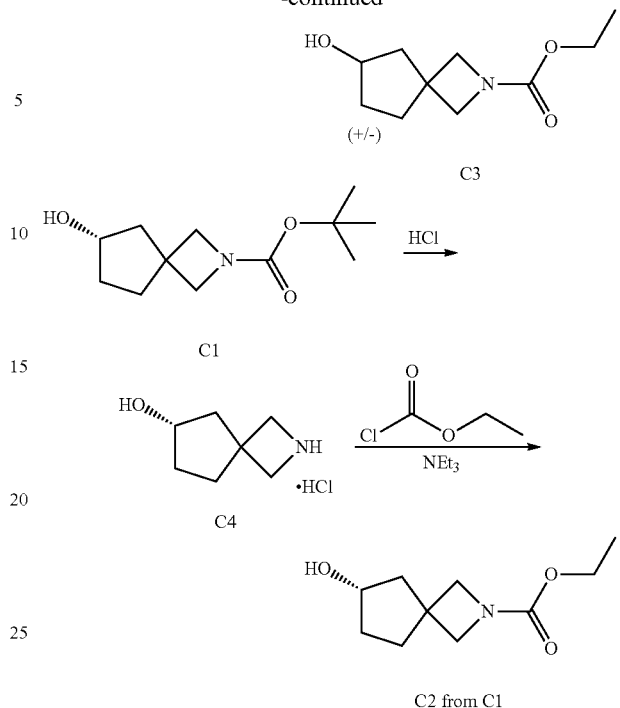

Synthesis of ethyl 6-hydroxy-2-azaspiro[3.4]octane-2-carboxylate (C3)

Sodium borohydride (95 mg, 2.5 mmol) was added in one portion to a solution of P1 (280 mg, 1.42 mmol) in methanol (10 mL) {Caution: exothermic). After the reaction mixture had been stirred for 2 hours, it was diluted with hydrochloric acid (1 M; 5 mL) and stirred at room temperature for 5 minutes. Water (5 mL) was then added, and the aqueous layer was extracted with dichloromethane (2×30 mL). The combined organic layers were dried over sodium sulfate, filtered, and concentrated in vacuo to afford the product as an oil. Yield: 233 mg, 1.17 mmol, 82%. $^1$H NMR (400 MHz, CDCl$_3$) δ 4.41-4.34 (m, 1H), 4.10 (q, J=7.2 Hz, 2H), 3.93 (AB quartet, J$_{AB}$=8.4 Hz, Δ$_{vAB}$=41.9 Hz, 2H), 3.86-3.80 (m, 2H), 2.14-2.02 (m, 2H), 1.98-1.78 (m, 3H), 1.70-1.6 (m, 1H, assumed; partially obscured by water peak), 1.45-1.32 (br s, 1H), 1.24 (t, J=7.2 Hz, 3H).

Step 1. Synthesis of (6S)-2-azaspiro[3.4]octan-6-ol, hydrochloride salt (C4)

A solution of hydrogen chloride in 1,4-dioxane (4 M; 8 mL, 32 mmol) was added to a mixture of C$_1$ (512 mg, 2.25 mmol) in ethyl acetate (12 mL), and the reaction mixture was stirred at room temperature for 3 hours. Removal of solvents in vacuo afforded the product, which was taken into the following reaction without purification.

Step 2. Synthesis of ethyl (6S)-6-hydroxy-2-azaspiro[3.4]octane-2-carboxylate (C2 from C1)

Ethyl chloroformate (0.258 mL, 2.70 mmol) was added drop-wise to a mixture of C$_4$ (from the previous step, 52.25 mmol) and triethylamine (0.943 mL, 6.76 mmol) in dichloromethane (10 mL). After the reaction mixture had been stirred at room temperature for 1 hour, it was diluted with hydrochloric acid (1 M; 10 mL) and stirred at room temperature for 5 minutes. The aqueous layer was extracted with dichloromethane (15 mL), and the combined organic layers were dried over sodium sulfate, filtered, and concentrated in vacuo. Chromatography on silica gel (Gradient: 0% to 100% ethyl acetate in heptane) provided the product as an oil. By $^1$H NMR analysis, this material was not entirely pure. Yield: 100 mg, 0.502 mmol, 22% over 2 steps. $^1$H NMR (400 MHz, CDCl$_3$), product peaks only: δ 4.34-4.26 (br m, 1H), 4.06 (q, J=7.0 Hz, 2H), 3.89 (AB quartet, J$_{AB}$=8.6 Hz, Δ$_{vAB}$=44.8 Hz, 2H), 3.81-3.75 (m, 2H), 2.09-1.96 (m, 2H), 1.93-1.82 (m, 2H), 1.82-1.73 (m, 1H), 1.66-1.56 (m, 1H), 1.20 (t, J=7.2 Hz, 3H).

The absolute stereochemistries of C$_1$ and C$_2$ from KRED-P3-G09 reduction (Preparation P4) were shown to be the same in the following manner. Compound C$_1$ was converted into sample C2 from C1 (Steps 1 and 2 above). The racemate of C2 (C3) was examined via supercritical fluid chromatography [Column: Chiral Technologies Chiralpak AD-H, 250× 4.6 mm, 5 μm; Mobile phase A: carbon dioxide; Mobile phase B: methanol containing 0.2% (7 M ammonia in methanol); Gradient: 5% B for 1.0 minute, then 5% to 40% B over 8.0 minutes; Flow rate: 3.0 mL/minute; Back pressure: 1800 psi]. The two enantiomers eluted at retention times of 4.57 and 4.94 minutes. A sample of C2 from reduction of P1 with KRED-P3-G09 (Preparation P4) provided a retention time of 4.9 minutes under the same chromatographic conditions, as did the sample of C2 from C1.

Examples 1, 2, and 3

Ethyl 6-(4-[3-(5-methoxypyrazin-2-yl)pyridin-2-yl]piperazin-1-yl}-2-azaspiro[3.4]octane-2-carboxylate (1), Ethyl 6-{4-[3-(5-methoxypyrazin-2-yl)pyridin-2-yl]piperazin-1-yl}-2-azaspiro[3.4]octane-2-carboxylate, ENT-1 (2), and Ethyl 6-{4-[3-(5-methoxypyrazin-2-yl}pyridin-2-yl]piperazin-1-yl}-2-azaspiro[3.4]octane-2-carboxylate, ENT-2(3)

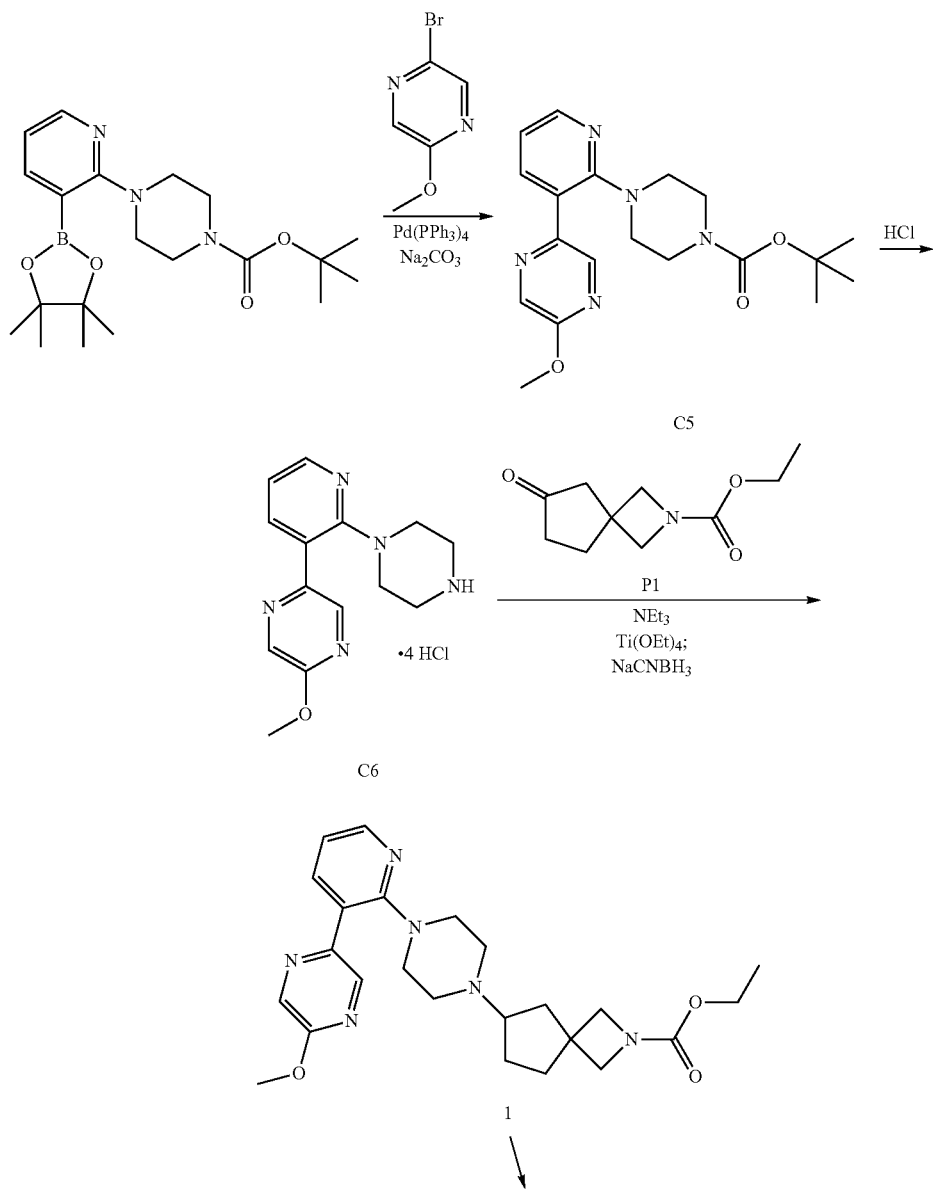

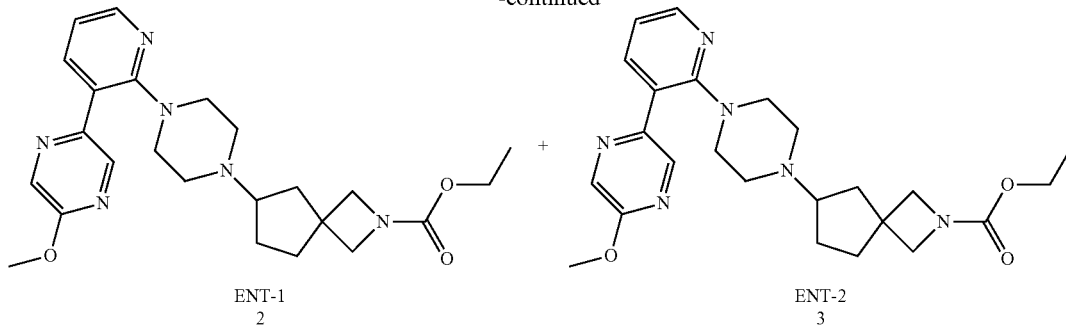

Step 1. Synthesis of tert-butyl 4-[3-(5-methoxypyrazin-2-yl)pyridin-2-yl]piperazine-1-carboxylate (C5)

A solution of tetrakis(triphenylphosphine)palladium(0) (89 mg, 77 μmol) in toluene (5 mL) and ethanol (2 mL) was added to a mixture of tert-butyl 4-[3-(4,4,5,5-tetramethyl-1,3,2-dioxaborolan-2-yl)pyridin-2-yl]piperazine-1-carboxylate (300 mg, 0.771 mmol), 2-bromo-5-methoxypyrazine (146 mg, 0.772 mmol), and aqueous sodium carbonate solution (2 M, 10 mL). The reaction mixture was stirred at 100° C. under microwave irradiation for 3 hours, whereupon it was concentrated in vacuo. [Experiments referencing this method often used standard heating, at 60° C. or higher.] Purification of the residue using silica gel chromatography (Gradient: 0% to 40% ethyl acetate in petroleum ether) provided the product as a yellow solid. Yield: 260 mg, 0.700 mmol, 91%. LCMS m/z 372.2 [M+H]$^+$. $^1$H NMR (400 MHz, CDCl$_3$) δ 8.80-8.72 (br s, 1H), 8.33 (d, J=1.5 Hz, 1H), 8.33-8.28 (m, 1H), 7.86 (br d, J=6.8 Hz, 1H), 7.08-7.01 (m, 1H), 4.03 (s, 3H), 3.50-3.41 (br m, 4H), 3.21-3.05 (br m, 4H), 1.46 (s, 9H).

Step 2. Synthesis of 2-methoxy-5-[2-(piperazin-1-yl)pyridin-3-yl]pyrazine, tetrahydrochloride salt (C6)

A solution of hydrogen chloride in 1,4-dioxane (4 M; 3 mL, 12 mmol) was added to a solution of C5 (260 mg, 0.700 mmol) in acetonitrile (6 mL), and the reaction mixture was stirred at room temperature for 2 hours. Removal of solvents in vacuo afforded the product as a yellow oil, which was used directly in the next step. By $^1$H NMR analysis, this material was not entirely pure. Yield: 290 mg, 0.695 mmol, 99%. LCMS m/z 272.2 [M+H]$^+$. $^1$H NMR (400 MHz, DMSO-d$_6$), product peaks only: δ 9.57-9.42 (br m, 2H), 8.77 (d, J=1.2 Hz, 1H), 8.45 (d, J=1.5 Hz, 1H), 8.30 (dd, J=5.1, 1.7 Hz, 1H), 7.98 (dd, J=7.3, 1.5 Hz, 1H), 7.22 (dd, J=7.5, 5.3 Hz, 1H), 3.98 (s, 3H), 3.36-3.28 (br m, 4H), 3.12-3.04 (br m, 4H).

Step 3. Synthesis of ethyl 6-{4-[3-(5-methoxypyrazin-2-yl)pyridin-2-yl]piperazin-1-yl}-2-azaspiro[3.4]octane-2-carboxylate (1)

A mixture of C6 (220 mg, 0.527 mmol) and triethylamine (1.0 mL, 7.2 mmol) in dichloromethane (40 mL) was stirred for 30 minutes at room temperature, whereupon P1 (156 mg, 0.791 mmol) was added, followed by titanium(IV) ethoxide (1.5 mL, 7.2 mmol). After the reaction mixture had been stirred for 16 hours at room temperature, sodium cyanoborohydride (490 mg, 7.80 mmol) was added, followed by methanol (6 mL), and stirring was continued for another 4 hours at room temperature. Water (4 mL) was then added, and the resulting mixture was concentrated in vacuo. Purification was carried out using silica gel chromatography (Gradient: 0% to 10% methanol in dichloromethane), followed by reversed-phase chromatography (Column: Agela Technologies C18; Mobile phase A: water containing 0.05% ammonium hydroxide; Mobile phase B: acetonitrile; Gradient: 45% to 60% B). The product was isolated as a light yellow solid. Yield: 170 mg, 0.376 mmol, 71%. LCMS m/z 453.3 [M+H]$^+$. $^1$H NMR (400 MHz, CDCl$_3$) δ 8.76 (br s, 1H), 8.32 (d, J=1.2 Hz, 1H), 8.28 (dd, J=4.9, 1.7 Hz, 1H), 7.81 (dd, J=7.5, 1.8 Hz, 1H), 6.99 (dd, J=7.5, 5.0 Hz, 1H), 4.10 (q, J=7.1 Hz, 2H), 4.04 (s, 3H), 3.86 (AB quartet, downfield doublet is broadened, $J_{AB}$=8.3 Hz, $\Delta_{vAB}$=22.5 Hz, 2H), 3.81-3.74 (m, 2H), 3.29-3.10 (br m, 4H), 2.67-2.40 (br m, 5H), 2.11 (dd, J=12, 7 Hz, 1H), 2.02-1.45 (m, 5H, assumed; partially obscured by water peak), 1.24 (t, J=7.1 Hz, 3H).

Step 4. Isolation of ethyl 6-{4-[3-(5-methoxypyrazin-2-yl)pyridin-2-yl]piperazin-1-yl}-2-azaspiro[3.4]octane-2-carboxylate, ENT-1 (2) and ethyl 6-{4-[3-(5-methoxypyrazin-2-yl)pyridin-2-yl]piperazin-1-yl}-2-azaspiro[3.4]octane-2-carboxylate, ENT-2 (3)

Separation of 1 (150 mg, 0.331 mmol) into its component enantiomers was carried out via reversed-phase HPLC [Column: Chiral Technologies ChiralCel OD, 10 μm; Mobile phase: 4:1 hexane/ethanol]. The isolated enantiomers were then individually subjected to reversed-phase chromatography (Column: Agela Technologies C18; Mobile phase A: water containing 0.1% ammonium hydroxide; Mobile phase B: acetonitrile; Gradient: 0% to 60% B) to afford the products as yellow solids. The first-eluting enantiomer was designated as 2, and the second-eluting enantiomer as 3.

2—Yield: 40 mg, 88 μmol, 27%. LCMS m/z 453.3 [M+H]$^+$. $^1$H NMR (400 MHz, CDCl$_3$) δ 8.76 (br s, 1H), 8.32 (d, J=1.2 Hz, 1H), 8.28 (dd, J=4.8, 1.8 Hz, 1H), 7.81 (dd, J=7.5, 1.8 Hz, 1H), 6.99 (dd, J=7.3, 4.9 Hz, 1H), 4.10 (q, J=7.1 Hz, 2H), 4.03 (s, 3H), 3.86 (AB quartet, downfield doublet is broadened, $J_{AB}$=8.3 Hz, $\Delta_{vAB}$=22.5 Hz, 2H), 3.80-3.74 (m, 2H), 3.30-3.10 (br m, 4H), 2.69-2.41 (br m, 5H), 2.11 (dd, J=12.5, 6.8 Hz, 1H), 2.00-1.48 (m, 5H, assumed; partially obscured by water peak), 1.24 (t, J=7.1 Hz, 3H). Retention time: 3.52 minutes (Analytical conditions. Column: Chiral Technologies ChiralCel OD-H, 150× 4.6 mm, μm; Mobile phase: 80:20:0.1 hexane/ethanol/diethylamine; Flow rate: 1.0 mL/minute).

3—Yield: 43 mg, 95 μmol, 29%. LCMS m/z 453.3 [M+H]+. 1H NMR (400 MHz, CDCl3) δ 8.75 (br s, 1H), 8.32 (d, J=1.2 Hz, 1H), 8.28 (dd, J=4.9, 2.0 Hz, 1H), 7.81 (dd, J=7.5, 1.8 Hz, 1H), 6.99 (dd, J=7.3, 4.9 Hz, 1H), 4.10 (q, J=7.1 Hz, 2H), 4.04 (s, 3H), 3.93-3.86 (br m, 1H), 3.84 (d, half of AB quartet, J=8.3 Hz, 1H), 3.80-3.75 (m, 2H), 3.33-3.06 (br m, 4H), 2.71-2.35 (br m, 5H), 2.18-2.06 (m, 1H), 2.04-1.45 (m, 5H, assumed; partially obscured by water peak), 1.24 (t, J=7.1 Hz, 3H). Retention time: 4.53 minutes (Analytical conditions identical to those used for 2).

Example 4

Ethyl (6R)-6-{4-[3-(1,3-thiazol-4-yl)pyridin-2-yl]piperazin-1-yl}-2-azaspiro[3.4]octane-2-carboxylate (4)

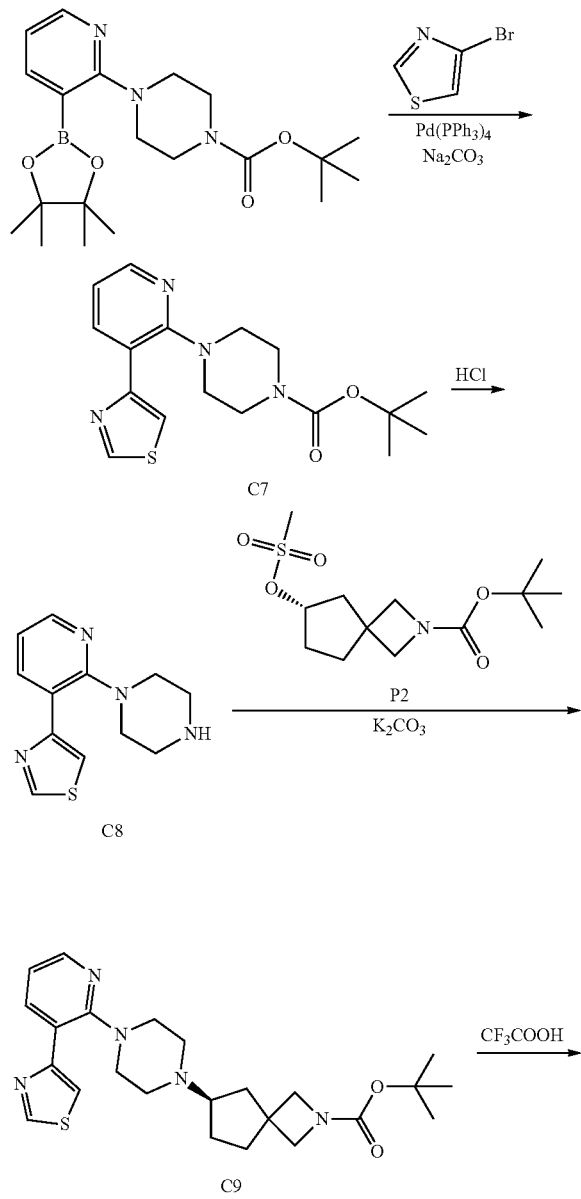

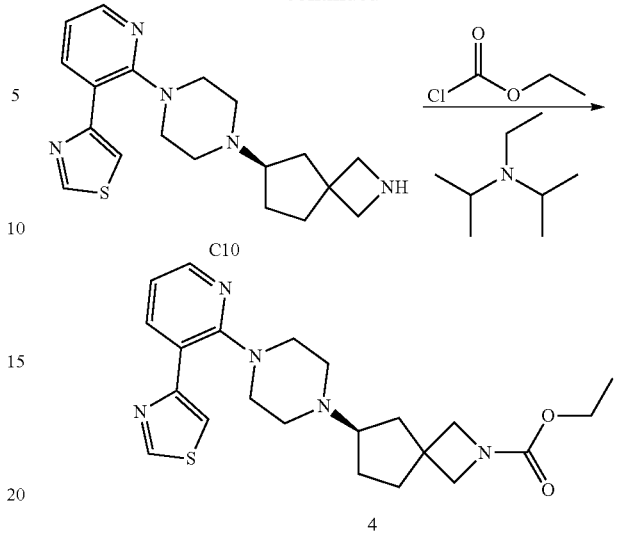

Step 1. Synthesis of tert-butyl 4-[3-(1,3-thiazol-4-yl)pyridin-2-yl]piperazine-1-carboxylate (C7)

Ethanol (30 mL) and a solution of sodium carbonate (8.85 g, 83.5 mmol) in water (33 mL) were added to a mixture of tert-butyl 4-[3-(4,4,5,5-tetramethyl-1,3,2-dioxaborolan-2-yl)pyridin-2-yl]piperazine-1-carboxylate (13.0 g, 33.4 mmol) and 4-bromo-1,3-thiazole (6.57 g, 40.1 mmol) in toluene (180 mL). Tetrakis(triphenylphosphine)palladium (0) (2.69 g, 2.33 mmol) was then added, and the reaction mixture was stirred for 12 hours at 90° C. After removal of solvents in vacuo, the residue was purified using silica gel chromatography (Gradient: 0% to 60% ethyl acetate in petroleum ether) to afford the product as a light yellow solid. Yield: 7.00 g, 20.2 mmol, 60%. LCMS m/z 347.1 [M+H]+.

Step 2. Synthesis of 1-[3-(1,3-thiazol-4-yl)pyridin-2-yl]piperazine (C8)

A solution of hydrogen chloride in 1,4-dioxane (4 M; 50 mL, 200 mmol) was added to a 0° C. solution of C7 (11.0 g, 31.8 mmol) in acetonitrile (100 mL). The reaction mixture was stirred for 16 hours at room temperature, whereupon it was filtered. The collected solids were washed with ethyl acetate and then suspended in a mixture of dichloromethane (150 mL) and methanol (25 mL). Potassium carbonate (20 g, 145 mmol) was added, and the mixture was stirred for 16 hours at room temperature, then filtered. The filter cake was washed with a mixture of dichloromethane and methanol (10:1, 60 mL), and the combined filtrates were dried over sodium sulfate, filtered, and concentrated in vacuo to provide the product as a yellow oil. By 1H NMR analysis, this material was not entirely pure. Yield: 7.5 g, 30 mmol, 94%. LCMS m/z 247.1 [M+H]+. 1H NMR (400 MHz, DMSO-d6), product peaks only: δ 9.19 (d, J=2.0 Hz, 1H), 8.24 (d, J=2.0 Hz, 1H), 8.22 (dd, J=4.8, 1.8 Hz, 1H), 8.10 (dd, J=7.5, 1.8 Hz, 1H), 7.04 (dd, J=7.5, 4.8 Hz, 1H), 2.97-2.91 (m, 4H), 2.80-2.73 (m, 4H).

Step 3. Synthesis of tert-butyl (6R)-6-{4-[3-(1,3-thiazol-4-yl)pyridin-2-yl]piperazin-1-yl}-2-azaspiro[3.4]octane-2-carboxylate (C9)

This experiment was carried out in two identical batches. A mixture of C8 (1.10 g, 4.47 mmol), P2 (1.91 g, 6.25 mmol), and potassium carbonate (1.54 g, 11.1 mmol) in acetonitrile (20 mL) was placed in a sealed vessel and heated at 95° C. for 16 hours, whereupon it was concentrated in vacuo. Silica gel chromatography (Gradient: 0% to 10% methanol in dichloromethane) afforded the product as a light yellow oil. Combined yield: 1.70 g, 3.73 mmol, 42%. LCMS m/z 456.2 [M+H]$^+$. $^1$H NMR (400 MHz, DMSO-d$_6$) δ 9.20 (d, J=1.5 Hz, 1H), 8.23 (dd, J=4.6, 1.5 Hz, 1H), 8.20 (br s, 1H), 8.10 (br d, J=7.6 Hz, 1H), 7.06 (dd, J=7.3, 4.6 Hz, 1H), 3.76-3.58 (br m, 4H), 3.07-2.96 (br m, 4H), 2.64-2.39 (m, 5H, assumed; largely obscured by solvent peak), 2.07-1.96 (m, 1H), 1.87-1.69 (m, 3H), 1.69-1.57 (m, 1H), 1.50-1.4 (m, 1H), 1.36 (s, 9H).

Step 4. Synthesis of (6R)-6-{4-[3-(1,3-thiazol-4-yl) pyridin-2-yl]piperazin-1-yl}-2-azaspiro[3.4]octane (C10)

Trifluoroacetic acid (15 mL) was added to a solution of C9 (6.00 g, 13.2 mmol) in dichloromethane (120 mL), and the reaction mixture was stirred for 16 hours at room temperature. It was then concentrated in vacuo, and the residue was dissolved in a mixture of dichloromethane and methanol (9:1, 150 mL); sodium carbonate (15 g) was added, and the resulting mixture was stirred for 3 hours at room temperature. The mixture was then filtered, and the filtrate was concentrated under reduced pressure, providing the product as a yellow oil. Yield: 4.50 g, 12.7 mmol, 96%. LCMS m/z 356.2 [M+H]$^+$. $^1$H NMR (400 MHz, CD$_3$OD) δ 9.15-9.13 (m, 1H), 8.31-8.27 (m, 1H), 8.16-8.13 (m, 1H), 8.07 (br d, J=7.6 Hz, 1H), 7.18-7.12 (m, 1H), 3.69 (br d, half of AB quartet, J=12 Hz, 1H), 3.65-3.49 (m, 5H), [3.40-3.24 (m) and 3.16-3.07 (m), total 7H, assumed; partially obscured by solvent peak], 2.41-2.28 (m, 2H), 2.02-1.81 (m, 3H), 1.72-1.63 (br m, 1H).

Step 5. Synthesis of ethyl (6R)-6-{4-[3-(1,3-thiazol-4-yl) pyridin-2-yl]piperazin-1-yl}-2-azaspiro[3.4]octane-2-carboxylate (4). Ethyl chloroformate (3.66 g, 33.7 mmol) was added to a 0° C. mixture of C10 (4.00 g, 11.2 mmol) and N,N-diisopropylethylamine (8.73 g, 67.5 mmol), and the reaction mixture was stirred at room temperature for 3 hours. After the reaction mixture had been poured into water, it was extracted with dichloromethane (2×50 mL). The combined organic layers were concentrated and purified via chromatography on silica gel (Gradient: 0% to 10% methanol in dichloromethane) to afford a light yellow gum (2.1 g); this material was repurified using silica gel chromatography (Gradient: 0% to 20% methanol in dichloromethane) to provide the product as a tan foam. Yield: 1.77 g, 4.14 mmol, 37%. LCMS m/z 428.4 [M+H]$^+$. $^1$H NMR (400 MHz, CDCl$_3$) δ 8.88 (d, J=2.0 Hz, 1H), 8.26 (dd, J=4.7, 2.0 Hz, 1H), 8.11 (dd, J=7.4, 2.0 Hz, 1H), 8.02 (d, J=2.0 Hz, 1H), 6.98 (dd, J=7.6, 4.9 Hz, 1H), 4.10 (q, J=7.0 Hz, 2H), 3.86 (AB quartet, J$_{AB}$=8.4 Hz, Δ$_{vAB}$=20.8 Hz, 2H), 3.79 (AB quartet, J$_{AB}$=8.4 Hz, Δ$_{vAB}$=6.0 Hz, 2H), 3.21-3.15 (m, 4H), 2.62-2.48 (br m, 5H), 2.12 (dd, J=12.7, 6.8 Hz, 1H), 1.98-1.78 (m, 3H), 1.72 (dd, J=12.7, 9.6 Hz, 1H), 1.61-1.50 (m, 1H), 1.24 (t, J=7.2 Hz, 3H).

Example 5

Ethyl (6R)-6-(4-[3-(1,3,4-thiadiazol-2-yl)pyridin-2-yl]piperazin-1-yl}-2-azaspiro[3.4]octane-2-carboxylate (5)

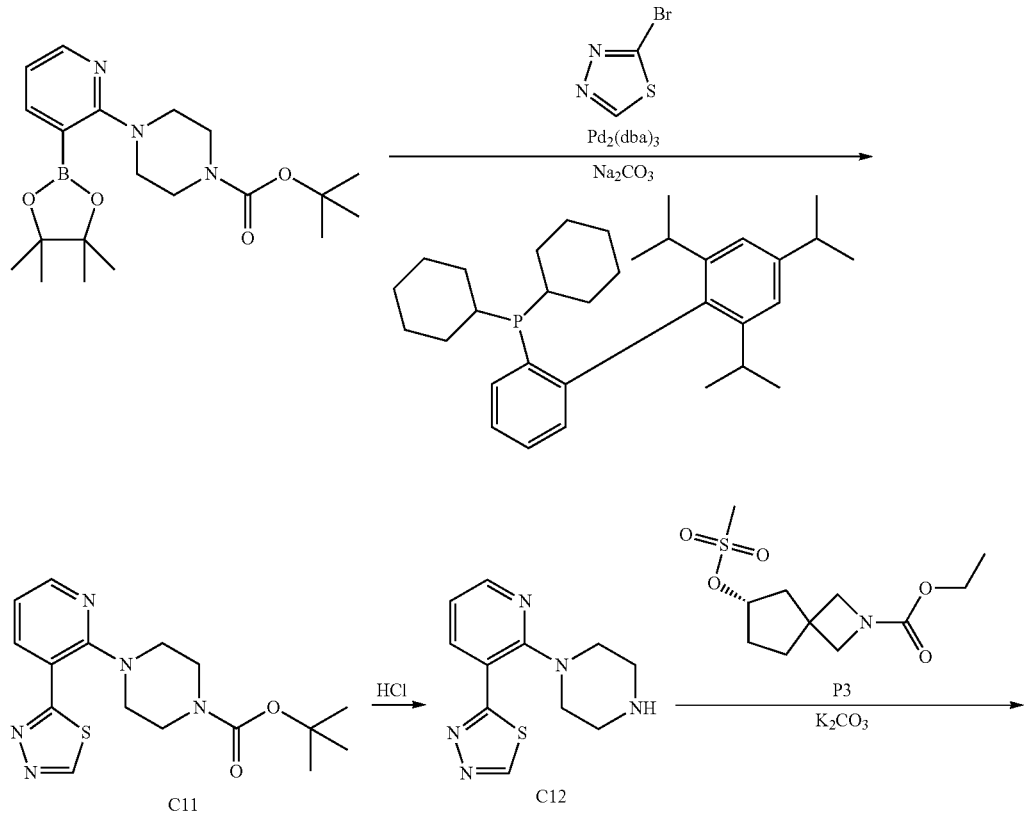

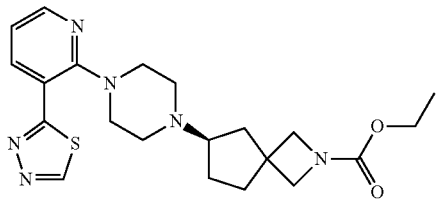

5

Step 1. Synthesis of tert-butyl 4-[3-(1,3,4-thiadiazol-2-yl)pyridin-2-yl]piperazine-1-carboxylate (C11). This experiment was carried out in 8 identical batches To a mixture of tert-butyl 4-[3-(4,4,5,5-tetramethyl-1,3,2-dioxaborolan-2-yl)pyridin-2-yl]piperazine-1-carboxylate (400 mg, 1.03 mmol) in acetonitrile (20 mL) was added 2-dicyclohexylphosphino-2',4',6'-triisopropylbiphenyl (XPhos; 147 mg, 0.308 mmol), followed by 2-bromo-1,3,4-thiadiazole (203 mg, 1.23 mmol), sodium carbonate (163 mg, 1.54 mmol), water (4 mL), and tris(dibenzylideneacetone)dipalladium(0) (94.0 mg, 0.103 mmol). The reaction mixture was stirred for 7 hours at 100° C. in a sealed vessel, whereupon it was concentrated in vacuo and purified via chromatography on silica gel (Gradient: 0% to 80% ethyl acetate in petroleum ether) to provide a light yellow oil (550 mg). The products from all 8 reactions were combined and subjected to silica gel chromatography (Gradient: 0% to 70% ethyl acetate in petroleum ether), affording the product as a light yellow solid. Combined yield: 1.20 g, 3.45 mmol, 42%. LCMS m/z 348.1 [M+H]$^+$. $^1$H NMR (400 MHz, CDCl$_3$) δ 9.20 (s, 1H), 8.50 (dd, J=7.7, 1.8 Hz, 1H), 8.47 (dd, J=4.8, 1.8 Hz, 1H), 7.19 (dd, J=7.7, 4.8 Hz, 1H), 3.61 (dd, J=5, 5 Hz, 4H), 3.10 (dd, J=5, 5 Hz, 4H), 1.48 (s, 9H).

Step 2. Synthesis of 1-[3-(1,3,4-thiadiazol-2-yl)pyridin-2-yl]piperazine (C12).

A solution of hydrogen chloride in 1,4-dioxane (4 M; 15 mL, 60 mmol) was added to a mixture of C11 (1.10 g, 3.17 mmol) in acetonitrile (30 mL), and the reaction mixture was stirred for 3 hours at room temperature. After removal of solvents in vacuo, the residue was triturated with ethyl acetate to provide a white solid (1.0 g). This material was taken up in a mixture of dichloromethane and methanol (10:1, 150 mL), and treated with potassium carbonate (5.0 g, 36.2 mmol); after this mixture had been stirred for 16 hours at room temperature, it was filtered. The filtrate was dried over sodium sulfate and concentrated under reduced pressure to afford the product as a light yellow solid. Yield: 700 mg, 2.83 mmol, 89%. LCMS m/z 248.1 [M+H]$^+$. $^1$H NMR (400 MHz, CDCl$_3$) δ 9.20 (s, 1H), 8.52-8.45 (m, 2H), 7.17 (dd, J=7.6, 4.9 Hz, 1H), 3.14-3.04 (m, 8H).

Step 3. Synthesis of ethyl (6R)-6-{4-[3-(1,3,4-thiadiazol-2-yl)pyridin-2-yl]piperazin-1-yl}-2-azaspiro[3.4]octane-2-carboxylate (5)

A mixture of C12 (700 mg, 2.83 mmol), P3 (1.23 g, 4.43 mmol), and potassium carbonate (511 mg, 3.70 mmol) in acetonitrile (20 mL) was placed in a sealed vessel and stirred at 100° C. for 16 hours. The reaction mixture was then concentrated in vacuo and purified using silica gel chromatography (Gradient: 0% to 10% methanol in dichloromethane) to provide the product as a white solid. Yield: 400 mg, 0.933 mmol, 33%. LCMS m/z 429.2 [M+H]$^+$. $^1$H NMR (400 MHz, CDCl$_3$) δ 9.20 (s, 1H), 8.47-8.41 (m, 2H), 7.14 (dd, J=7.6, 4.9 Hz, 1H), 4.10 (q, J=7.1 Hz, 2H), 3.88 (AB quartet, $J_{AB}$=8.3 Hz, $\Delta_{\nu AB}$=21.7 Hz, 2H), 3.83-3.76 (m, 2H), 3.25-3.12 (br m, 4H), 2.73-2.55 (br m, 5H), 2.13 (dd, J=12.6, 7.0 Hz, 1H), 2.02-1.51 (m, 5H, assumed; partially obscured by water peak), 1.24 (t, J=7.1 Hz, 3H).

Examples 6 and 7

Ethyl (6R)-6-[4-(3-methoxypyridin-2-yl)piperazin-1-yl]-2-azaspiro[3.4]octane-2-carboxylate (6) and Ethyl (6S)-6-[4-(3-methoxypyridin-2-yl)piperazin-1-yl]-2-azaspiro[3.4]octane-2-carboxylate (7)

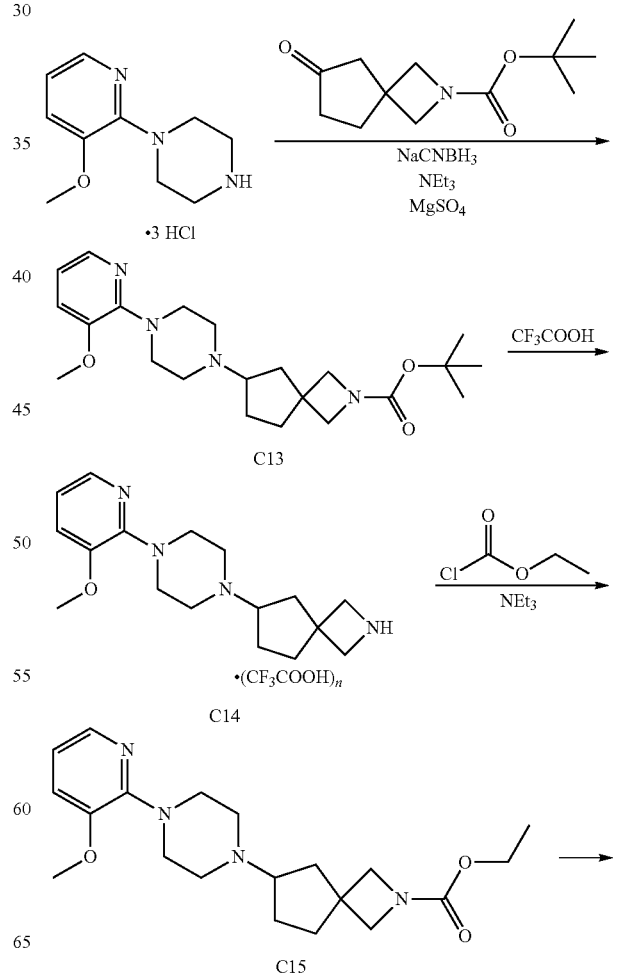

-continued

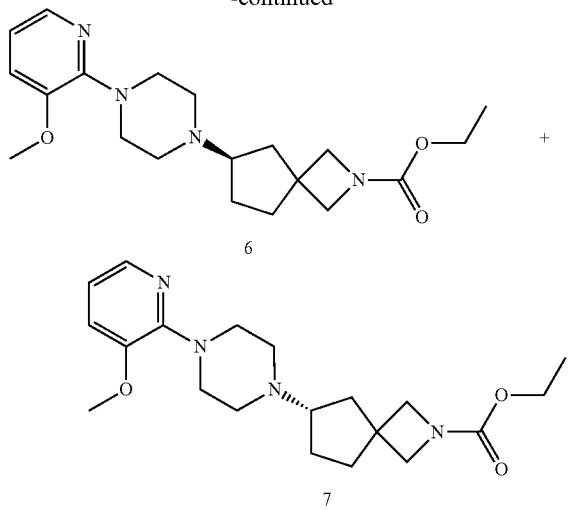

Step 1. Synthesis of tert-butyl 6-[4-(3-methoxypyridin-2-yl)piperazin-1-yl]-2-azaspiro[3.4]octane-2-carboxylate (C13)

A suspension of tert-butyl 6-oxo-2-azaspiro[3.4]octane-2-carboxylate (2.00 g, 8.88 mmol), 1-(3-methoxypyridin-2-yl)piperazine, trihydrochloride salt (2.71 g, 8.96 mmol), triethylamine (7.38 mL, 52.9 mmol), sodium cyanoborohydride (3.35 g, 53.3 mmol) and magnesium sulfate (3.21 g, 26.7 mmol) in ethanol (50 mL) was stirred at 45° C. for 16 hours. The reaction mixture was then concentrated to dryness in vacuo; silica gel chromatography (Eluent: 1:10 methanol/dichloromethane) afforded the product as a light yellow oil, which was used in the next step without purification. LCMS m/z 403.1 [M+H]$^+$.

Step 2. Synthesis of 6-[4-(3-methoxypyridin-2-yl)piperazin-1-yl]-2-azaspiro[3.4]octane, trifluoroacetate salt (C14)

Trifluoroacetic acid (20 mL) was added in a drop-wise manner to a solution of C13 (from the previous step; 58.88 mmol) in dichloromethane (80 mL). The reaction mixture was stirred at 10° C. for 2 hours, whereupon it was concentrated to dryness under reduced pressure, providing the product as a light yellow oil, which was taken directly into the following step. LCMS m/z 302.9 [M+H]$^+$.

Step 3. Synthesis of ethyl 6-[4-(3-methoxypyridin-2-yl)piperazin-1-yl]-2-azaspiro[3.4]octane-2-carboxylate (C15)

To a solution of C14 (from the previous step, 58.88 mmol) and triethylamine (12.3 mL, 88.2 mmol) in dichloromethane (100 mL) was added ethyl chloroformate (2.89 g, 26.6 mmol). The reaction mixture was stirred at 10° C. for 16 hours, whereupon it was concentrated to dryness in vacuo. Purification was carried out via silica gel chromatography (Gradient: 0% to 9% methanol in dichloromethane) followed by reversed-phase HPLC (Column: Phenomenex Gemini C18, 10 μm; Mobile phase A: 0.05% ammonium hydroxide in water; Mobile phase B: acetonitrile; Gradient: 25% to 44% B). The resulting material was then subjected once more to silica gel chromatography (ethyl acetate eluent, followed by a gradient of 0% to 9% methanol in dichloromethane) to provide the product as a white solid. Yield: 1.68 g, 4.49 mmol, 51% over 3 steps. LCMS m/z 375.2 [M+H]$^+$. $^1$H NMR (400 MHz, CD$_3$OD) δ 7.80 (dd, J=5.0, 1.5 Hz, 1H), 7.29 (dd, J=8.0, 1.0 Hz, 1H), 6.98 (dd, J=8.0, 5.0 Hz, 1H), 4.08 (q, J=7.0 Hz, 2H), 3.99-3.78 (m, 4H), 3.87 (s, 3H), 3.68-3.44 (br m, 4H), 3.41-3.3 (m, 1H, assumed; partially obscured by solvent peak), 3.28-3.11 (br m, 4H), 2.40 (dd, J=13.0, 8.0 Hz, 1H), 2.22-2.11 (m, 1H), 2.10-2.00 (m, 1H), 2.00-1.90 (m, 2H), 1.83-1.70 (m, 1H), 1.23 (t, J=7.0 Hz, 3H).

Step 4. Isolation of ethyl (6R)-6-[4-(3-methoxypyridin-2-yl)piperazin-1-yl]-2-azaspiro[3.4]octane-2-carboxylate (6) and ethyl (6S)-6-[4-(3-methoxypyridin-2-yl)piperazin-1-yl]-2-azaspiro[3.4]octane-2-carboxylate (7)

Separation of C15 (1.67 g, 4.46 mmol) into its component enantiomers was carried out via supercritical fluid chromatography {Column: Phenomenex Lux Amylose-1, 5 μm; Mobile phase: 4:1 carbon dioxide/[ethanol containing 0.2% (7 M ammonia in ethanol)]; Back pressure: 120 bar}. The first-eluting enantiomer was designated as 6, and the second-eluting enantiomer as 7. The indicated absolute configurations were assigned on the basis of X-ray structural determination carried out on the hydrochloride salt of 6 (see below).

6—Yield: 394 mg, 1.05 mmol, 24%. Retention time: 5.80 minutes {Analytical conditions. Column: Phenomenex Lux Amylose-1, 250×4.6 mm, 5 μm; Mobile phase A: carbon dioxide; Mobile phase B: [ethanol containing 0.2% (7 M ammonia in ethanol)]; Gradient: 5% for 1 minute, then 5% to 60% B over 8.0 minutes; Flow rate: 3.0 mL/minute; Back pressure: 120 bar}.

7—Yield: 453 mg, 1.21 mmol, 27%. LCMS m/z 375.3 [M+H]$^+$. $^1$H NMR (400 MHz, CDCl$_3$) δ 7.87 (br d, J=4.7 Hz, 1H), 7.03 (br d, J=7.8 Hz, 1H), 6.83 (dd, J=8.0, 4.9 Hz, 1H), 4.10 (q, J=7.2 Hz, 2H), 3.90 (d, half of AB quartet, J=8.6 Hz, 1H), 3.86-3.82 (m, 1H), 3.84 (s, 3H), 3.79 (AB quartet, J$_{AB}$=8.4 Hz, Δ$_{vAB}$=8.4 Hz, 2H), 3.47-3.39 (br m, 4H), 2.71-2.57 (br m, 5H), 2.14 (dd, J=12.9, 7.0 Hz, 1H), 1.99-1.81 (m, 3H), 1.77 (dd, J=12.5, 9.8 Hz, 1H), 1.67-1.55 (m, 1H), 1.24 (t, J=7.0 Hz, 3H). Retention time: 6.68 minutes (Analytical conditions identical to those used for 6). Conversion of 6 to its Hydrochloride Salt (6·HCl) for Single-Crystal X-Ray Structural Determination A solution of hydrogen chloride in 1,4-dioxane (4 M; 6.3 μL, 25 μmol) was added to a solution of 6 (9.5 mg, 25 μmol) in ethanol (254 μL) in a 1 dram vial. After the vial had been shaken by hand for 30 seconds, it was allowed to sit, uncovered, for 18 hours. At that point, the ethanol had evaporated, leaving small, needle-shaped crystals of 6·HCl, one of which was analyzed via single-crystal X-ray structure determination, as outlined below.
Single-Crystal X-Ray Structural Determination of 6·HCl
Single Crystal X-Ray Analysis Data collection was performed on a Bruker APEX diffractometer at −150° C. Data collection consisted of omega and phi scans.

The structure was solved by direct methods using SHELX software suite in the orthorhombic class space group P2$_1$2$_1$2$_1$. The structure was subsequently refined by the full-matrix least squares method. All non-hydrogen atoms were found and refined using anisotropic displacement parameters.

The hydrogen atoms located on nitrogen as proton acceptor were found from the Fourier difference map and refined with distances restrained. The hydrogen atoms were placed in calculated positions and were allowed to ride on their carrier atoms. The final refinement included isotropic displacement parameters for all hydrogen atoms.

Squeeze algorithm via Platon was applied to eliminate observed residual electron density of likely disordered ethyl acetate solvent sitting on a center of symmetry. The agreement factor improved by 1.7%.

Analysis of the absolute structure using likelihood methods (Hooft, 2008) was performed using PLATON (Spek). The results indicate that the absolute structure has been correctly assigned. The method calculates that the probability that the structure is correct is 1.000. The Hooft parameter is reported as 0.035 with an esd of 0.011.

The asymmetric unit comprised two molecules of protonated 6 ($2^+$), two chloride ions ($2^-$), and one molecule of water (half occupied). The final R-index was 5.3%. A final difference Fourier revealed no missing or misplaced electron density.

Pertinent crystal, data collection, and refinement information is summarized in Table A. Atomic coordinates, bond lengths, bond angles, and displacement parameters are listed in Tables B-D.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE A

Crystal data and structure refinement for 6•HCl.

| | |
|---|---|
| Empirical formula | $C_{20}H_{32}N_4O_{3.5}Cl$ |
| Formula weight | 419.95 |
| Temperature | 123(2) K |
| Wavelength | 1.54178 Å |
| Crystal system | Orthorhombic |
| Space group | $P2_12_12_1$ |
| Unit cell dimensions | a = 7.0692(2) Å  α = 90° |
| | b = 18.3143(4) Å  β = 90° |
| | c = 35.5680(8) Å  γ = 90° |
| Volume | 4604.90(19) Å$^3$ |
| Z | 8 |
| Density (calculated) | 1.209 Mg/m$^3$ |
| Absorption coefficient | 1.705 mm$^{-1}$ |
| F(000) | 1792 |
| Crystal size | 0.160 × 0.140 × 0.040 mm$^3$ |
| Theta range for data collection | 2.484 to 68.745° |
| Index ranges | −8 <= h <= 8, −21 <= k <= 22, −42 <= l <= 42 |
| Reflections collected | 52301 |
| Independent reflections | 8415 [$R_{int}$ = 0.0833] |
| Completeness to theta = 67.679° | 100.0% |
| Refinement method | Full-matrix least-squares on F$^2$ |
| Data/restraints/parameters | 8415/2/524 |
| Goodness-of-fit on F$^2$ | 0.997 |
| Final R indices [I>2σ(I)] | R1 = 0.0531, wR2 = 0.1262 |
| R indices (all data) | R1 = 0.0695, wR2 = 0.1342 |
| Absolute structure parameter | 0.035(11) |
| Extinction coefficient | n/a |
| Largest diff. peak and hole | 0.454 and −0.281 e.Å$^{-3}$ |

TABLE B

Atomic coordinates (×10$^4$) and equivalent isotropic displacement parameters (Å$^2$ × 10$^3$) for 6•HCl. U(eq) is defined as one-third of the trace of the orthogonalized U$^{ij}$ tensor.

| | x | y | z | U(eq) |
|---|---|---|---|---|
| Cl(1) | 10393(2) | 8029(1) | 7707(1) | 38(1) |
| Cl(2) | 4410(2) | 5729(1) | 7217(1) | 38(1) |
| N(1) | −89(6) | 6045(2) | 8702(1) | 40(1) |
| N(2) | −240(5) | 5431(2) | 8129(1) | 29(1) |
| N(3) | 188(5) | 5589(2) | 7322(1) | 23(1) |
| N(4) | 1284(7) | 6561(3) | 5832(1) | 52(1) |
| N(5) | 4825(5) | 2854(2) | 8717(1) | 35(1) |
| N(6) | 4757(5) | 3402(2) | 8132(1) | 28(1) |
| N(7) | 5288(5) | 3142(2) | 7333(1) | 26(1) |
| N(8) | 4441(8) | 4052(3) | 5849(1) | 58(1) |
| O(1) | −562(5) | 4113(2) | 8526(1) | 40(1) |
| O(2) | 664(8) | 6759(3) | 5219(1) | 86(2) |
| O(3) | 3569(7) | 6414(3) | 5416(1) | 68(1) |
| O(4) | 4476(5) | 4777(2) | 8501(1) | 36(1) |
| O(5) | 5152(8) | 4376(3) | 5246(1) | 81(2) |
| O(6) | 2155(8) | 4430(3) | 5476(1) | 73(1) |
| O(1W) | 9873(7) | 2630(2) | 6413(1) | 78(1) |
| C(1) | −350(7) | 4742(3) | 8727(1) | 36(1) |
| C(2) | −408(8) | 3438(3) | 8723(2) | 48(1) |
| C(3) | −342(7) | 4772(3) | 9115(1) | 44(1) |
| C(4) | −231(8) | 5440(3) | 9295(1) | 53(1) |
| C(5) | −139(8) | 6056(3) | 9079(1) | 45(1) |
| C(6) | −180(6) | 5408(3) | 8522(1) | 33(1) |
| C(7) | 845(6) | 4904(2) | 7905(1) | 29(1) |
| C(8) | 33(6) | 4869(2) | 7515(1) | 29(1) |
| C(9) | −767(6) | 6154(2) | 7556(1) | 29(1) |
| C(10) | −58(7) | 6160(2) | 7960(1) | 30(1) |
| C(11) | 137(6) | 4964(2) | 6689(1) | 31(1) |
| C(12) | −437(8) | 5233(2) | 6301(1) | 37(1) |
| C(13) | 148(7) | 6039(2) | 6306(1) | 33(1) |
| C(14) | −263(7) | 6279(2) | 6713(1) | 35(1) |
| C(15) | −649(7) | 5572(2) | 6933(1) | 28(1) |
| C(16) | 2171(7) | 6173(3) | 6154(1) | 41(1) |
| C(17) | −623(8) | 6504(3) | 5979(1) | 44(1) |
| C(18) | 1720(10) | 6591(4) | 5468(2) | 61(2) |
| C(19) | 4199(12) | 6547(6) | 5033(2) | 103(3) |
| C(20) | 6119(11) | 6413(5) | 5019(2) | 92(3) |
| C(21) | 4643(6) | 4160(2) | 8713(1) | 32(1) |
| C(22) | 4652(7) | 5465(2) | 8686(1) | 41(1) |
| C(23) | 4631(7) | 4162(3) | 9100(1) | 40(1) |
| C(24) | 4699(8) | 3508(3) | 9300(1) | 45(1) |
| C(25) | 4763(7) | 2877(3) | 9097(1) | 44(1) |
| C(26) | 4782(6) | 3473(2) | 8526(1) | 29(1) |
| C(27) | 5791(6) | 3919(2) | 7892(1) | 31(1) |
| C(28) | 5009(6) | 3885(2) | 7494(1) | 28(1) |
| C(29) | 4384(7) | 2595(2) | 7587(1) | 30(1) |
| C(30) | 5060(6) | 2666(2) | 7988(1) | 32(1) |
| C(31) | 4556(6) | 3090(2) | 6938(1) | 29(1) |
| C(32) | 5513(6) | 3619(2) | 6667(1) | 34(1) |
| C(33) | 5014(8) | 3304(2) | 6283(1) | 41(1) |
| C(34) | 5028(8) | 2479(2) | 6339(1) | 46(1) |
| C(35) | 4957(7) | 2340(2) | 6764(1) | 35(1) |
| C(36) | 3199(8) | 3641(3) | 6112(1) | 49(1) |
| C(38) | 4012(11) | 4292(3) | 5496(2) | 63(2) |
| C(37) | 6098(9) | 3636(3) | 5945(1) | 50(1) |
| C(39) | 1589(12) | 4712(5) | 5107(2) | 83(2) |
| C(40) | −417(15) | 4838(6) | 5139(2) | 110(3) |

TABLE C

| Bond lengths [Å] and angles [°] for 6•HCl. | |
|---|---|
| N(1)—C(6) | 1.334(6) |
| N(1)—C(5) | 1.342(6) |
| N(2)—C(6) | 1.397(5) |
| N(2)—C(7) | 1.469(5) |
| N(2)—C(10) | 1.469(5) |
| N(3)—C(8) | 1.489(5) |
| N(3)—C(9) | 1.490(5) |
| N(3)—C(15) | 1.508(5) |
| N(4)—C(18) | 1.334(7) |
| N(4)—C(17) | 1.449(7) |
| N(4)—C(16) | 1.485(6) |
| N(5)—C(26) | 1.323(5) |
| N(5)—C(25) | 1.351(6) |
| N(6)—C(26) | 1.407(5) |
| N(6)—C(30) | 1.458(5) |
| N(6)—C(27) | 1.470(5) |
| N(7)—C(28) | 1.489(5) |
| N(7)—C(29) | 1.493(5) |
| N(7)—C(31) | 1.501(5) |
| N(8)—C(38) | 1.364(7) |
| N(8)—C(37) | 1.438(7) |
| N(8)—C(36) | 1.488(7) |
| O(1)—C(1) | 1.364(6) |
| O(1)—C(2) | 1.425(5) |
| O(2)—C(18) | 1.200(8) |
| O(3)—C(18) | 1.359(8) |
| O(3)—C(19) | 1.453(7) |
| O(4)—C(21) | 1.364(5) |
| O(4)—C(22) | 1.426(5) |
| O(5)—C(38) | 1.211(7) |
| O(6)—C(38) | 1.339(8) |
| O(6)—C(39) | 1.465(7) |
| C(1)—C(3) | 1.383(6) |
| C(1)—C(6) | 1.425(6) |
| C(3)—C(4) | 1.384(8) |
| C(4)—C(5) | 1.367(7) |
| C(7)—C(8) | 1.502(6) |
| C(9)—C(10) | 1.521(5) |
| C(11)—C(15) | 1.516(6) |
| C(11)—C(12) | 1.522(6) |
| C(12)—C(13) | 1.534(6) |
| C(13)—C(17) | 1.542(6) |
| C(13)—C(14) | 1.539(6) |
| C(13)—C(16) | 1.549(7) |
| C(14)—C(15) | 1.536(6) |
| C(19)—C(20) | 1.380(12) |
| C(21)—C(23) | 1.375(6) |
| C(21)—C(26) | 1.427(6) |
| C(23)—C(24) | 1.394(7) |
| C(24)—C(25) | 1.363(7) |
| C(27)—C(28) | 1.519(6) |
| C(29)—C(30) | 1.509(6) |
| C(31)—C(32) | 1.525(6) |
| C(31)—C(35) | 1.532(6) |
| C(32)—C(33) | 1.522(6) |
| C(33)—C(34) | 1.523(7) |
| C(33)—C(36) | 1.549(7) |
| C(33)—C(37) | 1.551(7) |
| C(34)—C(35) | 1.533(6) |
| C(39)—C(40) | 1.440(12) |
| C(6)—N(1)—C(5) | 119.5(4) |
| C(6)—N(2)—C(7) | 120.5(3) |
| C(6)—N(2)—C(10) | 115.7(3) |
| C(7)—N(2)—C(10) | 109.2(3) |
| C(8)—N(3)—C(9) | 108.9(3) |
| C(8)—N(3)—C(15) | 112.1(3) |
| C(9)—N(3)—C(15) | 110.5(3) |
| C(18)—N(4)—C(17) | 124.5(5) |
| C(18)—N(4)—C(16) | 132.1(6) |
| C(17)—N(4)—C(16) | 94.7(4) |
| C(26)—N(5)—C(25) | 119.1(4) |
| C(26)—N(6)—C(30) | 115.7(3) |
| C(26)—N(6)—C(27) | 120.9(3) |
| C(30)—N(6)—C(27) | 108.5(3) |
| C(28)—N(7)—C(29) | 108.8(3) |
| C(28)—N(7)—C(31) | 112.0(3) |
| C(29)—N(7)—C(31) | 112.1(3) |
| C(38)—N(8)—C(37) | 124.7(5) |
| C(38)—N(8)—C(36) | 127.6(6) |
| C(37)—N(8)—C(36) | 93.6(4) |
| C(1)—O(1)—C(2) | 117.8(3) |
| C(18)—O(3)—C(19) | 112.5(6) |
| C(21)—O(4)—C(22) | 117.9(3) |
| C(38)—O(6)—C(39) | 112.6(5) |
| O(1)—C(1)—C(3) | 123.8(4) |
| O(1)—C(1)—C(6) | 117.6(4) |
| C(3)—C(1)—C(6) | 118.5(4) |
| C(1)—C(3)—C(4) | 119.8(5) |
| C(5)—C(4)—C(3) | 118.2(4) |
| N(1)—C(5)—C(4) | 123.4(5) |
| N(1)—C(6)—N(2) | 117.1(4) |
| N(1)—C(6)—C(1) | 120.5(4) |
| N(2)—C(6)—C(1) | 122.3(4) |
| N(2)—C(7)—C(8) | 109.3(3) |
| N(3)—C(8)—C(7) | 111.1(3) |
| N(3)—C(9)—C(10) | 112.5(3) |
| N(2)—C(10)—C(9) | 110.5(3) |
| C(15)—C(11)—C(12) | 100.6(3) |
| C(11)—C(12)—C(13) | 103.2(3) |
| C(12)—C(13)—C(17) | 115.3(4) |
| C(12)—C(13)—C(14) | 103.6(3) |
| C(17)—C(13)—C(14) | 119.1(4) |
| C(12)—C(13)—C(16) | 113.3(4) |
| C(17)—C(13)—C(16) | 88.6(4) |
| C(14)—C(13)—C(16) | 117.2(4) |
| C(15)—C(14)—C(13) | 105.8(3) |
| N(3)—C(15)—C(11) | 113.4(3) |
| N(3)—C(15)—C(14) | 112.4(3) |
| C(11)—C(15)—C(14) | 105.2(3) |
| N(4)—C(16)—C(13) | 87.4(4) |
| N(4)—C(17)—C(13) | 89.0(4) |
| O(2)—C(18)—N(4) | 125.8(7) |
| O(2)—C(18)—O(3) | 124.0(6) |
| N(4)—C(18)—O(3) | 110.2(5) |
| C(20)—C(19)—O(3) | 107.8(7) |
| O(4)—C(21)—C(23) | 123.4(4) |
| O(4)—C(21)—C(26) | 118.5(4) |
| C(23)—C(21)—C(26) | 118.1(4) |
| C(21)—C(23)—C(24) | 120.4(5) |
| C(25)—C(24)—C(23) | 117.4(4) |
| N(5)—C(25)—C(24) | 123.8(4) |
| N(5)—C(26)—N(6) | 115.7(4) |
| N(5)—C(26)—C(21) | 121.1(4) |
| N(6)—C(26)—C(21) | 123.1(4) |
| N(6)—C(27)—C(28) | 109.5(3) |
| N(7)—C(28)—C(27) | 110.4(3) |
| N(7)—C(29)—C(30) | 112.3(3) |
| N(6)—C(30)—C(29) | 111.4(3) |
| N(7)—C(31)—C(32) | 113.5(3) |
| N(7)—C(31)—C(35) | 111.8(3) |
| C(32)—C(31)—C(35) | 103.4(3) |
| C(33)—C(32)—C(31) | 102.8(4) |
| C(32)—C(33)—C(34) | 105.0(4) |
| C(32)—C(33)—C(36) | 113.1(4) |
| C(34)—C(33)—C(36) | 116.9(5) |
| C(32)—C(33)—C(37) | 115.6(4) |
| C(34)—C(33)—C(37) | 119.1(4) |
| C(36)—C(33)—C(37) | 87.0(4) |
| C(33)—C(34)—C(35) | 107.0(4) |
| C(31)—C(35)—C(34) | 104.8(3) |
| N(8)—C(36)—C(33) | 87.4(4) |
| O(5)—C(38)—O(6) | 126.0(6) |
| O(5)—C(38)—N(8) | 124.8(7) |
| O(6)—C(38)—N(8) | 109.2(5) |
| N(8)—C(37)—C(33) | 89.4(4) |
| C(40)—C(39)—O(6) | 104.8(7) |

Symmetry transformations used to generate equivalent atoms.

TABLE D

Anisotropic displacement parameters (Å² × 10³) for 6•HCl. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| Cl(1) | 25(1) | 30(1) | 61(1) | 2(1) | 0(1) | −2(1) |
| Cl(2) | 23(1) | 30(1) | 63(1) | 2(1) | 3(1) | −2(1) |
| N(1) | 44(2) | 46(2) | 29(2) | −6(2) | 3(2) | 7(2) |
| N(2) | 33(2) | 31(2) | 23(2) | 2(1) | 1(2) | −1(2) |
| N(3) | 22(2) | 24(2) | 25(2) | −2(1) | 1(1) | −1(1) |
| N(4) | 71(3) | 62(3) | 24(2) | 4(2) | 1(2) | −10(2) |
| N(5) | 34(2) | 38(2) | 32(2) | 11(2) | 4(2) | 0(2) |
| N(6) | 33(2) | 25(2) | 25(2) | 5(1) | −2(2) | 0(2) |
| N(7) | 24(2) | 23(2) | 31(2) | 2(1) | −2(2) | −1(2) |
| N(8) | 83(3) | 58(3) | 33(2) | 10(2) | 5(2) | 7(3) |
| O(1) | 45(2) | 38(2) | 37(2) | 10(1) | 2(2) | −1(2) |
| O(2) | 101(4) | 128(4) | 29(2) | 14(2) | −10(2) | −33(3) |
| O(3) | 84(3) | 84(3) | 35(2) | −12(2) | 9(2) | −35(3) |
| O(4) | 49(2) | 31(2) | 28(2) | −1(1) | 1(2) | 4(2) |
| O(5) | 123(4) | 85(3) | 34(2) | 12(2) | 19(3) | 2(3) |
| O(6) | 106(4) | 78(3) | 35(2) | 5(2) | −6(2) | 20(3) |
| O(1W) | 82(3) | 71(3) | 82(3) | 19(2) | 13(3) | 2(3) |
| C(1) | 29(2) | 47(3) | 31(2) | 5(2) | 4(2) | 4(2) |
| C(2) | 47(3) | 44(3) | 52(3) | 21(2) | −2(3) | −5(3) |
| C(3) | 42(3) | 61(3) | 31(2) | 14(2) | 4(2) | 5(3) |
| C(4) | 55(3) | 80(4) | 23(2) | −1(2) | 2(2) | 8(3) |
| C(5) | 50(3) | 51(3) | 34(2) | −7(2) | 1(2) | 7(3) |
| C(6) | 29(2) | 42(2) | 28(2) | 2(2) | 0(2) | 4(2) |
| C(7) | 32(2) | 25(2) | 29(2) | 1(2) | 3(2) | 4(2) |
| C(8) | 36(2) | 22(2) | 27(2) | 1(2) | 4(2) | −1(2) |
| C(9) | 33(2) | 26(2) | 28(2) | −2(2) | 3(2) | 5(2) |
| C(10) | 38(3) | 26(2) | 27(2) | −2(2) | 0(2) | 0(2) |
| C(11) | 34(2) | 30(2) | 28(2) | 1(2) | 1(2) | −1(2) |
| C(12) | 44(3) | 36(2) | 31(2) | −4(2) | −1(2) | −1(2) |
| C(13) | 41(3) | 33(2) | 25(2) | 1(2) | −2(2) | 4(2) |
| C(14) | 44(3) | 30(2) | 30(2) | 1(2) | 1(2) | 8(2) |
| C(15) | 29(2) | 32(2) | 22(2) | −1(2) | −4(2) | −2(2) |
| C(16) | 47(3) | 46(3) | 29(2) | 3(2) | 0(2) | −1(2) |
| C(17) | 63(3) | 38(2) | 30(2) | 1(2) | −7(2) | −1(3) |
| C(18) | 86(5) | 71(4) | 27(3) | 4(3) | −4(3) | −30(4) |
| C(19) | 87(6) | 183(9) | 38(4) | −28(5) | 15(3) | −50(6) |
| C(20) | 82(5) | 155(6) | 37(3) | −22(4) | 10(3) | −30(5) |
| C(21) | 28(2) | 37(3) | 33(2) | 5(2) | 2(2) | −1(2) |
| C(22) | 41(3) | 37(3) | 45(3) | −4(2) | 2(2) | 5(2) |
| C(23) | 39(3) | 53(3) | 29(2) | 1(2) | 4(2) | 1(3) |
| C(24) | 46(3) | 65(3) | 24(2) | 10(2) | 2(2) | 2(3) |
| C(25) | 42(3) | 50(3) | 39(3) | 20(2) | 2(2) | −3(3) |
| C(26) | 25(2) | 31(2) | 31(2) | 5(2) | 2(2) | −4(2) |
| C(27) | 35(2) | 26(2) | 32(2) | 1(2) | 1(2) | −4(2) |
| C(28) | 34(2) | 23(2) | 29(2) | 2(2) | 2(2) | 1(2) |
| C(29) | 27(2) | 24(2) | 39(2) | 5(2) | 1(2) | −2(2) |
| C(30) | 33(2) | 28(2) | 34(2) | 7(2) | 0(2) | −2(2) |
| C(31) | 26(2) | 33(2) | 28(2) | −5(2) | −4(2) | 2(2) |
| C(32) | 42(3) | 33(2) | 28(2) | 2(2) | −2(2) | 1(2) |
| C(33) | 56(3) | 37(2) | 29(2) | −4(2) | −1(2) | 3(2) |
| C(34) | 63(4) | 35(2) | 41(3) | −10(2) | 0(3) | 5(2) |
| C(35) | 35(3) | 33(2) | 37(2) | −4(2) | −2(2) | 1(2) |
| C(36) | 60(3) | 53(3) | 33(3) | −1(3) | 0(2) | 8(3) |
| C(38) | 91(5) | 48(3) | 49(4) | 0(3) | 5(3) | 8(4) |
| C(37) | 71(4) | 46(3) | 34(3) | 0(2) | 7(2) | 4(3) |
| C(39) | 104(6) | 95(6) | 50(4) | 18(4) | −15(4) | 18(5) |
| C(40) | 113(7) | 153(8) | 66(5) | 0(5) | −11(5) | 20(7) |

Alternate Synthesis of Example 6

Ethyl (6R)-6-[4-(3-methoxypyridin-2-yl)piperazin-1-yl]-2-azaspiro[3.4]octane-2-carboxylate (6)

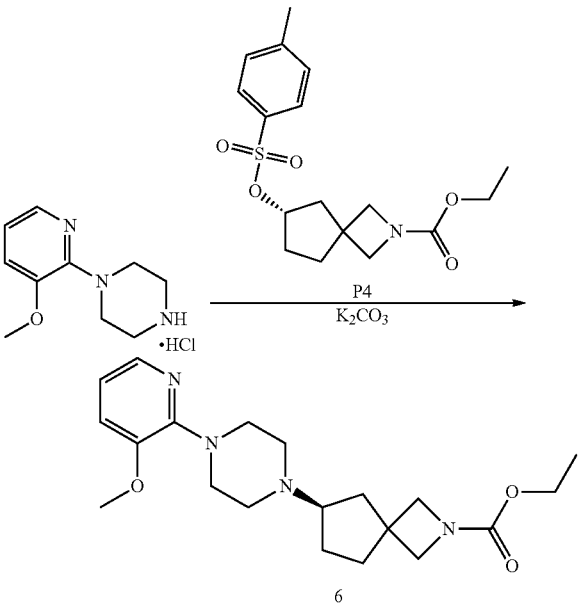

1-(3-Methoxypyridin-2-yl)piperazine, hydrochloride salt (130 mg, 0.566 mmol), P4 (240 mg, 0.679 mmol), potassium carbonate (313 mg, 2.26 mmol), and acetonitrile (2.3 mL) were placed in a sealed vessel and heated at 90° C. overnight. After the reaction mixture had cooled to room temperature, it was adsorbed onto silica gel and purified via silica gel chromatography (Gradient: 0% to 20% methanol in dichloromethane, providing the product as a light brown oil. Yield: 80 mg, 0.21 mmol, 37%. LCMS m/z 375.1 [M+H]⁺. ¹H NMR (400 MHz, CDCl₃) δ 7.88 (dd, J=4.9, 1.4 Hz, 1H), 7.03 (dd, J=7.8, 1.2 Hz, 1H), 6.84 (dd, J=8.0, 4.9 Hz, 1H), 4.10 (q, J=7.2 Hz, 2H), 3.91 (d, half of AB quartet, J=8.2 Hz, 1H), 3.87-3.83 (m, 1H), 3.85 (s, 3H), 3.80 (AB quartet, $J_{AB}$=8.2 Hz, $\Delta_{\nu AB}$=8.4 Hz, 2H), 3.48-3.39 (br m, 4H), 2.69-2.56 (br m, 5H), 2.15 (dd, J=12.9, 7.0 Hz, 1H), 2.00-1.80 (m, 3H), 1.76 (dd, J=12.7, 9.6 Hz, 1H), 1.65-1.53 (m, 1H, assumed; partially obscured by water peak), 1.24 (t, J=7.0 Hz, 3H).

The indicated absolute configuration of this synthesized material (6—Alternate Synthesis) was established via comparison with the material (6—X-ray preparation) used for preparation of the X-ray crystal structure sample described above, as follows. The racemate C15 was examined using supercritical fluid chromatography {Column: Phenomenex Lux Amylose-1, 250×4.6 mm, 5 μm; Mobile phase A: carbon dioxide; Mobile phase B: [methanol containing 0.2% (7 M ammonia in methanol)]; Gradient: 5% B for 1.0 minute, then 5% to 60% B over 8.0 minutes; Flow rate: 3.0 mL/minute; Back pressure: 120 bar}. Two peaks were observed: one at 5.82 minutes, and one at 6.54 minutes, for the two enantiomers. Under identical conditions, 6—Alternate Synthesis gave a retention time of 5.83 minutes, and 6—X-ray preparation gave a retention time of 5.83 minutes, establishing that the two samples possess the same absolute stereochemistry.

Example 8

Ethyl (6R)-6-{4-[3-(pyrazin-2-yl)pyridin-2-yl]piperazin-1-yl}-2-azaspiro[3.4]octane-2-carboxylate (8)

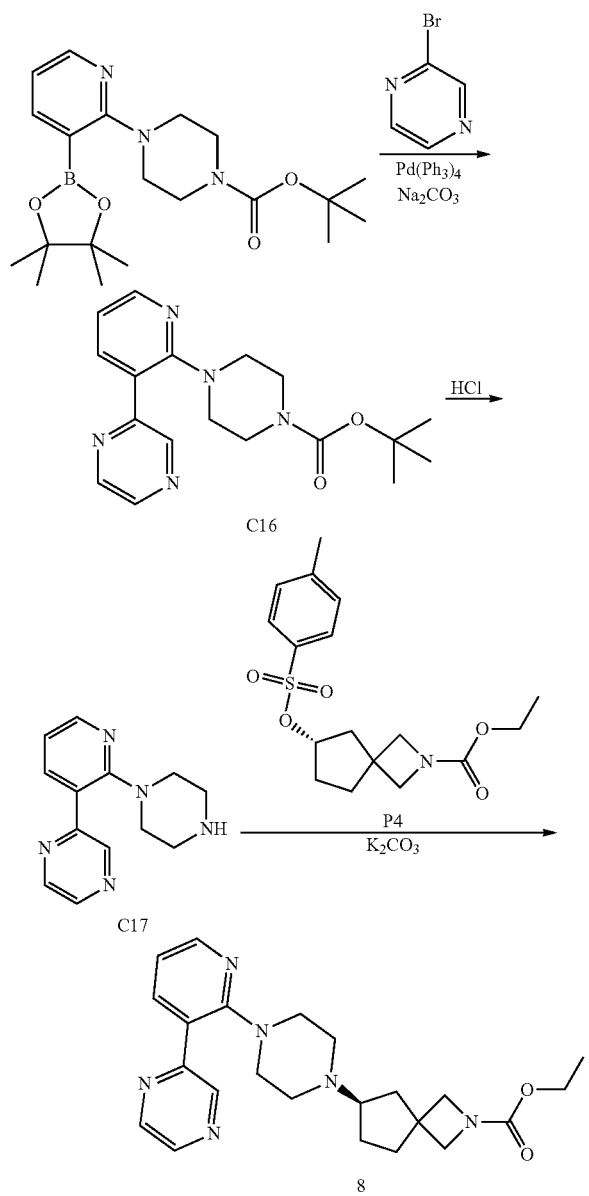

Step 1. Synthesis of tert-butyl 4-[3-(pyrazin-2-yl)pyridin-2-yl]piperazine-1-carboxylate (C16)

A mixture of tert-butyl 4-[3-(4,4,5,5-tetramethyl-1,3,2-dioxaborolan-2-yl)pyridin-2-yl]piperazine-1-carboxylate (6.00 g, 15.4 mmol), 2-bromopyrazine (2.7 g, 17 mmol), tetrakis(triphenylphosphine)palladium(0) (1.78 g, 1.54 mmol), and potassium carbonate (6.39 g, 46.2 mmol) in a mixture of toluene (80 mL), ethanol (30 mL), and water (3 mL) was stirred at 100° C. for 16 hours. The reaction mixture was then concentrated in vacuo, and the residue was purified via chromatography on silica gel (Gradient: 0% to 50% ethyl acetate in petroleum ether) to afford the product as a yellow gum. Yield: 5.00 g, 14.6 mmol, 95%. LCMS m/z 342.2 [M+H]$^+$. $^1$H NMR (400 MHz, CDCl$_3$) δ 9.22 (br s, 1H), 8.68 (dd, J=2.4, 1.5 Hz, 1H), 8.51 (d, J=2.4 Hz, 1H), 8.35 (dd, J=4.9, 1.7 Hz, 1H), 7.90 (dd, J=7.6, 1.7 Hz, 1H), 7.06 (dd, J=7.6, 4.9 Hz, 1H), 3.46-3.39 (m, 4H), 3.16-3.07 (br m, 4H), 1.45 (s, 9H).

Step 2. Synthesis of 2-[2-(piperazin-1-yl)pyridin-3-yl]pyrazine (C17)

A mixture of C16 (5.30 g, 15.5 mmol) and a solution of hydrogen chloride in 1,4-dioxane (4 M; 15.5 mL, 62 mmol) in dichloromethane (60 mL) and methanol (20 mL) was stirred at room temperature for 2 hours, and subsequently heated at 40° C. for 1 hour. After removal of solvent in vacuo, the residue was dissolved in methanol (100 mL), treated with potassium carbonate (12.0 g, 86.8 mmol), and stirred at room temperature for 1 hour. The mixture was concentrated under reduced pressure, and the residue was purified using silica gel chromatography (Gradient: 0% to 10% methanol in dichloromethane) to afford the product. Yield: 2.90 g, 12.0 mmol, 77%. LCMS m/z 242.2 [M+H]$^+$. $^1$H NMR (400 MHz, DMSO-d$_6$) δ 9.18 (d, J=1.7 Hz, 1H), 8.74 (dd, J=2.6, 1.6 Hz, 1H), 8.57 (d, J=2.7 Hz, 1H), 8.30 (dd, J=4.9, 2.0 Hz, 1H), 7.85 (dd, J=7.6, 2.0 Hz, 1H), 7.07 (dd, J=7.5, 4.8 Hz, 1H), 2.95-2.90 (m, 4H), 2.67-2.62 (m, 4H).

Step 3. Synthesis of ethyl (6R)-6-{4-[3-(pyrazin-2-yl)pyridin-2-yl]piperazin-1-yl}-2-azaspiro[3.4]octane-2-carboxylate (8)

A mixture of C17 (2.50 g, 10.4 mmol), P4 (5.13 g, 14.5 mmol), and potassium carbonate (4.3 g, 31.1 mmol) in acetonitrile (25 mL) was placed in a sealed vessel and stirred at 100° C. for 48 hours. After removal of solvent in vacuo, the residue was diluted with water (150 mL) and extracted with ethyl acetate (3×100 mL). The combined organic layers were dried over sodium sulfate, filtered, concentrated in vacuo, and purified via silica gel chromatography (Gradient: 0% to 10% methanol in dichloromethane) to afford the product as a yellow gum. Yield: 2.90 g, 6.86 mmol, 66%. LCMS m/z 423.2 [M+H]$^+$. $^1$H NMR (400 MHz, CDCl$_3$) δ 9.23 (br s, 1H), 8.66 (dd, J=2.4, 1.5 Hz, 1H), 8.48 (d, J=2.7 Hz, 1H), 8.33 (dd, J=4.8, 1.8 Hz, 1H), 7.88 (dd, J=7.5, 1.8 Hz, 1H), 7.03 (dd, J=7.3, 4.9 Hz, 1H), 4.10 (q, J=7.1 Hz, 2H), 3.85 (AB quartet, downfield doublet is broadened, $J_{AB}$=8.3 Hz, $\Delta_{vAB}$=22.7 Hz, 2H), 3.79-3.74 (m, 2H), 3.32-3.09 (br m, 4H), 2.69-2.38 (br m, 5H), 2.10 (dd, J=12.5, 6.8 Hz, 1H), 2.01-1.46 (m, 5H, assumed; partially obscured by water peak), 1.24 (t, J=7.1 Hz, 3H).

Example 9

Ethyl (6R)-6-{4-[3-(4-methyl-1H-pyrazol-1-yl)pyridin-2-yl]piperazin-1-yl}-2-azaspiro[3.4]octane-2-carboxylate (9)

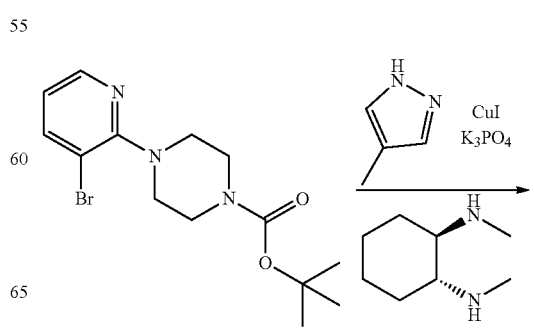

-continued

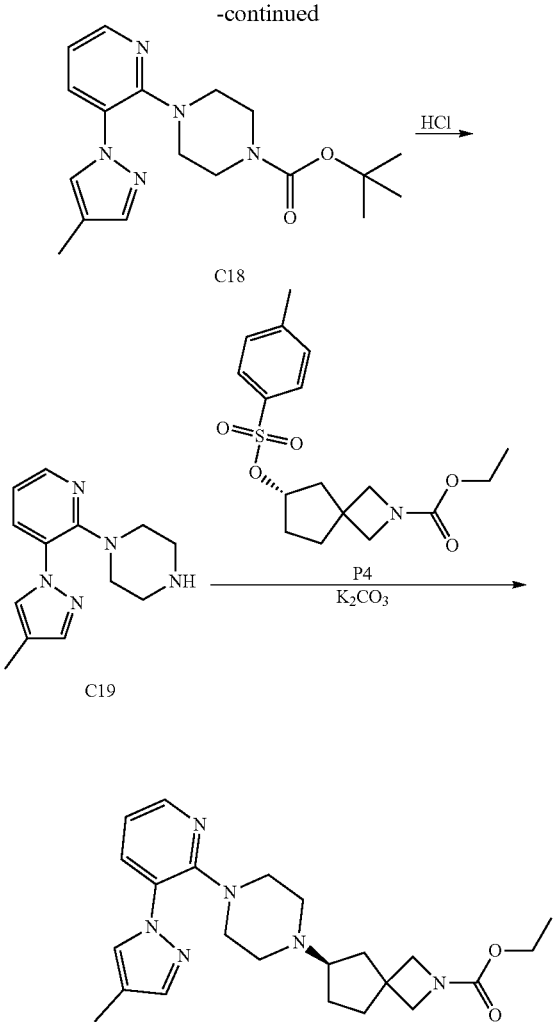

Step 1. Synthesis of tert-butyl 4-[3-(4-methyl-1H-pyrazol-1-yl)pyridin-2-yl]piperazine-1-carboxylate (C18)

A mixture of tert-butyl 4-(3-bromopyridin-2-yl)piperazine-1-carboxylate (400 mg, 1.17 mmol), 4-methyl-1H-pyrazole (144 mg, 1.75 mmol), copper(I) iodide (22 mg, 0.12 mmol), (1R,2R)—N,N'-dimethylcyclohexane-1,2-diamine (34 mg, 0.24 mmol), and potassium phosphate (746 mg, 3.51 mmol) in 1-methylpyrrolidin-2-one (4 mL) was placed in a sealed vessel and stirred at 140° C. for 16 hours. The reaction mixture was concentrated in vacuo, and the residue was subjected to silica gel chromatography (Gradient: 0% to 100% ethyl acetate in petroleum ether), affording the product as a light yellow solid (160 mg), which was used directly in the following step. By $^1$H NMR analysis, this material was not entirely pure. LCMS m/z 344.2 [M+H]$^+$. $^1$H NMR (400 MHz, CDCl$_3$), product peaks only: δ 8.24 (dd, J=4.9, 1.7 Hz, 1H), 7.78-7.76 (m, 1H), 7.71 (dd, J=7.8, 1.7 Hz, 1H), 7.54 (br s, 1H), 6.97 (dd, J=7.7, 4.8 Hz, 1H), 3.46-3.38 (m, 4H), 2.97-2.89 (m, 4H), 2.16 (s, 3H), 1.46 (s, 9H).

Step 2. Synthesis of 1-[3-(4-methyl-1H-pyrazol-1-yl)pyridin-2-yl]piperazine (C19)

A mixture of C18 (from the previous step; 160 mg, 50.466 mmol) and a solution of hydrogen chloride in 1,4-dioxane (4 M; 0.5 mL, 2 mmol) in dichloromethane (10 mL) was stirred at room temperature for 3 hours, whereupon it was concentrated in vacuo. The residue was dissolved in methanol (20 mL), treated with potassium carbonate (200 mg, 1.45 mmol), stirred at room temperature for 20 minutes, and concentrated under reduced pressure. Purification via silica gel chromatography (Gradient: 0% to 70% methanol in dichloromethane) provided the product as a light yellow solid. Yield: 60 mg, 0.25 mmol, 21% over two steps. LCMS m/z 244.2 [M+H]$^+$. $^1$H NMR (400 MHz, CDCl$_3$) δ 8.24 (dd, J=4.8, 1.6 Hz, 1H), 7.70 (dd, J=7.6, 1.7 Hz, 1H), 7.66 (br s, 1H), 7.54 (br s, 1H), 7.01 (dd, J=7.6, 4.9 Hz, 1H), 3.27-3.20 (m, 4H), 3.16-3.08 (m, 4H), 2.17 (s, 3H).

Step 3. Synthesis of ethyl (6R)-6-{4-[3-(4-methyl-1H-pyrazol-1-yl)pyridin-2-yl]piperazin-1-yl}-2-azaspiro[3.4]octane-2-carboxylate (9)

A mixture of C19 (60 mg, 0.25 mmol), P4 (131 mg, 0.371 mmol), and potassium carbonate (102 mg, 0.738 mmol) in acetonitrile (3 mL) was placed in a sealed vessel and stirred at 100° C. for 48 hours. After removal of solvent in vacuo, the residue was purified via chromatography on silica gel (Gradient: 0% to 20% methanol in dichloromethane), followed by reversed-phase HPLC (Column: Waters XBridge C18, 5 μm; Mobile phase A: water containing 0.05% ammonium hydroxide; Mobile phase B: acetonitrile; Gradient: 40% to 50% B). The product was isolated as a light yellow solid. Yield: 25 mg, 59 μmol, 24%. LCMS m/z 425.3 [M+H]$^+$. $^1$H NMR (400 MHz, CDCl$_3$) δ 8.23 (dd, J=4.8, 1.8 Hz, 1H), 7.73 (br s, 1H), 7.68 (dd, J=7.8, 1.7 Hz, 1H), 7.52 (br s, 1H), 6.93 (dd, J=7.7, 4.8 Hz, 1H), 4.10 (q, J=7.1 Hz, 2H), 3.86 (AB quartet, downfield doublet is broadened, J$_{AB}$=8.3 Hz, Δ$_{vAB}$=21.4 Hz, 2H), 3.78 (AB quartet, J$_{AB}$=8.3 Hz, Δ$_{vAB}$=6.0 Hz, 2H), 3.09-2.94 (br m, 4H), 2.62-2.39 (br m, 5H), 2.17 (s, 3H), 2.11 (dd, J=12.7, 6.8 Hz, 1H), 1.99-1.48 (m, 5H, assumed; partially obscured by water peak), 1.24 (t, J=7.1 Hz, 3H).

Example 10

Ethyl 6-{4-[2-(2,2,2-trifluoroethoxy)pyridin-3-yl]piperazin-1-yl}-2-azaspiro[3.4]octane-2-carboxylate (10)

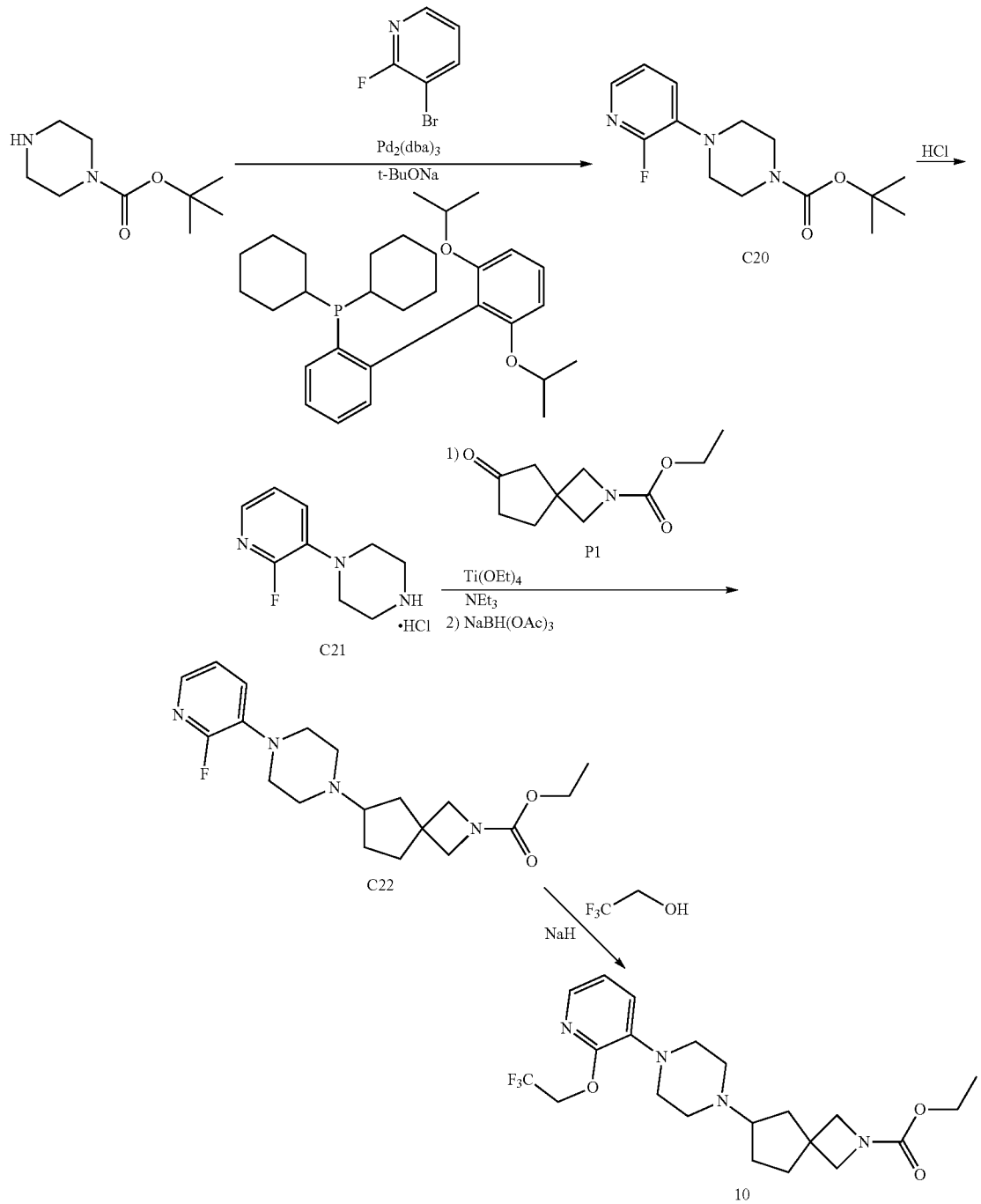

Step 1. Synthesis of tert-butyl 4-(2-fluoropyridin-3-yl)piperazine-1-carboxylate (C20)

A mixture of 3-bromo-2-fluoropyridine (10.0 g, 56.8 mmol), tert-butyl piperazine-1-carboxylate (12.7 g, 68.2 mmol), tris(dibenzylideneacetone)dipalladium(0) (2.60 g, 2.84 mmol), [2′,6′-bis(propan-2-yloxy)biphenyl-2-yl](dicyclohexyl)phosphane (RuPhos; 2.67 g, 5.72 mmol), and sodium tert-butoxide (11.0 g, 114 mmol) in 1,4-dioxane (150 mL) was stirred at 110° C. for 16 hours. After the reaction mixture had been concentrated in vacuo, the residue was diluted with ethyl acetate (300 mL), washed sequentially with water (2×150 mL) and saturated aqueous sodium chloride solution (150 mL), dried over sodium sulfate, filtered, and concentrated under reduced pressure. Silica gel chromatography (Gradient: 50% to 100% ethyl acetate in petroleum ether) afforded the product as a brown gum. Yield: 5.20 g, 18.5 mmol, 33%. LCMS m/z 282.2 [M+H]$^+$. $^1$H NMR (400 MHz, CDCl$_3$) δ 7.79 (ddd, J=4.9, 1.7, 1.5 Hz, 1H), 7.30-7.23 (m, 1H), 7.12 (ddd, J=7.8, 4.8, 1.4 Hz, 1H), 3.61 (br dd, J=5.1, 5.1 Hz, 4H), 3.06 (br dd, J=5.1, 4.9 Hz, 4H), 1.50 (s, 9H).

Step 2. Synthesis of 1-(2-fluoropyridin-3-yl)piperazine, hydrochloride salt (C21)

To a solution of C20 (5.20 g, 18.5 mmol) in dichloromethane (20 mL) was added a solution of hydrogen chloride in 1,4-dioxane (4.0 M; 18.5 mL, 74.0 mmol). The reaction mixture was stirred at room temperature for 4 hours, whereupon it was concentrated in vacuo to provide the crude product as a light brown solid, which was used in the next step without purification. By $^1$H NMR analysis, this material was not entirely pure. LCMS m/z 182.2 [M+H]$^+$. $^1$H NMR (400 MHz, DMSO-d$_6$), product peaks only: δ 9.7-9.4 (br m, 2H), 7.80 (br d, J=4.9 Hz, 1H), 7.58 (ddd, J=10.9, 7.9, 1.5 Hz, 1H), 7.29 (ddd, J=7.7, 4.9, 1.2 Hz, 1H), 3.33-3.15 (m, 8H).

Step 3. Synthesis of ethyl 6-[4-(2-fluoropyridin-3-yl)piperazin-1-yl]-2-azaspiro[3.4]octane-2-carboxylate (C22)

A mixture of C21 (from the previous step; 518.5 mmol), P1 (4.00 g, 18.4 mmol), titanium(IV) ethoxide (16.8 g, 73.6 mmol), and triethylamine (9.3 g, 92 mmol) in dichloromethane (80 mL) and methanol (80 mL) was stirred at room temperature overnight. Sodium triacetoxyborohydride (19.5 g, 92.0 mmol) was then added, and the reaction mixture was stirred at room temperature for another 3 hours. The reaction was quenched with water (10 mL), which produced a white precipitate; the mixture was then dried over sodium sulfate and filtered. The filter pad was washed with ethyl acetate (100 mL), and the combined filtrates were concentrated in vacuo. Chromatography on silica gel (Gradient: 50% to 100% ethyl acetate in petroleum ether) afforded the product as a white gum. Yield: 2.4 g, 6.6 mmol, 36% over 2 steps. LCMS m/z 363.2 [M+H]$^+$. $^1$H NMR (400 MHz, CDCl$_3$) δ 7.81 (ddd, J=4.9, 1.7, 1.5 Hz, 1H), 7.29 (ddd, J=10.3, 7.8, 1.7 Hz, 1H), 7.13 (ddd, J=7.8, 4.8, 1.3 Hz, 1H), 4.10 (q, J=7.1 Hz, 2H), 3.90 (AB quartet, J$_{AB}$=8.6 Hz, Δ$_{νAB}$=30.4 Hz, 2H), 3.80 (AB quartet, J$_{AB}$=8.3 Hz, Δ$_{νAB}$=7.6 Hz, 2H), 3.31 (br dd, J=4.9, 4.6 Hz, 4H), 3.11-2.98 (br m, 5H), 2.24 (dd, half of ABX pattern, J=13.1, 7.7 Hz, 1H), 2.18-2.09 (m, 1H), 2.08-1.82 (m, 4H), 1.24 (t, J=7.1 Hz, 3H).

Step 4. Synthesis of ethyl 6-{4-[2-(2,2,2-trifluoroethoxy)pyridin-3-yl]piperazin-1-yl}-2-azaspiro[3.4]octane-2-carboxylate (10)

Sodium hydride (60% dispersion in mineral oil; 32 mg, 0.80 mmol) in tetrahydrofuran (1 mL) was added to a 0° C. solution of 2,2,2-trifluoroethanol (75 mg, 0.75 mmol) in N,N-dimethylformamide (1 mL) and the resulting mixture was stirred at 0° C. for 30 minutes. A solution of C22 (90 mg, 0.25 mmol) in tetrahydrofuran (1 mL) was added, and the reaction mixture was stirred at 50° C. for 16 hours, whereupon it was diluted with ethyl acetate (30 mL), washed sequentially with water (2×10 mL) and saturated aqueous sodium chloride solution (10 mL), dried over sodium sulfate, filtered, and concentrated in vacuo. Reversed-phase HPLC (Column: Phenomenex Gemini C18, 5 μm; Mobile phase A: 0.05% ammonium hydroxide in water; Mobile phase B: acetonitrile; Gradient: 0% to 100% B) afforded the product as a light yellow gum. Yield: 29.5 mg, 66.7 μmol, 27%. LCMS m/z 443.2 [M+H]$^+$. $^1$H NMR (400 MHz, CDCl$_3$) δ 7.76 (dd, J=4.9, 1.5 Hz, 1H), 7.14 (dd, J=7.7, 1.6 Hz, 1H), 6.94 (dd, J=7.6, 4.9 Hz, 1H), 4.81 (q, JHF=8.6 Hz, 2H), 4.11 (q, J=7.1 Hz, 2H), 3.89 (AB quartet, downfield doublet is broadened, J$_{AB}$=8.4 Hz, Δ$_{νAB}$=23.3 Hz, 2H), 3.81 (AB quartet, J$_{AB}$=8.2 Hz, Δ$_{νAB}$=9.6 Hz, 2H), 3.25-3.07 (br m, 4H), 2.79-2.57 (br m, 5H), 2.18 (br dd, J=12, 7 Hz, 1H), 2.04-1.52 (m, 5H, assumed; partially obscured by water peak), 1.25 (t, J=7.1 Hz, 3H).

Example 11

Ethyl (6R)-6-{4-[3-(1,3-thiazol-5-yl)pyrazin-2-yl]piperazin-1-yl}-2-azaspiro[3.4]octane-2-carboxylate (11)

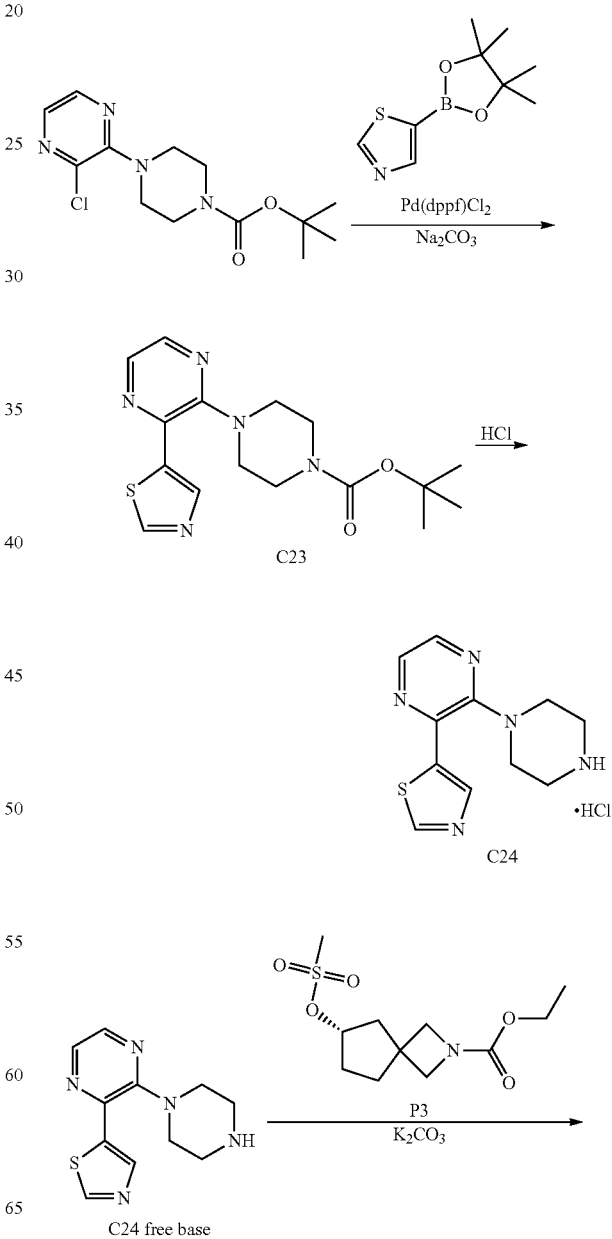

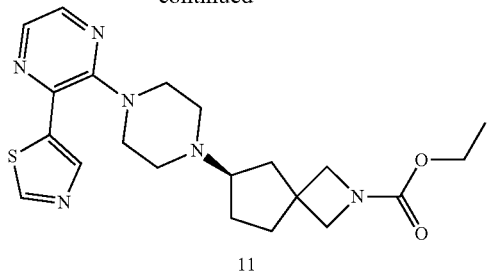

11

Step 1. Synthesis of tert-butyl 4-[3-(1,3-thiazol-5-yl)pyrazin-2-yl]piperazine-1-carboxylate (C23)

To a mixture of 5-(4,4,5,5-tetramethyl-1,3,2-dioxaborolan-2-yl)-1,3-thiazole (848 mg, 4.02 mmol) and tert-butyl 4-(3-chloropyrazin-2-yl)piperazine-1-carboxylate (1.00 g, 3.35 mmol) in toluene (35 mL) were added water (5 mL) and sodium carbonate (1.06 g, 10.0 mmol), followed by [1,1'-bis(diphenylphosphino)ferrocene]dichloropalladium(II) (245 mg, 0.335 mmol). The reaction vessel was then sealed and heated at 100° C. for 16 hours. After removal of solvents in vacuo, the residue was purified via chromatography on silica gel (Gradient: 0% to 90% ethyl acetate in petroleum ether) to afford the product as a yellow oil. Yield: 500 mg, 1.44 mmol, 43%. LCMS m/z 348.1 [M+H]$^+$. $^1$H NMR (400 MHz, CDCl$_3$) δ 9.0-8.8 (br s, 1H), 8.8-8.6 (br s, 1H), 8.23 (d, J=2.4 Hz, 1H), 8.17 (d, J=2.4 Hz, 1H), 3.68-3.57 (br m, 4H), 3.24-3.14 (br m, 4H), 1.48 (s, 9H).

Step 2. Synthesis of 2-(piperazin-1-yl}-3-(1,3-thiazol-5-yl)pyrazine, hydrochloride salt (C24)

A solution of hydrogen chloride in 1,4-dioxane (4 M; 3 mL, 12 mmol), was added to a solution of C23 (500 mg, 1.44 mmol) in acetonitrile (9 mL), and the reaction mixture was stirred for 16 hours at room temperature. It was then concentrated in vacuo, and the residue was triturated with ethyl acetate to provide the product as a yellow solid. Yield: 330 mg, 1.16 mmol, 81%. LCMS m/z 248.1 [M+H]$^+$. $^1$H NMR (400 MHz, DMSO-d$_6$), characteristic peaks: δ 8.36 (d, J=2.4 Hz, 1H), 8.32 (d, J=2.4 Hz, 1H), 3.40-3.33 (br m, 4H), 3.32-3.23 (br m, 4H).

Step 3. Synthesis of ethyl (6R)-6-{4-[3-(1,3-thiazol-5-yl)pyrazin-2-yl]piperazin-1-yl}-2-azaspiro[3.4]octane-2-carboxylate (11)

A mixture of C24 (free base; 120 mg, 0.485 mmol), P3 (242 mg 0.873 mmol), and potassium carbonate (67 mg, 0.48 mmol) in acetonitrile (4 mL) was stirred in a sealed vessel for 16 hours at 95° C. After concentration in vacuo, the residue was purified using silica gel chromatography (Gradient: 0% to 10% methanol in dichloromethane), followed by reversed-phase HPLC (Column: Phenomenex Gemini C18, μm; Mobile phase A: 0.1% formic acid in water; Mobile phase B: acetonitrile; Gradient: 12% to 20% B). The product was isolated as a light yellow gum. Yield: 30 mg, 70 μmol, 14%. LCMS m/z 429.2 [M+H]$^+$. $^1$H NMR (400 MHz, CDCl$_3$) δ 8.88 (s, 1H), 8.68 (s, 1H), 8.22 (d, J=2.4 Hz, 1H), 8.16 (d, J=2.4 Hz, 1H), 4.11 (q, J=7.2 Hz, 2H), 3.89 (AB quartet, J$_{AB}$=8.4 Hz, Δ$_{vAB}$=27.7 Hz, 2H), 3.83-3.77 (m, 2H), 3.44-3.29 (br m, 4H), 2.90-2.77 (br m, 5H), 2.18 (dd, J=13.0, 7.3 Hz, 1H), 2.05-1.70 (m, 5H), 1.24 (t, J=7.1 Hz, 3H).

Using the methodology described above for Examples 1-11 and analogous starting material as noted in the table, Examples 12-53 were synthesized. See Table 1 for specific methods employed, as well as characterization data for these Examples.

TABLE 1

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 12 | Examples 6 and 7[1] | 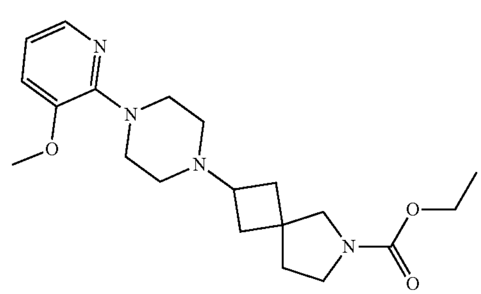 [SMILES: CCOC(=O)N1CCC2(CC(N3CCN(c4ncccc4OC)CC3)C2)C1] | $^1$H NMR (400 MHz, CD$_3$OD) δ 7.82 (dd, J = 4.9, 1.4 Hz, 1H), 7.32 (dd, J = 8.0, 1.2 Hz, 1H), 7.01 (dd, J = 7.9, 4.9 Hz, 1H), 4.25-4.08 (m, 4H), 3.89-3.79 (m, 1H), 3.88 (s, 3H), 3.61-3.35 (m, 6H), 3.2-3.0 (br m, 4H), 2.50-2.40 (m, 2H), 2.34-2.24 (m, 2H), 2.07-1.95 (m, 2H), 1.26 (t, J = 7.0 Hz, 3H); LCMS m/z 375.0 [M + H]$^+$ |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 13 | Examples 1, 2, and 3[1,2,3] | 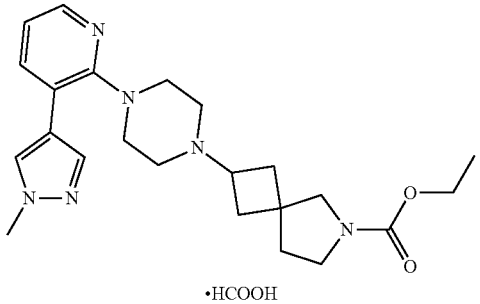 [SMILES: CCOC(=O)N1CCC2(CC(N3CCN(c4ncccc4-c4cnn(C)c4)CC3)C2)C1 ; "·HCOOH"] •HCOOH | 2.29 minutes[4]; 425 |
| 14 | Examples 1, 2, and 3[5] | 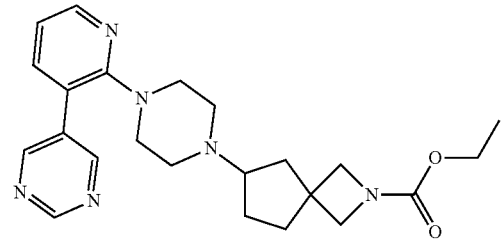 [SMILES: CCOC(=O)N1CC2(CCC(N3CCN(c4ncccc4-c4cncnc4)CC3)C2)C1] | $^1$H NMR (400 MHz, CD$_3$OD) δ 9.20 (s, 1H), 9.01 (s, 2H), 8.34 (dd, J = 4.9, 1.7 Hz, 1H), 7.50 (dd, J = 7.5, 1.8 Hz, 1H), 7.04 (dd, J = 7.5, 5.0 Hz, 1H), 4.10 (q, J = 7.1 Hz, 2H), 3.86 (AB quartet, downfield doublet is broad, J$_{AB}$ = 8.3 Hz, Δ$_{vAB}$ = 24.6 Hz, 2H), 3.80-3.74 (m, 2H), 3.28-3.05 (br m, 4H), 2.67-2.35 (br m, 5H), 2.16-2.05 (m, 1H), 2.01-1.47 (m, 5H, assumed; partially obscured by water peak), 1.24 (t, J = 7.2 Hz, 3H); LCMS m/z 423.2 [M + H]$^+$ |
| 15 | Examples 1, 2, and 3[6,3]; P1 | 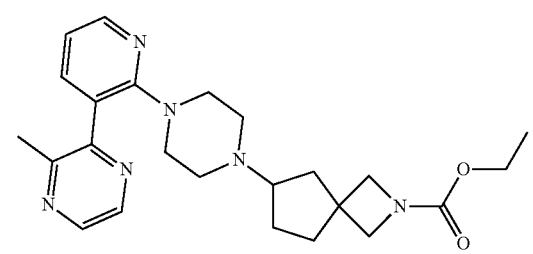 •HCOOH | 2.26 minutes[4]; 437 |
| 16 | Examples 1, 2, and 3[1,2,3] | 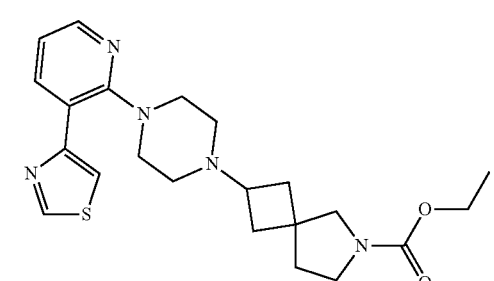 •HCOOH | 2.33 minutes[4]; 428 |

TABLE 1-continued

Method of preparation, structure, and physicochemical data for Examples 12-56.

| Example Number | Method of Preparation; Non-commercial starting materials | Structure | 1H NMR (400 MHz, CDCl3) δ; Mass spectrum, observed ion m/z [M + H]+ or HPLC retention time; Mass spectrum m/z [M + H]+ (unless otherwise indicated) |
|---|---|---|---|
| 17 | Examples 1, 2, and 3[6,3]; P1 | (structure) ·HCOOH | 2.16 minutes[4]; 423 |
| 18 | Examples 1, 2, and 3[2,3]; P1 | (structure) ·HCOOH | 2.34 minutes[4]; 412 |
| 19 | Examples 1, 2, and 3[7,8]; P1 | (structure) ENT-1 | 1H NMR (400 MHz, CD3OD) δ 7.77 (br d, J = 4 Hz, 1H), 7.51 (t, $J_{HF}$ = 73.1 Hz, 1H), 7.22 (br d, J = 7 Hz, 1H), 7.04 (dd, J = 7.6, 4.9 Hz, 1H), 4.10 (q, J = 7.1 Hz, 2H), 3.87 (AB quartet, $J_{AB}$ = 8.3 Hz, $\Delta_{vAB}$ = 22.0 Hz, 2H), 3.80 (AB quartet, $J_{AB}$ = 8.6 Hz, $\Delta_{vAB}$ = 7.7 Hz, 2H), 3.20-3.07 (br m, 4H), 2.74-2.58 (br m, 5H), 2.15 (dd, J = 12.5, 7.1 Hz, 1H), 2.01-1.80 (m, 3H), 1.80-1.69 (m, 1H), 1.65-1.51 (m, 1H), 1.24 (t, J = 7.1 Hz, 3H); LCMS m/z 411.2 [M + H]+ |
| 20 | Examples 1, 2, and 3[9,10]; P1 | (structure) ENT-1 | 1H NMR (400 MHz, CD3OD) δ 7.89 (dd, J = 4.8, 1.6 Hz, 1H), 7.29 (dd, J = 8.0, 1.6 Hz, 1H), 7.14 (dd, J = 7.8, 4.6 Hz, 1H), 4.10 (q, J = 7.1 Hz, 2H), 3.87 (AB quartet, $J_{AB}$ = 8.3 Hz, $\Delta_{vAB}$ = 20.9 Hz, 2H), 3.80 (AB quartet, $J_{AB}$ = 8.3 Hz, $\Delta_{vAB}$ = 7.6 Hz, 2H), 3.15-3.06 (br m, 4H), 2.70-2.59 (br m, 5H), 2.15 (dd, J = 12.7, 7.1 Hz, 1H), 2.00-1.80 (m, 3H), 1.74 (dd, J = 12.7, 9.5 Hz, 1H), 1.63-1.51 (m, 1H), 1.24 (t, J = 7.1 Hz, 3H); LCMS m/z 429.3 [M + H]+ |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 21 | Examples 1, 2, and 3[11,12]; P1 | 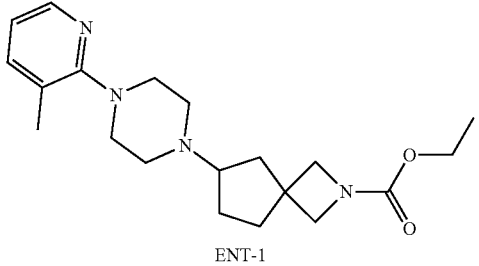<br>ENT-1 | $^1$H NMR (400 MHz, CD$_3$OD) δ 8.16 (dd, J = 4.9, 1.5 Hz, 1H), 7.42-7.37 (m, 1H), 6.85 (dd, J = 7.3, 4.9 Hz, 1H), 4.11 (q, J = 7.1 Hz, 2H), 3.89 (AB quartet, J$_{AB}$ = 8.4 Hz, Δ$_{vAB}$ = 26.2 Hz, 2H), 3.80 (AB quartet, J$_{AB}$ = 8.3 Hz, Δ$_{vAB}$ = 6.8 Hz, 2H), 3.29-3.16 (br m, 4H), 2.74-2.57 (br m, 5H), 2.27 (s, 3H), 2.16 (dd, J = 12.7, 7.1 Hz, 1H), 2.02-1.77 (m, 4H), 1.74-1.55 (m, 1H, assumed; obscured by water peak), 1.25 (t, J = 7.1 Hz, 3H); LCMS m/z 359.2 [M + H]$^+$ |
| 22 | Examples 1, 2, and 3[13,14]; P1 | 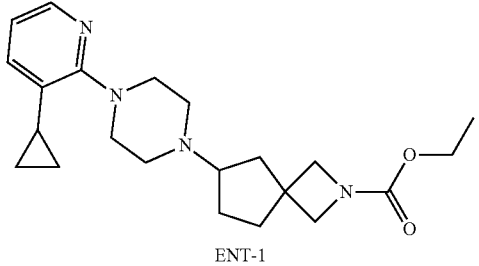<br>ENT-1 | $^1$H NMR (400 MHz, CD$_3$OD) δ 8.10 (dd, J = 4.8, 1.3 Hz, 1H), 7.10 (br d, J = 7.3 Hz, 1H), 6.84 (br dd, J = 7.2, 5.0 Hz, 1H), 4.11 (q, J = 7.1 Hz, 2H), 4.03-3.91 (br m, 1H), 3.88 (br d, half of AB quartet, J = 8.3 Hz, 1H), 3.82-3.77 (m, 2H), 3.62-3.18 (br m, 4H), 2.89-2.49 (br m, 5H), 2.30-2.11 (br m, 2H), 2.11-1.78 (m, 5H), 1.25 (t, J = 7.1 Hz, 3H), 1.06-1.00 (m, 2H), 0.76-0.70 (m, 2H); LCMS m/z 385.3 [M + H]$^+$ |
| 23 | Examples 1, 2, and 3[6,1,15,16] | 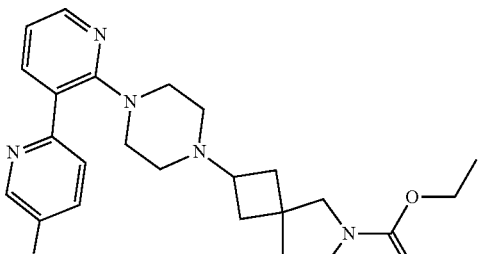<br>ENT-2 | From analysis of the $^1$H NMR, this material was presumed to exist as a mixture of rotamers. $^1$H NMR (400 MHz, CD$_3$OD) δ 8.94 (br d, J = 2 Hz, 1H), 8.31 (dd, J = 4.7, 2.0 Hz, 1H), 8.11 (br d, J = 8.2 Hz, 1H), 7.94 (dd, J = 8.4, 2.1 Hz, 1H), 7.91 (dd, J = 7.8, 2.0 Hz, 1H), 6.99 (br dd, J = 7.0, 5.1 Hz, 1H), 4.10 (br q, J = 7.0 Hz, 2H), 3.44-3.32 (m, 2H), [3.29 (s) and 3.24 (s), total 2H], 3.20-3.12 (m, 4H), 2.75-2.64 (m, 1H), 2.34-2.25 (m, 4H), 2.08-1.99 (m, 2H), 1.95-1.82 (m, 4H), 1.27-1.20 (m, 3H); LCMS m/z 447.3 [M + H]$^+$ |
| 24 | Examples 1, 2, and 3[6,15,17] | 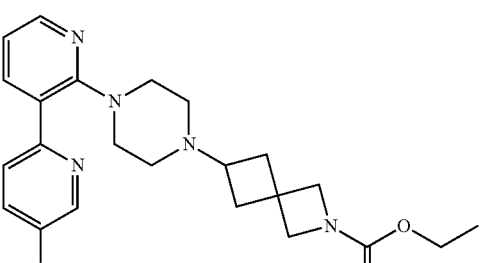 | $^1$H NMR (400 MHz, CD$_3$OD) δ 8.96 (br d, J = 2 Hz, 1H), 8.32 (dd, J = 4.7, 2.0 Hz, 1H), 8.12 (br d, J = 8.2 Hz, 1H), 7.95 (dd, J = 8.6, 2.3 Hz, 1H), 7.92 (dd, J = 7.4, 2.0 Hz, 1H), 7.01 (dd, J = 7.6, 4.9 Hz, 1H), 4.09 (q, J = 7.2 Hz, 2H), 3.99 (br s, 2H), 3.87 (br s, 2H), 3.21-3.11 (m, 4H), 2.67-2.55 (m, 1H), 2.36-2.24 (m, 6H), 2.09-1.98 (m, 2H), 1.23 (t, J = 7.0 |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
|  |  |  | Hz, 3H); LCMS m/z 433.2 [M + H]$^+$ |
| 25 | Example 10; C22 | 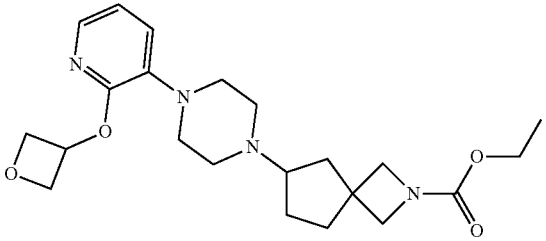 [SMILES: CCOC(=O)N1CC2(CCC(N3CCN(c4cccnc4OC4COC4)CC3)C2)C1] | $^1$H NMR (400 MHz, CD$_3$OD) δ 7.70 (dd, J = 4.9, 1.5 Hz, 1H), 7.12 (dd, J = 7.8, 1.5 Hz, 1H), 6.86 (dd, J = 7.7, 5.0 Hz, 1H), 5.67-5.59 (m, 1H), 5.02 (dd, J = 7.1, 6.8 Hz, 2H), 4.76 (dd, J = 7.6, 5.4 Hz, 2H), 4.10 (q, J = 7.1 Hz, 2H), 3.88 (AB quartet, J$_{AB}$ = 8.6 Hz, Δ$_{vAB}$ = 22.9 Hz, 2H), 3.80 (AB quartet, J$_{AB}$ = 8.2 Hz, Δ$_{vAB}$ = 9.9 Hz, 2H), 3.25-3.10 (br m, 4H), 2.80-2.60 (br m, 5H), 2.17 (dd, J = 12.7, 7.1 Hz, 1H), 2.02-1.90 (m, 2H), 1.90-1.73 (m, 2H), 1.69-1.55 (m, 1H), 1.24 (t, J = 7.1 Hz, 3H); LCMS m/z 417.3 [M + H]$^+$ |
| 26 | Examples 1, 2, and 3[18,19]; P1 | 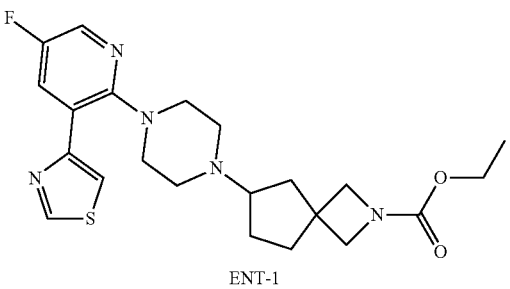<br>ENT-1 | $^1$H NMR (400 MHz, CD$_3$OD) δ 8.87 (d, J = 2.0 Hz, 1H), 8.23 (br s, 1H), 8.11 (d, J = 2.9 Hz, 1H), 8.03 (dd, J = 9.0, 2.9 Hz, 1H), 4.10 (q, J = 7.1 Hz, 2H), 3.88 (AB quartet, J$_{AB}$ = 8.4 Hz, Δ$_{vAB}$ = 23.3 Hz, 2H), 3.82-3.76 (m, 2H), 3.26-3.10 (br m, 4H), 2.72-2.52 (br m, 5H), 2.14 (dd, J = 12.6, 7.0 Hz, 1H), 2.03-1.71 (m, 4H, assumed; partially obscured by water peak), 1.70-1.54 (br m, 1H), 1.24 (t, J = 7.1 Hz, 3H); LCMS m/z 446.2 [M + H]$^+$ |
| 27 | Examples 1, 2, and 3[20,21]; P1 | 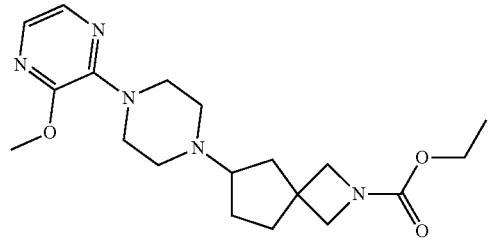<br>ENT-2 | $^1$H NMR (400 MHz, CD$_3$OD) δ 7.72 (d, J = 2.7 Hz, 1H), 7.56 (d, J = 2.7 Hz, 1H), 4.09 (br q, J = 6.9 Hz, 2H), 3.97 (s, 3H), 3.87 (br AB quartet, J$_{AB}$ = 8.2 Hz, Δ$_{vAB}$ = 23 Hz, 2H), 3.82-3.74 (m, 2H), 3.60-3.47 (br m, 4H), 2.70-2.52 (br m, 5H), 2.19-2.08 (m, 1H), 2.00-1.70 (m, 4H), 1.65-1.52 (m, 1H), 1.23 (t, J = 7.1 Hz, 3H), LCMS m/z 376.2 [M + H]$^1$ |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 28 | P1[22] | 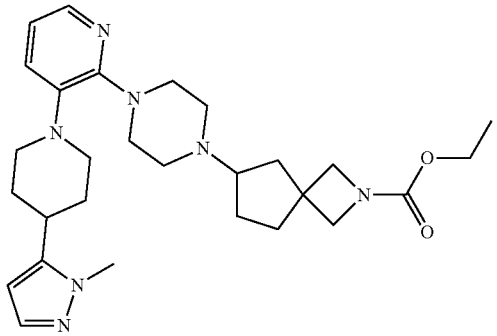 [SMILES: CCOC(=O)N1CC2(CCC(N3CCN(c4ncccc4N4CCC(c5ccnn5C)CC4)CC3)C2)C1] | 1.71 minutes[23]; 508.6 |
| 29 | P1[22] | 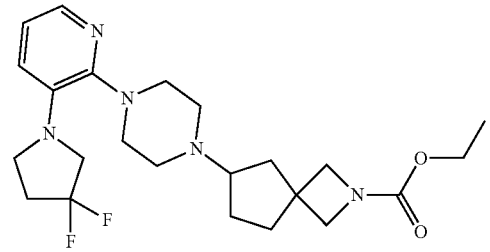 [SMILES: CCOC(=O)N1CC2(CCC(N3CCN(c4ncccc4N4CCC(F)(F)C4)CC3)C2)C1] | 1.94 minutes[23]; 450.6 |
| 30 | P1[22] | 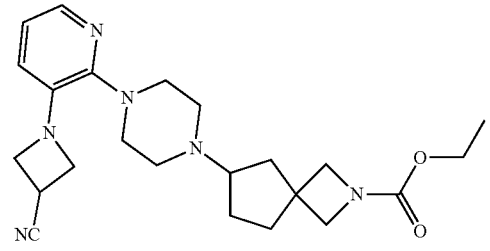 [SMILES: CCOC(=O)N1CC2(CCC(N3CCN(c4ncccc4N4CC(C#N)C4)CC3)C2)C1] | 1.90 minutes[23]; 425.2 |
| 31 | Examples 1, 2, and 3[2,3,24] | 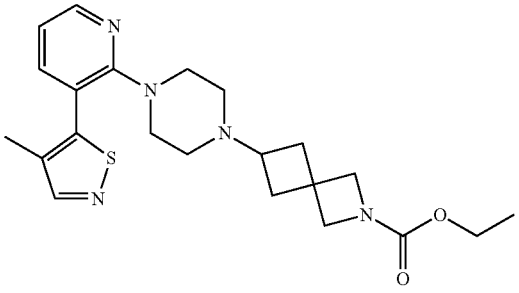 [SMILES: CCOC(=O)N1CC2(CC(N3CCN(c4ncccc4-c4sncc4C)CC3)C2)C1] | 2.39 minutes[4]; 428 |
| 32 | Examples 1, 2, and 3[2,3,24] | 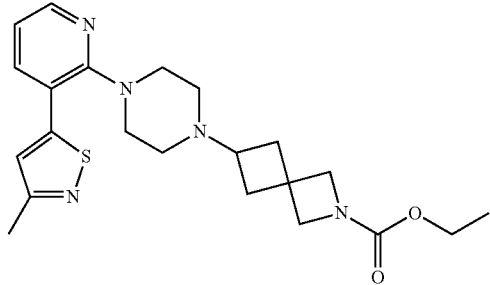 [SMILES: CCOC(=O)N1CC2(CC(N3CCN(c4ncccc4-c4cc(C)ns4)CC3)C2)C1] | 2.38 minutes[4]; 428 |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 33 | Examples 1, 2, and 3; P1 | 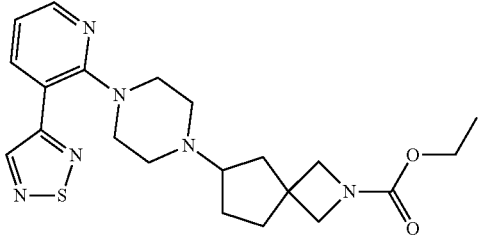 | $^1$H NMR (400 MHz, CD$_3$OD) δ 9.20 (s, 1H), 8.35 (dd, J = 4.8, 1.8 Hz, 1H), 8.00 (dd, J = 7.6, 2.0 Hz, 1H), 7.02 (dd, J = 7.5, 4.8 Hz, 1H), 4.09 (q, J = 7.1 Hz, 2H), 3.85 (AB quartet, J$_{AB}$ = 8.4 Hz, Δ$_{νAB}$ = 20.7 Hz, 2H), 3.80-3.75 (m, 2H), 3.12 (br dd, J = 4.9, 4.6 Hz, 4H), 2.63-2.44 (m, 5H), 2.10 (dd, J = 12.7, 6.8 Hz, 1H), 1.97-1.79 (m, 3H), 1.70 (dd, J = 12.7, 9.5 Hz, 1H), 1.59-1.48 (m, 1H), 1.23 (t, J = 7.1 Hz, 3H); LCMS m/z 429.2 {M + H]$^1$ |
| 34 | Example 33[25] | 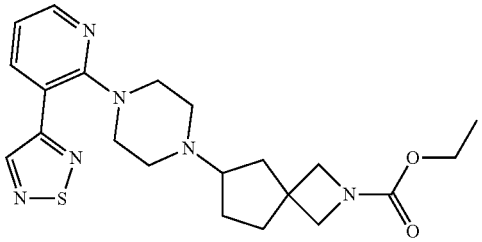 [SMILES: CCOC(=O)N1CC2(CCC(N3CCN(c4ncccc4-c4cnsn4)CC3)C2)C1]  ENT-1 | $^1$H NMR (400 MHz, CD$_3$OD) δ 9.20 (br s, 1H), 8.36 (dd, J = 4.5, 1.6 Hz, 1H), 8.01 (dd, J = 7.5, 1.6 Hz, 1H), 7.04 (br dd, J = 7.2, 4.8 Hz, 1H), 4.10 (q, J = 7.1 Hz, 2H), 3.93-3.86 (m, 1H), 3.83 (br d, half of AB quartet, J = 8 Hz, 1H), 3.82-3.75 (m, 2H), 3.23-3.06 (m, 4H), 2.66-2.43 (m, 5H), 2.18-2.06 (br m, 1H), 2.01-1.78 (br m, 3H), 1.78-1.46 (br m, 2H, assumed; partially obscured by water peak), 1.24 (t, J = 7.1 Hz, 3H); LCMS m/z 429.2 [M + H]$^1$ |
| 35 | Examples 1, 2, and 3[2,3,24] | 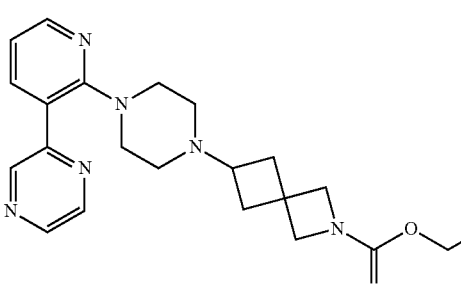  •HCOOH | 2.10 minutes[4]; 409 |
| 36 | Examples 1, 2, and 3[2,3]; P1 | 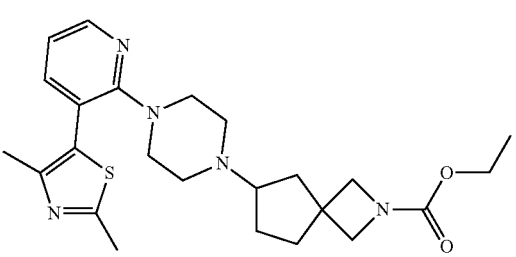  •HCOOH | 2.05 minutes[26]; 456 |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 37 | Examples 1, 2, and 3[2,3]; P1 | (structure) ·HCOOH | 2.21 minutes[26]; 488 |
| 38 | Examples 1, 2, and 3[2,3]; P1 | (structure) ·HCOOH | 2.18 minutes[26]; 452 |
| 39 | Examples 1, 2, and 3[2,3]; P1 | (structure) ·HCOOH | 1.97 minutes[4]; 461 |
| 40 | Examples 1, 2, and 3[2,3]; P1 | (structure) ·HCOOH | 2.07 minutes[4]; 462 |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 41 | Examples 1, 2, and 3[27]; P1 | 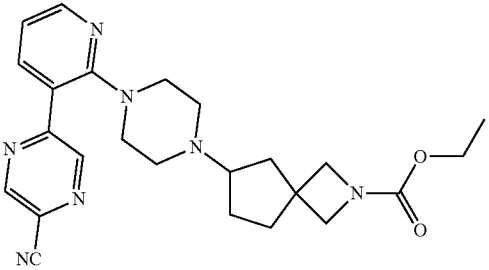 ENT-2 | $^1$H NMR (400 MHz, CD$_3$OD) δ 9.43 (d, J = 1.5 Hz, 1H), 8.95 (d, J = 1.5 Hz, 1H), 8.38 (dd, J = 4.8, 1.8 Hz, 1H), 7.98 (dd, J = 7.6, 2.0 Hz, 1H), 7.06 (dd, J = 7.6, 4.6 Hz, 1H), 4.10 (q, J = 7.1 Hz, 2H), 3.86 (AB quartet, J$_{AB}$ = 8.4 Hz, Δ$_{vAB}$ = 21.0 Hz, 2H), 3.81-3.75 (m, 2H), 3.28-3.14 (m, 4H), 2.67-2.43 (m, 5H), 2.11 (dd, J = 12.6, 7.0 Hz, 1H), 1.99-1.80 (m, 3H), 1.78-1.47 (m, 2H, assumed; partially obscured by water peak), 1.24 (t, J = 7.1 Hz, 3H); LCMS m/z 448.3 [M + H]$^1$ |
| 42 | Example 5[28]; P3 | 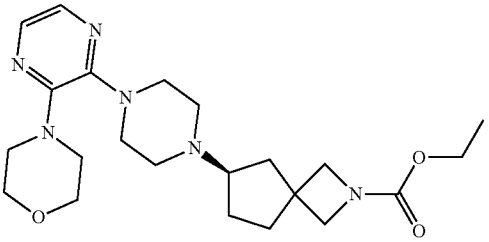 [SMILES: CCOC(=O)N1CC2(CC[C@@H](N3CCN(c4nccnc4N4CCOCC4)CC3)C2)C1] | 1.64 minutes[23]; 431.4 |
| 43 | Example 5[29]; P3 | 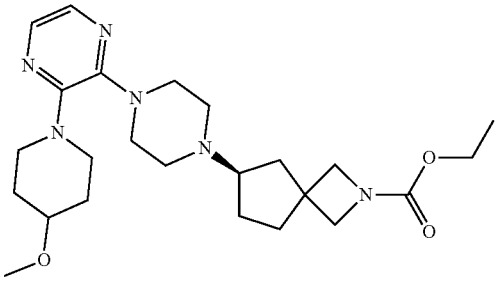 [SMILES: CCOC(=O)N1CC2(CC[C@@H](N3CCN(c4nccnc4N4CCC(OC)CC4)CC3)C2)C1] | 1.81 minutes[23]; 459.4 |
| 44 | Example 5[30]; P3 | 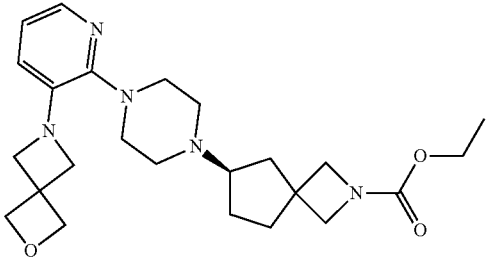 [SMILES: CCOC(=O)N1CC2(CC[C@@H](N3CCN(c4ncccc4N4CC5(COC5)C4)CC3)C2)C1] | 1.41 minutes[23]; 442.4 |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 45 | Examples 1, 2, and 3[31,15]; P1 | 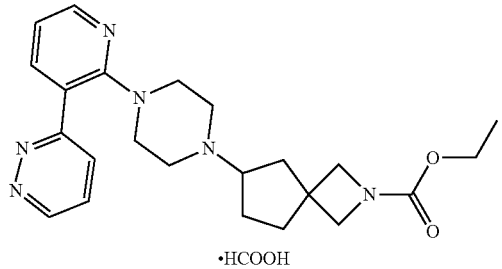 [SMILES: CCOC(=O)N1CC2(CCC(N3CCN(c4ncccc4-c4cccnn4)CC3)C2)C1 ; "·HCOOH"]·HCOOH | 2.07 minutes[4]; 423 |
| 46 | Example 8; P3 | 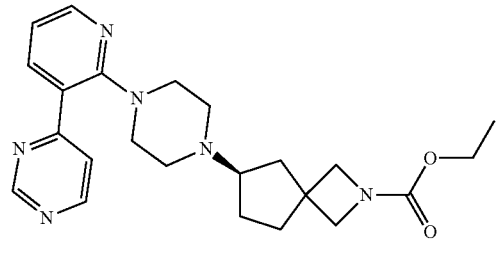 [SMILES: CCOC(=O)N1CC2(CC[C@@H](N3CCN(c4ncccc4-c4ccncn4)CC3)C2)C1] | $^1$H NMR (400 MHz, CD$_3$OD) δ 9.29 (d, J = 1.2 Hz, 1H), 8.73 (d, J = 5.1 Hz, 1H), 8.33 (dd, J = 4.8, 1.8 Hz, 1H), 8.02-7.97 (m, 2H), 7.00 (dd, J = 7.5, 4.8 Hz, 1H), 4.10 (q, J = 7.1 Hz, 2H), 3.86 (AB quartet, downfield doublet is broadened, J$_{AB}$ = 8.6 Hz, Δ$_{vAB}$ = 21.1 Hz, 2H), 3.81-3.75 (m, 2H), 3.32-3.12 (br m, 4H), 2.65-2.39 (br m, 5H), 2.11 (dd, J = 12.6, 7.0 Hz, 1H), 2.00-1.62 (m, 4H, assumed; partially obscured by water peak), 1.61-1.47 (br m, 1H), 1.24 (t, J = 7.2 Hz, 3H); LCMS m/z 423.3 [M + H]$^1$ |
| 47 | Example 8[6]; P3 | 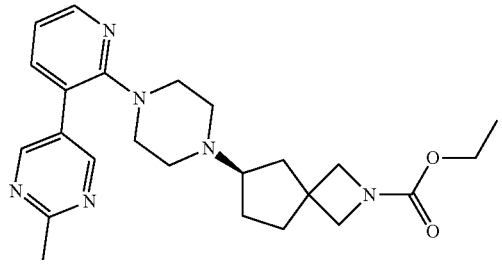 [SMILES: CCOC(=O)N1CC2(CC[C@@H](N3CCN(c4ncccc4-c4cnc(C)nc4)CC3)C2)C1] | $^1$H NMR (400 MHz, CD$_3$OD) δ 8.92 (s, 2H), 8.31 (dd, J = 4.9, 1.7 Hz, 1H), 7.46 (dd, J = 7.5, 1.8 Hz, 1H), 7.00 (dd, J = 7.6, 4.9 Hz, 1H), 4.10 (q, J = 7.1 Hz, 2H), 3.85 (AB quartet, J$_{AB}$ = 8.4 Hz, Δ$_{vAB}$ = 20.7 Hz, 2H), 3.80-3.74 (m, 2H), 3.18-3.08 (br m, 4H), 2.80 (s, 3H), 2.62-2.51 (m, 1H), 2.51-2.35 (br m, 4H), 2.09 (dd, J = 12.6, 7.0 Hz, 1H), 1.98-1.77 (m, 3H), 1.77-1.63 (m, 1H, assumed; partially obscured by water peak), 1.60-1.46 (m, 1H), 1.24 (t, J = 7.1 Hz, 3H); LCMS m/z 437.2 [M + H]$^1$ |
| 48 | Examples 1, 2, and 3[32] | 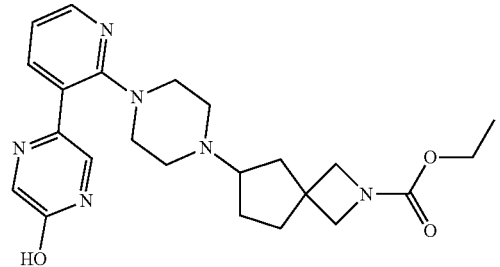 [SMILES: CCOC(=O)N1CC2(CCC(N3CCN(c4ncccc4-c4cnc(O)cn4)CC3)C2)C1] | $^1$H NMR (400 MHz, CD$_3$OD) δ 8.34 (br s, 1H), 8.25 (br d, J = 4.4 Hz, 1H), 8.19 (br s, 1H), 7.90 (br d, J = 6.8 Hz, 1H), 7.00 (dd, J = 7.3, 5.1 Hz, 1H), 4.09 (q, J = 7.1 Hz, 2H), 3.86 (AB quartet, J$_{AB}$ = 8.3 Hz, Δ$_{vAB}$ = 24.0 Hz, 2H), 3.81-3.74 (m, 2H), 3.34-3.21 (br m, 4H), 2.77-2.54 (br m, 5H), 2.13 (br dd, J = 12, 7 Hz, 1H), 2.01-1.75 (m, 4H), 1.71-1.57 (m, 1H), 1.23 (t, J = 7.2 Hz, 3H); LCMS m/z 439.3 [M + H]$^1$ |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 49 | Example 8[33,34]; P4 | 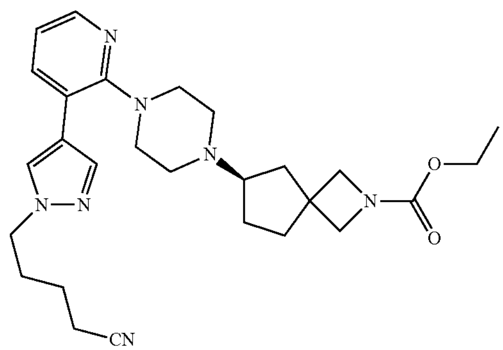 | 1.89 minutes[35]; 492.5 |
| 50 | Example 8[33,34]; P4 | 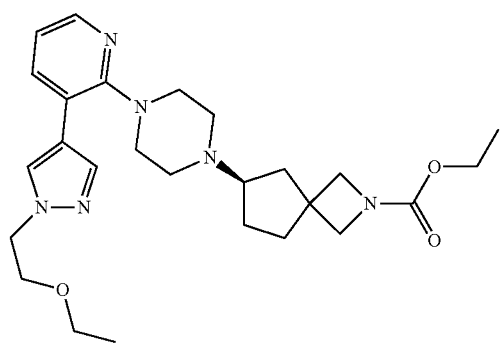 | 1.89 minutes[35]; 483.5 |
| 51 | Example 5[36]; P3 | 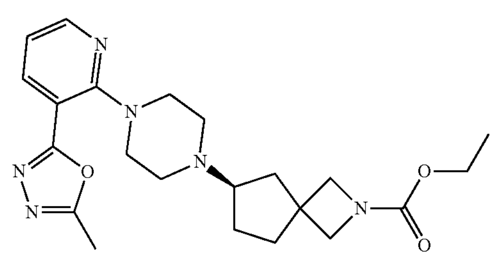 [SMILES: CCOC(=O)N1CC2(CC[C@@H](N3CCN(c4ncccc4-c4nnc(C)o4)CC3)C2)C1] | $^1$H NMR (400 MHz, CD$_3$OD) δ 8.37 (dd, J = 4.6, 2.0 Hz, 1H), 8.04 (br dd, J = 7.6, 1.5 Hz, 1H), 6.92 (dd, J = 7.5, 4.8 Hz, 1H), 4.10 (q, J = 7.1 Hz, 2H), 3.88 (AB quartet, downfield doublet is broadened, $J_{AB}$ = 8.6 Hz, $Δ_{νAB}$ = 24.7 Hz, 2H), 3.79 (AB quartet, $J_{AB}$ = 8.3 Hz, $Δ_{νAB}$ = 5.2 Hz, 2H), 3.46-3.26 (br m, 4H), 2.77-2.48 (br m, 5H), 2.62 (s, 3H), 2.15 (br dd, J = 12.5, 7.1 Hz, 1H), 2.04-1.50 (m, 5H, assumed; partially obscured by water peak), 1.24 (t, J = 7.1 Hz, 3H); LCMS m/z 427.3 [M + H]$^+$ |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 52 | Examples 1, 2, and 3[6,3]; P1 | 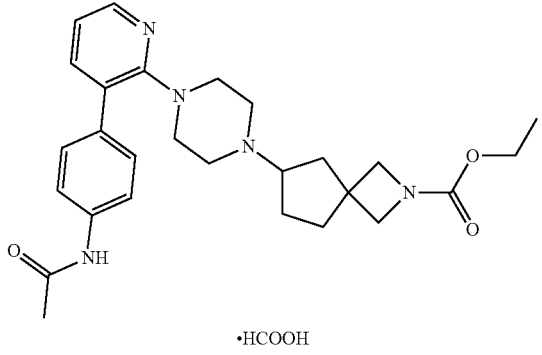 [SMILES: CCOC(=O)N1CC2(CCC(N3CCN(c4ncccc4-c4ccc(NC(C)=O)cc4)CC3)C2)C1 ; "·HCOOH"] ·HCOOH | 2.34 minutes[4]; 478 |
| 53 | Examples 1, 2, and 3[6,3]; P1 | 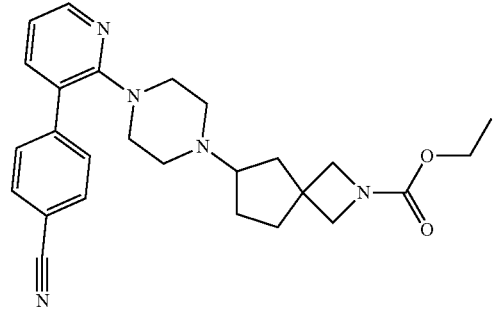 ·HCOOH | 2.64 minutes[4]; 446 |
| 54 | Examples 1, 2, and 3[37,38]; P1 | 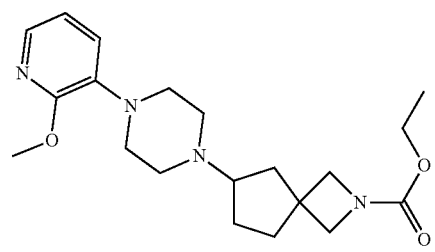 [SMILES: CCOC(=O)N1CC2(CCC(N3CCN(c4cccnc4OC)CC3)C2)C1] | N.D. |
| 55 | Examples 1, 2, and 3[37,38]; P1 | 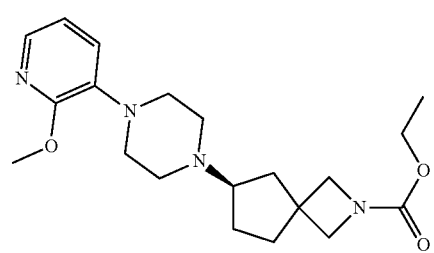 [SMILES: CCOC(=O)N1CC2(CC[C@@H](N3CCN(c4cccnc4OC)CC3)C2)C1] | N.D. |

TABLE 1-continued

Method of preparation, structure, and physicochemical data for Examples 12-56.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 56 | Examples 1, 2, and 3[37,38]; P1 | 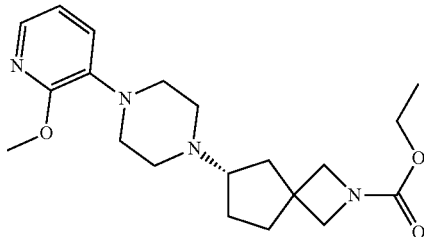 [SMILES: CCOC(=O)N1CC2(CC[C@H](N3CCN(c4cccnc4OC)CC3)C2)C1] | N.D. |

N.D. = not determined 1. tert-Butyl 2-oxo-6-azaspiro[3.4]octane-6-carboxylate was subjected to hydrogen chloride in 1,4-dioxane to remove the protecting group; subsequent reaction with ethyl chloroformate afforded the requisite ethyl 2-oxo-6-azaspiro [3.4]octane-6-carboxylate. 1H NMR (400 MHz, CDCl$_3$) δ 4.15 (q, J=7.2 Hz, 2H), 3.63-3.43 (br m, 4H), 3.05 (br AB quartet, J$_{AB}$=17 Hz, Δ$_{vAB}$=38 Hz, 4H), 2.08 (dd, J=6.8, 6.8 Hz, 2H), 1.27 (t, J=7.1 Hz, 3H).
2. In this case, the Suzuki coupling was carried out using [1,1'-bis(di-tert-butylphosphino)ferrocene]dichloropalladium(II) (Pd-118) and cesium carbonate or potassium carbonate.
3. In this case, the reductive amination was carried out with sodium cyanoborohyd ride, N,N-diisopropylethylamine, and magnesium sulfate.
4. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.
5. In this case, tert-butyl 6-oxo-2-azaspiro[3.4]octane-2-carboxylate was used in place of P1. The resulting tert-butyl 6-{4-[3-(pyrimidin-5-yl)pyridin-2-yl]piperazin-1-yl}-2-azaspiro[3.4]octane-2-carboxylate was deprotected with trifluoroacetic acid, and then reacted with 1-chloroethyl ethyl carbonate to afford Example 14.
6. In this case, the Suzuki coupling was carried out using [1,1'-bis(diphenylphosphino)ferrocene]dichloropalladium (II) and potassium carbonate.
7. The requisite 1-[2-(difluoromethoxy)pyridin-3-yl]piperazine was synthesized from 3-bromo-2-(difluoromethoxy) pyridine, using the method described in Example 10 for conversion of 3-bromo-2-fluoropyridine to C21.
8. The racemic product was separated into its enantiomers via reversed-phase HPLC (Column: Chiral Technologies Chiralpak IG; Mobile phase: 7:3 hexane/ethanol), and the first-eluting enantiomer was designated as Example 19. Both enantiomers were then individually subjected to reversed-phase chromatography (Column: Agela Technologies C18; Mobile phase A: 0.05% ammonium hydroxide in water; Mobile phase B: acetonitrile; Gradient: 0% to 100% B). On analytical HPLC (Column: Chiral Technologies Chiralpak IG, 4.6×150 mm, 5 μm; Mobile phase: 7:3 hexane/ethanol; Flow rate: 1.0 mL/minute), Example 19 exhibited a retention time of 5.25 minutes. The enantiomer of Example 19, ethyl 6-{4-[2-(difluoromethoxy)pyridin-3-yl]piperazin-1-yl}-2-azaspiro[3.4]octane-2-carboxylate, ENT-2, had a retention time of 6.08 minutes under the same conditions. The enantiomer of Example 19, LCMS m/z 411.2 [M+H]$^+$, exhibited the following biological data: M4 EC$_{50}$, 201 nM (3 determinations); M4 E$_{max}$ 74% (3 determinations).
9. The requisite 1-[2-(trifluoromethoxy)pyridin-3-yl]piperazine was synthesized from 3-bromo-2-(trifluoromethoxy) pyridine, using the method described in Example 10 for conversion of 3-bromo-2-fluoropyridine to C21.
10. The racemic product was separated into its enantiomers via reversed-phase HPLC (Column: Chiral Technologies Chiralcel OD, 10 μm; Mobile phase: 90:10 hexane/ethanol).
10. The first-eluting enantiomer was designated as Example 20. Both enantiomers were then individually subjected to reversed-phase chromatography (Column: Agela Technologies C18; Mobile phase A: 0.05% ammonium hydroxide in water; Mobile phase B: acetonitrile; Gradient: 0% to 100% B). On analytical HPLC (Column: Chiral Technologies Chiralcel OD-H, 4.6×150 mm, 5 μm; Mobile phase: 90:10 hexane/ethanol; Flow rate: 1.0 mL/minute), Example 20 exhibited a retention time of 4.31 minutes. The enantiomer of Example 20, ethyl 6-{4-[2-(trifluoromethoxy) pyridin-3-yl]piperazin-1-yl}-2-azaspiro[3.4]octane-2-carboxylate, ENT-2, had a retention time of 4.93 minutes under the same conditions. The enantiomer of Example 20, LCMS m/z 429.2 [M+H]$^+$, exhibited the following biological data: M4 EC$_{50}$, 3600 nM (2 determinations); M4 E$_{max}$ 95.3% (2 determinations).
11. In this case, starting material 1-(3-methylpyridin-2-yl)piperazine was commercially available.
12. The racemic product was separated into its enantiomers via reversed-phase HPLC (Column: Chiral Technologies Chiralcel OZ-H, 5 μm; Mobile phase: 80:20:0.1 hexane/ ethanol/diethylamine). The first-eluting enantiomer was designated as Example 21. Both enantiomers were then individually subjected to reversed-phase HPLC (Column: C18; Mobile phase A: 0.05% ammonium hydroxide in water; Mobile phase B: acetonitrile; Gradient: 70% to 75% B). On analytical HPLC (Column: Chiral Technologies Chiralcel OZ-H, 4.6×150 mm, μm; Mobile phase: 80:20:0.1 hexane/ ethanol/diethylamine; Flow rate: 1.0 mL/minute), Example 21 exhibited a retention time of 5.29 minutes. The enantiomer of Example 21, ethyl 6-[4-(3-methylpyridin-2-yl)

piperazin-1-yl]-2-azaspiro[3.4]octane-2-carboxylate, ENT-2, had a retention time of 6.04 minutes under the same conditions. The enantiomer of Example 21, LCMS m/z 359.3 [M+H]$^+$, exhibited the following biological data: M4 EC$_{50}$, >241 nM (4 determinations); M4 E$_{max}$ 76.2% (3 determinations).

13. Suzuki reaction of tert-butyl 4-(3-bromopyridin-2-yl)piperazine-1-carboxylate and cyclopropylboronic acid, in the presence of dichlorobis(tricyclohexylphosphine)palladium(II) and tripotassium phosphate, afforded the requisite tert-butyl 4-(3-cyclopropylpyridin-2-yl)piperazine-1-carboxylate.

14. The racemic product was separated into its enantiomers via reversed-phase HPLC (Column: Chiral Technologies Chiralpak AD-H, 5 µm; Mobile phase: 100:0.1 ethanol/diethylamine). The first-eluting enantiomer was designated as Example 22. Both enantiomers were then individually subjected to reversed-phase chromatography (Column: Agela Technologies C18; Mobile phase A: 0.05% ammonium hydroxide in water; Mobile phase B: methanol; Gradient: 5% to 80% B). On analytical HPLC (Column: Chiral Technologies Chiralpak AD-H, 4.6×250 mm, 5 µm; Mobile phase: 100:0.1 ethanol/diethylamine; Flow rate: 1.0 mL/minute), Example 22 exhibited a retention time of 12.00 minutes. The enantiomer of Example 22, ethyl 6-[4-(3-cyclopropylpyridin-2-yl)piperazin-1-yl]-2-azaspiro[3.4]octane-2-carboxylate, ENT-2, had a retention time of 14.94 minutes under the same conditions. The enantiomer of Example 22, LCMS m/z 385.2 [M+H]$^+$, exhibited the following biological data: M4 EC$_{50}$, 11.6 nM (6 determinations); M4 E$_{max}$ 103% (6 determinations).

15. In this case, the reductive amination was carried out with sodium triacetoxyborohydride.

16. The racemic product was separated into its enantiomers via supercritical fluid chromatography [Column: Chiral Technologies Chiralpak IG, 5 µm; Mobile phase 7:3 carbon dioxide/(2-propanol containing 0.2% 1-aminopropan-2-ol)]. The second-eluting enantiomer was designated as Example 23. On analytical HPLC [Column: Phenomenex Lux Cellulose-4, 4.6×250 mm, 5 µm; Mobile phase A: carbon dioxide; Mobile phase B: ethanol containing 0.2% (7 M ammonia in methanol); Gradient: 5% B for 1.00 minute, then 5% to 60% B over 8.00 minutes; Flow rate: 3.0 mL/minute; Back pressure: 120 bar], Example 23 exhibited a retention time of 7.31 minutes. The enantiomer of Example 23, ethyl 2-[4-(5-cyano-2,3'-bipyridin-2'-yl)piperazin-1-yl]-6-azaspiro[3.4]octane-6-carboxylate, ENT-1, had a retention time of 7.01 minutes under the same conditions. The enantiomer of Example 23, LCMS m/z 447.3 [M+H]$^+$, exhibited the following biological data: M4 EC$_{50}$, >10,000 nM (1 determination); M4 E$_{max}$, not determined.

17. In this case, tert-butyl 6-oxo-2-azaspiro[3.3]heptane-2-carboxylate was used in place of P1. The resulting tert-butyl 6-[4-(5-cyano-2,3'-bipyridin-2'-yl)piperazin-1-yl]-2-azaspiro[3.3]heptane-2-carboxylate was deprotected with trifluoroacetic acid, and then reacted with ethyl chloroformate to afford Example 24.

18. Reaction of tert-butyl piperazine-1-carboxylate with 2,3-dibromo-5-fluoropyridine and potassium carbonate provided tert-butyl 4-(3-bromo-5-fluoropyridin-2-yl)piperazine-1-carboxylate. This material was subjected to a Stille coupling with 4-(tributylstannanyl)-1,3-thiazole in the presence of tetrakis(triphenylphosphine)palladium(0) and cesium fluoride to afford the requisite tert-butyl 4-[5-fluoro-3-(1,3-thiazol-4-yl)pyridin-2-yl]piperazine-1-carboxylate.

19. The racemic product was separated into its enantiomers via reversed-phase HPLC (Column: Chiral Technologies Chiralpak AD-H, 5 µm; Mobile phase: 1:1 hexane/ethanol). The first-eluting enantiomer was designated as Example 26. On analytical HPLC (Column: Chiral Technologies Chiralpak AD-H, 4.6×250 mm, 5 µm; Mobile phase: 1:1 hexane/ethanol; Flow rate: 1.0 mL/minute), Example 26 exhibited a retention time of 7.81 minutes. The enantiomer of Example 26, ethyl 6-{4-[5-fluoro-3-(1,3-thiazol-4-yl)pyridin-2-yl]piperazin-1-yl}-2-azaspiro[3.4]octane-2-carboxylate, ENT-2, had a retention time of 16.42 minutes under the same conditions. The enantiomer of Example 26, LCMS m/z 446.2 [M+H]$^+$, exhibited the following biological data: M4 EC$_{50}$, 152 nM (4 determinations); M4 E$_{max}$ 67.1% (4 determinations).

20. The requisite 4-substituted tert-butyl piperazine-1-carboxylate was synthesized via reaction of tert-butyl piperazine-1-carboxylate with the appropriate chloro-substituted heteroaromatic reactant.

21. The racemic product was separated into its enantiomers via reversed-phase HPLC (Column: Chiral Technologies Chiralcel OJ, 10 µm; Mobile phase: 90:10:0.1 hexane/ethanol/diethylamine). The second-eluting enantiomer was designated as Example 27. Both enantiomers were then individually subjected to reversed-phase chromatography (Column: Agela Technologies C18; Mobile phase A: 0.05% ammonium hydroxide in water; Mobile phase B: methanol; Gradient: 0% to 100% B). On analytical HPLC (Column: Chiral Technologies Chiralcel OJ-H, 4.6×150 mm, 5 µm; Mobile phase: 90:10:0.1 hexane/ethanol/diethylamine; Flow rate: 1.0 mL/minute), Example 27 exhibited a retention time of 5.19 minutes. The enantiomer of Example 27, ethyl 6-[4-(3-methoxypyrazin-2-yl)piperazin-1-yl]-2-azaspiro[3.4]octane-2-carboxylate, ENT-1, had a retention time of 4.42 minutes under the same conditions. The enantiomer of Example 27, LCMS m/z 376.2 [M+H]$^+$, exhibited the following biological data: M4 EC$_{50}$, >10,000 nM (1 determination); M4 E$_{max}$, not determined.

22. Reaction of tert-butyl 4-(3-bromopyridin-2-yl)piperazine-1-carboxylate with the appropriate amine, sodium tert-butoxide, tris(dibenzylideneacetone)dipalladium(0), and 4,5-bis(diphenylphosphino)-9,9-dimethylxanthene (Xantphos) provided the coupled product, which was deprotected using trifluoroacetic acid. The resulting secondary amine was subjected to reductive amination with P1, sodium triacetoxyborohydride, and N,N-diisopropylethylamine to afford the Example.

23. Conditions for analytical HPLC. Column: Waters Atlantis dC18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

24. Reaction of tert-butyl 6-oxo-2-azaspiro[3.3]heptane-2-carboxylate with acetyl chloride in methanol afforded 6,6-dimethoxy-2-azaspiro[3.3]heptane. Treatment with ethyl chloroformate and triethylamine, followed by ketal deprotection with hydrochloric acid, provided the requisite ethyl 6-oxo-2-azaspiro[3.3]heptane-2-carboxylate. $^1$H NMR (400 MHz, CDCl$_3$) δ 4.19 (s, 4H), 4.14 (q, J=7.0 Hz, 2H), 3.31 (s, 4H), 1.26 (t, J=7.0 Hz, 3H).

25. Racemic Example 33 was separated into its enantiomers via reversed-phase HPLC (Column: Chiral Technologies Chiralpak IG, 5 µm; Mobile phase: 50/50/0.1 hexane/ethanol/diethylamine). The first-eluting enantiomer was designated as Example 34. Both enantiomers were then individually subjected to silica gel chromatography (Gradient: 0% to 10% methanol in dichloromethane). On analytical HPLC (Column: Chiral Technologies Chiralpak IG, 4.6×150 mm, 5 µm; Mobile phase: 1:1 hexane/ethanol; Flow rate: 1.0 mL/minute), Example 34 exhibited a retention time of 9.66 minutes. The enantiomer of Example 34, ethyl 6-{4-[3-(1,2,5-thiadiazol-3-yl)pyridin-2-yl]piperazin-1-yl}-2-azaspiro[3.4]octane-2-carboxylate, ENT-2, had a retention time of 15.53 minutes under the same conditions. The enantiomer of Example 34, LCMS m/z 429.2 [M+H]$^+$, exhibited the following biological data: M4 EC$_{50}$, 347 nM (3 determinations); M4 E$_{max}$ 72.3% (3 determinations).

26. Conditions for analytical HPLC. Column: Waters XBridge C18, 2.1×50 mm, 5 µm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute. 27. The racemic product was separated into its enantiomers via reversed-phase HPLC (Column: Chiral Technologies Chiralcel OD, 10 µm; Mobile phase: 3:2 hexane/ethanol). The second-eluting enantiomer was designated as Example 41. Both enantiomers were then individually subjected to reversed-phase chromatography (Column: Agela Technologies C18; Mobile phase A: 0.1% ammonium hydroxide in water; Mobile phase B: acetonitrile; Gradient: 10% to 60% B). On analytical HPLC (Column: Chiral Technologies Chiralcel OD-H, 4.6×150 mm, 5 µm; Mobile phase: 7:3 hexane/ethanol; Flow rate: 1.0 mL/minute), Example 41 exhibited a retention time of 6.02 minutes. The enantiomer of Example 41, ethyl 6-{4-[3-(5-cyanopyrazin-2-yl)pyridin-2-yl]piperazin-1-yl}-2-azaspiro[3.4]octane-2-carboxylate, ENT-1, had a retention time of 4.96 minutes under the same conditions. The enantiomer of Example 41, LCMS m/z 448.3 [M+H]$^+$, exhibited the following biological data: M4 EC$_{50}$, 268 nM (3 determinations); M4 E$_{max}$ 52.7% (3 determinations).

28. Reaction of tert-butyl 4-(3-chloropyrazin-2-yl)piperazine-1-carboxylate with morpholine and potassium carbonate provided the requisite tert-butyl 4-[3-(morpholin-4-yl)pyrazin-2-yl]piperazine-1-carboxylate.

29. Reaction of tert-butyl 4-(3-chloropyrazin-2-yl)piperazine-1-carboxylate with 4-methoxypiperidine and potassium carbonate provided the requisite tert-butyl 4-[3-(4-methoxypiperidin-1-yl)pyrazin-2-yl]piperazine-1-carboxylate.

30. Coupling of tert-butyl 4-(3-bromopyridin-2-yl)piperazine-1-carboxylate and 2-oxa-6-azaspiro[3.3]heptane was carried out using rac-BINAP-Pd-G3 (Aldrich, catalogue number 804967), 1,1'-binaphthalene-2,2'-diylbis(diphenylphosphane), and sodium tert-butoxide. The product was deprotected with trifluoroacetic acid to afford the requisite 6-[2-(piperazin-1-yl)pyridin-3-yl]-2-oxa-6-azaspiro[3.3]heptane.

31. In this case, the Suzuki coupling was carried out using [1,1'-bis(diphenylphosphino)ferrocene]dichloropalladium (II) and sodium bicarbonate.

32. In this case, the hydroxypyrazine was introduced as a (4-methoxybenzyl)oxy derivative. 5-Bromopyrazin-2-ol was reacted with 1-(chloromethyl)-4-methoxybenzene and silver carbonate to provide 2-bromo-5-[(4-methoxybenzyl)oxy]pyrazine, which was used in the coupling reaction. A trifluoroacetic acid-mediated deprotection was employed to remove the tert-butoxycarbonyl group; this also removed the 4-methoxybenzyl moiety.

33. Reaction of 4-iodo-1H-pyrazole with the appropriate haloalkyl reactant, in the presence of cesium carbonate and potassium iodide, provided the requisite 1-substituted 4-iodo-1H-pyrazole.

34. The Suzuki reaction was carried out using [1,1'-bis(di-tert-butylphosphino)ferrocene]dichloropalladium(II) (Pd-118) and tripotassium phosphate.

35. Conditions for analytical HPLC. Column: Waters Atlantis dC18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5.0% to 80% B, linear over 3.75 minutes, then 80% to 95% B over 0.25 minutes, then 95% B for 1.0 minute; Flow rate: 2 mL/minute.

36. Reaction of tert-butyl 4-[3-(ethoxycarbonyl)pyridin-2-yl]piperazine-1-carboxylate with hydrazine, followed by acetylation with acetyl chloride and N,N-diisopropylethylamine, provided tert-butyl 4-{3-[(2-acetylhydrazinyl)carbonyl]pyridin-2-yl}piperazine-1-carboxylate.

Subjection of this material to p-toluenesulfonyl chloride and triethylamine afforded the requisite tert-butyl 4-[3-(5-methyl-1,3,4-oxadiazol-2-yl)pyridin-2-yl]piperazine-1-carboxylate.

37. The requisite 1-[2-(methoxy)pyridin-3-yl]piperazine is synthesized from 3-bromo-2-(methoxy)pyridine, using the method described in Example 10 for conversion of 3-bromo-2-fluoropyridine to C21.

38. The racemic product is separated into its enantiomers via reversed-phase HPLC (Column: Chiral Technologies Chiralcel OD, 10 µm) using a hydrocarbon/ethanol solvent mixture as the mobile phase. If further purification is required, the enantiomers are individually subjected to reversed-phase chromatography.

The M4 agonist binding affinity for the compounds of the present invention was determined utilizing the following biological assay(s):

Biological Assay

Muscarinic hM4 Agonist GloSensor cAMP Assay Methods

Compounds were prepared in advance of the assay. Test compounds were solubilized in 100% dimethyl sulfoxide (DMSO, Sigma D8418) to a concentration of 30 mM. A 10-point intermediate dilution series using half log dilutions was created in 100% DMSO with a top concentration of 4 mM. The serially diluted compounds were spotted as 200 nL/well in a 384-well plate (Matrix Catalog Number 4325). The final compound concentration range in the assay was 10 M to 0.3 nM with a final DMSO concentration of 0.25%.

Human M4 mAChR expressing stable cell lines were generated using a parental HEK cell expressing the GloSensor construct (Promega Sor-L9 HEK293 human/M4/GloSensor Cell Clone Number 40). The cells were grown in 90% Dulbecco's Modified Eagle Medium (DMEM, Gibco 11960), 10% fetal bovine serum (FBS, Hyclone CH.30160-03), 1% Penicillin/Streptomycin (Gibco 15070-063), 500 g/mL Geneticin (Gibco 10131-027), 200 g/mL Hygromycin B (Invitrogen 10687-010) and 1% Glutamax (Thermo Fisher 35050061).

One day prior to assay, the cells were lifted using dissociation buffer (Gibco 13151-014) and spun in a centrifuge at 250 times gravity for 5 minutes at room temperature. Supernatant was removed and the cell pellet was resuspended in growth media to a concentration of $6.25 \times 10^6$ cells/mL. Cells were then added to white poly-d-lysine coated plates (Becton Dickinson 356661) as 40 µL per well (25,000 cells) and incubated overnight (20-24 hours) in a 37° C. humidified incubator with 5% carbon dioxide (C02).

The following day, culture media was removed from the cell plates and replaced with L of equilibration medium containing 88% CO2-independent medium (Invitrogen 18045088), 10% FBS and 2% GloSensor cAMP reagent (Promega E1291) that had been warmed to 37° C. Plates were then covered and incubated for 2 hours at room temperature while protected from light.

To the previously prepared serially diluted compound plates, 200 nL of 4 mM ACh (Sigma A2661, 10 μM final) or 200 nL of 100% DMSO (0.25% final) was added to the positive and negative control wells, respectively. Compound plates were then diluted by adding 16 μL of C02-independent media containing 10% FBS and an $EC_{80}$ concentration of isoproterenol (Sigma 16504). Prior to compound testing, concentration response curves were run for isoproterenol to determine the EC80 concentration. At the end of the 2 hour equilibration, 10 L was transferred from the compound plates to the cell plates. The cell plates were incubated an additional 7 minutes at room temperature and then read using a Multi-label EnVision plate reader (Perkin Elmer) for luminescence.

The raw data, expressed as relative light units, was analyzed using Activity Base (IDBS). The percent effect at each compound concentration was calculated based on and relative to the amount of cAMP produced by the positive and negative control wells contained on each assay plate. The positive control wells contained an $EC_{100}$ concentration of ACh and the negative control wells contained only DMSO. The concentration and % effect values were fit using a four-parameter logistic dose response equation, and the concentration required for 50% effect ($EC_{50}$) was determined as well as the maximum asymptote of the concentration response curve to define the efficacy.

TABLE 2

Biological activity and IUPAC name for Examples 1-56.
Number of replicates are shown in parenthesis.

| Example | $EC_{50}$ (nM) | % maximum effect | IUPAC name |
|---|---|---|---|
| 1 | 4.59 (4) | 82.7 (4) | ethyl 6-{4-[3-(5-methoxypyrazin-2-yl)pyridin-2-yl]piperazin-1-yl}-2-azaspiro[3.4]octane-2-carboxylate |
| 2 | >10,000 (1) | N.D.[b] | ethyl 6-{4-[3-(5-methoxypyrazin-2-yl)pyridin-2-yl]piperazin-1-yl}-2-azaspiro[3.4]octane-2-carboxylate, ENT-1 |
| 3 | 3.87 (5) | 83.7 (5) | ethyl 6-{4-[3-(5-methoxypyrazin-2-yl)pyridin-2-yl]piperazin-1-yl}-2-azaspiro[3.4]octane-2-carboxylate, ENT-2 |
| 4 | 2.17 (6) | 87.2 (6) | ethyl (6R)-6-{4-[3-(1,3-thiazol-4-yl)pyridin-2-yl]piperazin-1-yl}-2-azaspiro[3.4]octane-2-carboxylate |
| 5 | 1.60 (10) | 46.4 (10) | ethyl (6R)-6-{4-[3-(1,3,4-thiadiazol-2-yl)pyridin-2-yl]piperazin-1-yl}-2-azaspiro[3.4]octane-2-carboxylate |
| 6 | 1.57 (6) | 86.3 (6) | ethyl (6R)-6-[4-(3-methoxypyridin-2-yl)piperazin-1-yl]-2-azaspiro[3.4]octane-2-carboxylate |
| 7 | 425 (3) | 47.7 (3) | ethyl (6S)-6-[4-(3-methoxypyridin-2-yl)piperazin-1-yl]-2-azaspiro[3.4]octane-2-carboxylate |
| 8 | 2.23 (8) | 98.7 (8) | ethyl (6R)-6-{4-[3-(pyrazin-2-yl)pyridin-2-yl]piperazin-1-yl}-2-azaspiro[3.4]octane-2-carboxylate |
| 9 | 14.8 (1) | 68.2 (1) | ethyl (6R)-6-{4-[3-(4-methyl-1H-pyrazol-1-yl)pyridin-2-yl]piperazin-1-yl}-2-azaspiro[3.4]octane-2-carboxylate |
| 10 | 5.13 (10) | 91.5 (10) | ethyl 6-{4-[2-(2,2,2-trifluoroethoxy)pyridin-3-yl]piperazin-1-yl}-2-azaspiro[3.4]octane-2-carboxylate |
| 11 | 0.806 (4) | 66.4 (4) | ethyl (6R)-6-{4-[3-(1,3-thiazol-5-yl)pyrazin-2-yl]piperazin-1-yl}-2-azaspiro[3.4]octane-2-carboxylate |
| 12 | 23.3 (4) | 95.2 (4) | ethyl 2-[4-(3-methoxypyridin-2-yl)piperazin-1-yl]-6-azaspiro[3.4]octane-6-carboxylate |
| 13 | 4.82 (3) | 92.6 (3) | ethyl 2-{4-[3-(1-methyl-1H-pyrazol-4-yl)pyridin-2-yl]piperazin-1-yl}-6-azaspiro[3.4]octane-6-carboxylate, formate salt |
| 14 | 1.20[c] (3) | 93.7[c] (3) | ethyl 6-{4-[3-(pyrimidin-5-yl)pyridin-2-yl]piperazin-1-yl}-2-azaspiro[3.4]octane-2-carboxylate |
| 15 | 17.3 (3) | 58.5 (3) | ethyl 6-{4-[3-(3-methylpyrazin-2-yl)pyridin-2-yl]piperazin-1-yl}-2-azaspiro[3.4]octane-2-carboxylate, formate salt |
| 16 | 24.5 (2) | 104 (2) | ethyl 2-{4-[3-(1,3-thiazol-4-yl)pyridin-2-yl]piperazin-1-yl}-6-azaspiro[3.4]octane-6-carboxylate, formate salt |
| 17 | 4.41 (3) | 92.3 (3) | ethyl 6-{4-[3-(pyridazin-4-yl)pyridin-2-yl]piperazin-1-yl}-2-azaspiro[3.4]octane-2-carboxylate, formate salt |
| 18 | 5.11 (5) | 54.9 (5) | ethyl 6-{4-[3-(1,3-oxazol-2-yl)pyridin-2-yl]piperazin-1-yl}-2-azaspiro[3.4]octane-2-carboxylate, formate salt |
| 19 | 1.45 (5) | 78.4 (5) | ethyl 6-{4-[2-(difluoromethoxy)pyridin-3-yl]piperazin-1-yl}-2-azaspiro[3.4]octane-2-carboxylate, ENT-1 |
| 20 | 9.90 (4) | 75.3 (4) | ethyl 6-{4-[2-(trifluoromethoxy)pyridin-3-yl]piperazin-1-yl}-2-azaspiro[3.4]octane-2-carboxylate, ENT-1 |
| 21 | 4.01 (2) | 96.8 (2) | ethyl 6-[4-(3-methylpyridin-2-yl)piperazin-1-yl]-2-azaspiro[3.4]octane-2-carboxylate, ENT-1 |
| 22 | <0.0740 (3) | 107 (2) | ethyl 6-[4-(3-cyclopropylpyridin-2-yl)piperazin-1-yl]-2-azaspiro[3.4]octane-2-carboxylate, ENT-1 |
| 23 | 143 (4) | 85.0 (4) | ethyl 2-[4-(5-cyano-2,3'-bipyridin-2'-yl)piperazin-1-yl]-6-azaspiro[3.4]octane-6-carboxylate, ENT-2 |
| 24 | 53.8 (5) | 70.6 (5) | ethyl 6-[4-(5-cyano-2,3'-bipyridin-2'-yl)piperazin-1-yl]-2-azaspiro[3.3]heptane-2-carboxylate |
| 25 | 5.37 (4) | 83.1 (4) | ethyl 6-{4-[2-(oxetan-3-yloxy)pyridin-3-yl]piperazin-1-yl}-2-azaspiro[3.4]octane-2-carboxylate |
| 26 | 26.4 (3) | 59.8 (3) | ethyl 6-{4-[5-fluoro-3-(1,3-thiazol-4-yl)pyridin-2-yl]piperazin-1-yl}-2-azaspiro[3.4]octane-2-carboxylate, ENT-1 |
| 27 | 11.4 (2) | 25.1 (2) | ethyl 6-[4-(3-methoxypyrazin-2-yl)piperazin-1-yl]-2-azaspiro[3.4]octane-2-carboxylate, ENT-2 |
| 28 | 1.78 (4) | 60.0 (4) | ethyl 6-(4-{3-[4-(1-methyl-1H-pyrazol-5-yl)pipendin-1-yl]pyridin-2-yl}piperazin-1-yl)-2-azaspiro[3.4]octane-2-carboxylate |

TABLE 2-continued

Biological activity and IUPAC name for Examples 1-56.
Number of replicates are shown in parenthesis.

| Example | $EC_{50}$ (nM) | % maximum effect | IUPAC name |
|---|---|---|---|
| 29 | 4.45 (2) | 84.0 (2) | ethyl 6-{4-[3-(3,3-difluoropyrrolidin-1-yl)pyridin-2-yl]piperazin-1-yl}-2-azaspiro[3.4]octane-2-carboxylate |
| 30 | 2.28 (5) | 70.3 (5) | ethyl 6-{4-[3-(3-cyanoazetidin-1-yl)pyridin-2-yl]piperazin-1-yl}-2-azaspiro[3.4]octane-2-carboxylate |
| 31 | 13.5 (3) | 101 (3) | ethyl 6-{4-[3-(4-methyl-1,2-thiazol-5-yl)pyridin-2-yl]piperazin-1-yl}-2-azaspiro[3.3]heptane-2-carboxylate |
| 32 | 27.8 (3) | 84.3 (3) | ethyl 6-{4-[3-(3-methyl-1,2-thiazol-5-yl)pyridin-2-yl]piperazin-1-yl}-2-azaspiro[3.3]heptane-2-carboxylate |
| 33 | 1.31 (6) | 92.3 (6) | ethyl 6-{4-[3-(1,2,5-thiadiazol-3-yl)pyridin-2-yl]piperazin-1-yl}-2-azaspiro[3.4]octane-2-carboxylate |
| 34 | 1.28 (6) | 96.2 (6) | ethyl 6-{4-[3-(1,2,5-thiadiazol-3-yl)pyridin-2-yl]piperazin-1-yl}-2-azaspiro[3.4]octane-2-carboxylate, ENT-1 |
| 35 | 304 (2) | 94.2 (2) | ethyl 6-{4-[3-(pyrazin-2-yl)pyridin-2-yl]piperazin-1-yl}-2-azaspiro[3.3]heptane-2-carboxylate, formate salt |
| 36 | 7.72 (4) | 80.6 (4) | ethyl 6-{4-[3-(2,4-dimethyl-1,3-thiazol-5-yl)pyridin-2-yl]piperazin-1-yl}-2-azaspiro[3.4]octane-2-carboxylate, formate salt |
| 37 | 6.10 (3) | 24.7 (3) | ethyl 6-{4-[5'-(difluoromethoxy)-3,3'-bipyridin-2-yl]piperazin-1-yl}-2-azaspiro[3.4]octane-2-carboxylate, formate salt |
| 38 | 1.17 (4) | 74.7 (4) | ethyl 6-[4-(6'-methoxy-3,3'-bipyridin-2-yl)piperazin-1-yl]-2-azaspiro[3.4]octane-2-carboxylate, formate salt |
| 39 | 11.7 (2) | 59.6 (2) | ethyl 6-{4-[3-(imidazo[1,2-a]pyridin-6-yl)pyridin-2-yl]piperazin-1-yl}-2-azaspiro[3.4]octane-2-carboxylate, formate salt |
| 40 | 12.0 (3) | 81.6 (3) | ethyl 6-{4-[3-([1,2,4]triazolo[4,3-a]pyridin-6-yl)pyridin-2-yl]piperazin-1-yl}-2-azaspiro[3.4]octane-2-carboxylate, formate salt |
| 41 | 8.52 (3) | 82.4 (3) | ethyl 6-{4-[3-(5-cyanopyrazin-2-yl)pyridin-2-yl]piperazin-1-yl}-2-azaspiro[3.4]octane-2-carboxylate, ENT-2 |
| 42 | 12.3 (1) | 92.9 (1) | ethyl (6R)-6-{4-[3-(morpholin-4-yl)pyrazin-2-yl]pyridin-2-yl]piperazin-1-yl}-2-azaspiro[3.4]octane-2-carboxylate |
| 43 | 1.51 (2) | 55.5 (2) | ethyl (6R)-6-{4-[3-(4-methoxypiperidin-1-yl)pyrazin-2-yl]piperazin-1-yl}-2-azaspiro[3.4]octane-2-carboxylate |
| 44 | 1.00 (4) | 92.5 (4) | ethyl (6R)-6-{4-[3-(2-oxa-6-azaspiro[3.3]hept-6-yl)pyridin-2-yl]piperazin-1-yl}-2-azaspiro[3.4]octane-2-carboxylate |
| 45 | 8.20 (5) | 35.2 (5) | ethyl 6-{4-[3-(pyridazin-3-yl)pyridin-2-yl]piperazin-1-yl}-2-azaspiro[3.4]octane-2-carboxylate, formate salt |
| 46 | <1.75 (7) | 96.6 (6) | ethyl (6R)-6-{4-[3-(pyrimidin-4-yl)pyridin-2-yl]piperazin-1-yl}-2-azaspiro[3.4]octane-2-carboxylate |
| 47 | 2.78 (5) | 63.5 (5) | ethyl (6R)-6-{4-[3-(2-methylpyrimidin-5-yl)pyridin-2-yl]piperazin-1-yl}-2-azaspiro[3.4]octane-2-carboxylate |
| 48 | 8.49 (6) | 83.9 (6) | ethyl 6-{4-[3-(5-hydroxypyrazin-2-yl)pyridin-2-yl]piperazin-1-yl}-2-azaspiro[3.4]octane-2-carboxylate |
| 49 | 0.596 (5) | 60.9 (5) | ethyl (6R)-6-(4-{3-[1-(4-cyanobutyl)-1H-pyrazol-4-yl]pyridin-2-yl}piperazin-1-yl)-2-azaspiro[3.4]octane-2-carboxylate, trifluoroacetate salt |
| 50 | <0.389 (6) | 89.4 (4) | ethyl (6R)-6-(4-{3-[1-(2-ethoxyethyl)-1H-pyrazol-4-yl]pyridin-2-yl}piperazin-1-yl)-2-azaspiro[3.4]octane-2-carboxylate, trifluoroacetate salt |
| 51 | 1.99 (5) | 68.6 (5) | ethyl (6R)-6-{4-[3-(5-methyl-1,3,4-oxadiazol-2-yl)pyridin-2-yl]piperazin-1-yl}-2-azaspiro[3.4]octane-2-carboxylate |
| 52 | 0.568 (7) | 92 (7) | ethyl 6-(4-(3-(4-acetamidophenyl)pyridin-2-yl)piperazin-1-yl)-2-azaspiro[3.4]octane-2-carboxylate, formate salt |
| 53 | 1.75 (2) | 97 (2) | ethyl 6-(4-(3-(4-cyanophenyl)pyridin-2-yl)piperazin-1-yl)-2-azaspiro[3.4]octane-2-carboxylate, formate salt |
| 54 | N.D. | N.D. | ethyl 6-(4-(2-methoxypyridin-3-yl)piperazin-1-yl)-2-azaspiro[3.4]octane-2-carboxylate |
| 55 | N.D. | N.D. | ethyl (6R)-6-(4-(2-methoxypyridin-3-yl)piperazin-1-yl)-2-azaspiro[3.4]octane-2-carboxylate |
| 56 | N.D. | N.D. | ethyl (6S)-6-(4-(2-methoxypyridin-3-yl)piperazin-1-yl)-2-azaspiro[3.4]octane-2-carboxylate |

[a]Reported $EC_{50}$ values and $E_{max}$ values represent the geometric mean; the number of determinations is given in parentheses.
[b]N.D. = not determined
[c]In this case, the Example was tested as its formate salt.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the structure:

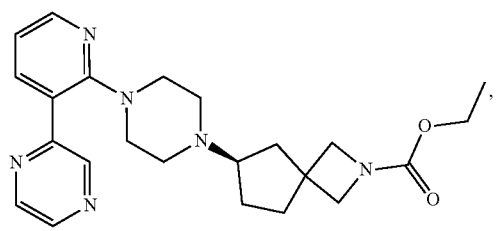 [SMILES: CCOC(=O)N1CC2(CC[C@@H](N3CCN(c4ncccc4-c4cnccn4)CC3)C2)C1]

or a pharmaceutically acceptable salt thereof.

2. A compound having the structure:

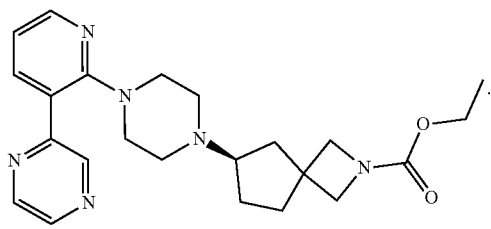 [SMILES: CCOC(=O)N1CC2(CC[C@@H](N3CCN(c4ncccc4-c4cnccn4)CC3)C2)C1]

3. A pharmaceutically acceptable salt of a compound having the structure:

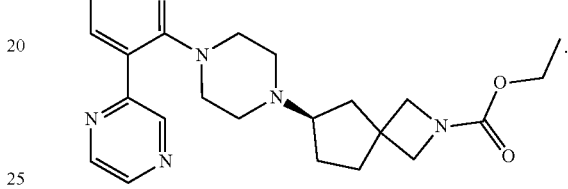

* * * * *